US011473086B2

(12) United States Patent
Xie et al.

(10) Patent No.: US 11,473,086 B2
(45) Date of Patent: Oct. 18, 2022

(54) LOSS OF FUNCTION ALLELES OF PTEPSP-TF AND ITS REGULATORY TARGETS IN RICE

(71) Applicant: UT-Battelle, LLC, Oak Ridge, TN (US)

(72) Inventors: Meng Xie, Oak Ridge, TN (US); Jin-Gui Chen, Oak Ridge, TN (US); Lee E. Gunter, Oak Ridge, TN (US); Sara S. Jawdy, Oak Ridge, TN (US); Wellington Muchero, Oak Ridge, TN (US); Gerald Tuskan, Oak Ridge, TN (US); Jin Zhang, Oak Ridge, TN (US)

(73) Assignee: UT-BATTELLE, LLC, Oak Ridge, TN (US)

( * ) Notice: Subject to any disclaimer, the term of this patent is extended or adjusted under 35 U.S.C. 154(b) by 0 days.

(21) Appl. No.: 16/445,888

(22) Filed: Jun. 19, 2019

(65) Prior Publication Data

US 2020/0399637 A1 Dec. 24, 2020

(51) Int. Cl.

*C12N 15/82* (2006.01)
*C12N 15/113* (2010.01)
*A01H 6/46* (2018.01)

(52) U.S. Cl.

CPC ........ *C12N 15/113* (2013.01); *C12N 15/8213* (2013.01); *C12N 15/8255* (2013.01); *A01H 6/4636* (2018.05); *C12N 2310/11* (2013.01); *C12N 2310/12* (2013.01); *C12N 2310/141* (2013.01)

(58) Field of Classification Search

CPC ........................................................ C12N 15/82
See application file for complete search history.

(56) References Cited

U.S. PATENT DOCUMENTS 4,987,071 A 1/1991 Cech et al.
5,034,323 A 7/1991 Jorgensen et al.
5,204,253 A 4/1993 Sanford et al.
5,254,678 A 10/1993 Haseloff et al.
5,538,880 A 7/1996 Lundquist et al.
6,013,863 A 1/2000 Lundquist et al.
6,326,527 B1 12/2001 Kirihara et al.
6,329,571 B1 12/2001 Hiei
6,423,885 B1 7/2002 Waterhouse et al.
6,452,067 B1 9/2002 Bedbrook et al.
6,573,099 B2 6/2003 Graham
6,753,139 B1 6/2004 Baulcombe et al.
6,777,588 B2 8/2004 Waterhouse et al.
2003/0175783 A1 9/2003 Waterhouse
2003/0175965 A1 9/2003 Lowe et al.
2003/0180945 A1 9/2003 Wang et al.
2004/0214330 A1 10/2004 Waterhouse et al.
2011/0104331 A1 5/2011 Hatanaka et al.
2012/0322122 A1* 12/2012 Shen .................. C12N 15/8243 435/162
2015/0353948 A1* 12/2015 Muchero ............ C12N 15/8218 800/282
2018/0002715 A1* 1/2018 Cigan ................ C12N 15/8212

FOREIGN PATENT DOCUMENTS

WO 97/01952 A1 1/1997
WO 98/36083 A1 8/1998
WO 98/53083 A1 11/1998
WO 99/32619 A1 7/1999

OTHER PUBLICATIONS

Tiwari S.B et al., "The Roles of Auxin Response Factor Domains in Auxin-Responsive Transcription", *The Plant Cell* 15:533-543 (Feb. 2003).
Tschaplinski T J et al., "Down-Regulation of the Caffeic Acid O-Methyltransferase Gene in Switchgrass Reveals a Novel Monolignol Analog", *Biotechnology for Biofuels* 5:71 (2012).
Vannini C. et al., "Overexpression of the Rice *Osmyb4* Gene Increases Chilling and Freezing Tolerance of *Arabidopsis thaliana* Plants", *The Plant Journal* 37:115-127 (2004).
Vogt T., "Phenylpropanoid Biosynthesis", Molecular Plant 3(1):2-20 (Jan. 2010).
Wang L. et al., "A Dynamic Gene Expression Atlas Covering the Entire Life Cycle of Rice", *The Plant Journal* 61:752-766 (2010).
Wilkins O. et al., "Expansion and Diversification of the Populus R2R3-MYB Family of Transcription Factors", *Plant Physiology* 749:981-993 (Feb. 2009).
Xie M. et al., "Identification of Functional Single Nucleotide Polymorphism of *Populus Trichocarpa PtrEPSP-TF* and Determination of its Transcriptional Effect", *Plant Direct* 4:1-13 (2020).
Xie M. et al., "Regulation of Lignin Biosynthesis and its Role in Growth-Defense Tradeoffs", *Frontiers in Plant Science* 9:1427 (Sep. 2018).
Xie M. et al., "A 5-Enolpyruvylshikimate 3-Phosphate Synthase Functions as a Transcriptional Repressor in *Populus*," *The Plant Cell* 30:1645-1660 (Jul. 2018).
Xie M. et al., "A Subgroup of SGS3-Like Proteins Act Redundantly in RNA-Directed DNA Methylation", *Nucleic Acids Research* 40(10):4422-4431 (Feb. 2012).
Yan H. et al., "New Construct Approaches for Efficient Gene Silencing in Plants", *Plant Physiology* 141:1508-1518 (Aug. 2006).
Yoo S-D et al., "*Arabidopsis* Mesophy II Protoplasts: A Versatile Cell System for Transient Gene Expression Analysis", *Nature Protocols* 2(7):1565-1572 (2007).
Zhao C. et al., "XND1, a Member of the NAC Domain Family in *Arabidopsis thaliana*, Negatively Reulates Lignocellulose Synthesis and Programmed Cell Death in Xylem", *The Plant Journal* 55:425-436 (2008).

(Continued)

*Primary Examiner* — Brent T Page
(74) *Attorney, Agent, or Firm* — Scully, Scott, Murphy & Presser, P.C.

(57) ABSTRACT

The present disclosure provides genetically modified plants, plant cells and plant tissues that show reduced lignin content as compared to a control plant which was not genetically modified. In addition, the disclosure provides methods of regulating lignin content in a plant. The disclosure also provides methods of producing bioproducts using the genetically modified plants of the instant disclosure.

14 Claims, 10 Drawing Sheets
(10 of 10 Drawing Sheet(s) Filed in Color)

Specification includes a Sequence Listing.

(56) References Cited

OTHER PUBLICATIONS

Zhong R. et al., "The Poplar MYB Master Switches Bind to the SMRE Site and Activate the Secondary Wall Biosynthetic Program During Wood Formation", *Plos One* 8(7):e69219 (Jul. 2013).
Zhong R. et al., "MYB46 and MYB83 Bind to the SMRE Sites and Directly Activate a Suite of Transcription Factors and Secondary Wall Biosynthetic Genes", *Plant Cell Physiol* 53(2):368-380 (2012).
Zhong R. et al., "Transcriptional Activation of Secondary Wall Biosynthesis by Rice and Maize NAC and MYB Transcription Factors", *Plant Cell Physiol*. 52(10):1856-1871 (2011).
Zhong R. et al., "A Battery of Transcription Factors Involved in the Regulation of Secondary Cell Wall Biosynthesis in *Arabidopsis*", *The Plant Cell* 20:2763-2782 (Oct. 2008).
Zhou J. et al., "MYB58 and MYB63 are Transcriptional Activators of the Lignin Biosynthesis Pathway During Secondary Cell Wall Formation in *Arabidopsis*", *The Plant Cell* 21:248-266 (Jan. 2009).
Cerd́ án P.D. et al., "A 146 bp Fragment of the Tobacco Lhcb1*2 Promoter Confers Very-Low-Fluence, Low-Fluence and High-Irradiance Responses of Phytochrome to a Minimal CaMV 35S Promoter", Plant Molecular Biology 33:245-255 (1997).
Cermak T. et al., "Efficient Design and Assembly of Custom TALEN and Other TAL Effector-Based Constructs for DNA Targeting", Nucleic Acids Research 39(12):e82 (Apr. 14, 2011).
Chang S.H. et al., "Enhancement of Plant Formation from Embryo Cultures of Taxus Mairei Using Suitable Culture Medium and PVP", Bot. Bull. Acad. Sin. 37:35-40 (1996).
Chow C-N et al., "PlantPAN 2.0: An Update of Plant Promoter Analysis Navigator for Reconstructing Transcriptional Regulatory Networks in Plants", Nucleic Acids Research 44:D1154-D1160 (Oct. 17, 2015).
Conkling M.A et al., "Isolation of Transcriptionally Regulated Root-Specific Genes from Tobacco", Plant Physiol. 93:1203-1211 (1990).
Dai S et al., "RF2b, a Rice bZIP Transcription Activator, Interacts With RF2a and is Involved in Symptom Development of Rice Tungro Disease", PNAS 101(2):687-692 (Jan. 13, 2004).
Evans L M et al., "Population Genomics of Populus Trichocarpa Identifies Signatures of Selection and Adaptive Trait Associations", Nature Genetics 46:1089 (2014).
Fejes E. et al., "A 268 bp Upstream Sequence Mediates the Circadian Clock-Regulated Transcription of the Wheat Cab-1 Gene in Transgenic Plants", Plant Molecular Biology 15:921-932 (1990).
Fornalé S. et al., "AtMYB7, a New Player in the Regulation of UV-Sunscreens in *Arabidopsis Thaliana*", Plant & Dell Physiology 55(3):507-516 (2014).
Fraser C.M. et al., "The Phenylpropanoid Pathway in *Arabidopsis*", *Arabidopsis* Book 9:e0152 (2011).
Fromm H. et al., "An Octopine Synthase Enhancer Element Directs Tissue-Specific Expression and Binds ASF-1, a Factor from Tobacco Nuclear Extracts", The Plant Cell 1:977-984 (Oct. 1989).
Hirano K. et al., "Survey of Genes Involved in Rice Secondary Cell Wall Formation Through a Co-Expression Network", Plants Cell Physiology 54(11):1803-1821 (2013).
Hirano K. et al., "Identification of Transcription Factors Involved in Rice Secondary Cell Wall Formation", Plant & Cell Physiology 54(11):1791-1802 (2013).
Howe E.A. et al., "RNA-Seq Analysis in Mev", Bioinformatics 27(22):3209-3210 (2011).
Hsu P.D. et al., "Development and Applications of CRISPR-Cas9 for Genome Engineering", Cell 157(6):1262-1278 (Jun. 5, 2014).
Hussey S G et al., "SND2, a NAC Transcription Factor Gene, Regulates Genes Involved in Secondary Cell Wall Development in *Arabidopsis* Fibres and Increases Fibre Cell Area in Eucalyptus", BMC Plant Biology 11:173 (2011).
Jacobs T.B. et al., "Simple Gene Silencing Using the Trans-Acting siRNA Pathway", Plant Biotechnology Journal 14:117-127(2016).
Jiang W. et al., "RNA-Guided Editing of Bacterial Genomes Using CRISPR-Cas Systems", Nature Biotechnology 31 (3):233-239 (Mar. 2013).
Jin H. et al., "Transcriptional Repression by AtMYB4 Controls Production of UV-Protecting Sunscreens in *Arabidopsis*", The EMBO Journal 19(22):6150-6161 (2000).
Keller B. et al., "Vascular-Specific Expression of the Bean GRP 1.8 Gene is Negatively Regulated", The Plant Cell 3:1051-1061 (Oct. 1991).
Kim W-C et al., "Identification of Direct Targets of Transcription Factor MYB46 Provides Insights into the Transcriptional Regulation of Secondary Wall Biosynthesis", Plant Mol Biol 85:589-599 (2014).
Kim D. et al., "TopHat2: Accurate Alignment of Transcriptomes in the Presence of Insertions, Deletions and Gene Fusions", Genome Biology 14:R36 (2013).
Kobayashi K. et al., "Transcriptional Repression by MYB3R Proteins Regulates Plant Organ Growth", The EMBO Journal 34(15):1992-2007 (2015).
Kúhn R. et al., "CrelloxP Recombination System and Gene Targeting", Methods in Molecular Biology, Transgenesis Techniques: Principles and Protocols 180:175-204 (2002).
Lam E. et al., "Site-Specific Mutations Alter In Vitro Factor Binding and Change Promoter Expression Pattern in Transgenic Plants", Proc. Natl. Acad Sci. USA 86:7890-7894 (Oct. 1989).
Li Y. et al., "Combined Inactivation of the Clostridium Cellulolyticum Lactate and Malate Dehydrogenase Genes Substantially Increases Ethanol Yield from Cellulose and Switchgrass Fermentations", Biotechnology for Biofuels 5:2 (2012).
Lin F. et al., "Proteomics Coupled With Metabolite and Cell Wall Profiling Reveal Metabolic Processes of a Developing Rice Stem Internode", Frontiers in Plant Science 8:1134 (Jul. 2017).
Love M. et al., "Moderated Estimation of Fold Change and Dispersion for RNA-Seq Data With DESeq2", GenomeBiology 15:550 (2014).
Luan S. et al., "A Rice cab Gene Promoter Contains Separate Cis-Acting Elements That Regulate Expression in Dicot and Monocot Plants", The Plant Cell 4:971-981 (Aug. 1992).
Lübberstedt T. et al., "Promoters from Genes for Plastid Proteins Possess Regions With Different Sensitivities Toward Red and Blue Light", Plant Physiol. 104:997-1006 (1994).
Maeda H. et al., "The Shikimate Pathway and Aromatic Amino Acid Biosynthesis in Plants", The Annual Review of Plant Biology 63:73-105 (2012).
Mali P. et al., "RNA-Guided Human Genome Engineering Via Cas9", Science 339:823-826 (Feb. 15, 2013).
Mann D Gj et al., "Gateway-Compatible Vectors for High-Throughput Gene Functional Analysis in Switchgrass (*Panicum virgatum* L.) and Other Monocot Species", Plant Biotechnology Journal 10:226-236 (2012).
Mann D Gj et al., "Switchgrass (*Panicum virgatum* L.) Polyubiquitin Gene (PvUbil and PvUbi2) Promoters for Use in Plant Transformation", BMC Biotechnology 11:74 (2011).
Matsuoka M. et al., "Tissue-Specific Light-Regulated Expression Directed by the Promoter of a C4 Gene, Maize Pyruvate, Orthophosphate Dikinase, in a C3 Plant, Rice", Proc. Natl. Acad. Sci. USA 90:9586-9590 (Oct. 1993).
Medberry S.L. et al., "The Commelina Yellow Mottle Virus Promoter is a Strong Promoter in Vascular and Reproductive Tissues", The Plant Cell 4:185-192 (Feb. 1992).
Mehrtens F. et al., "The *Arabidopsis* Transcription Factor MYB12 is a Flavonol-Specific Regulator of Phenylpropanoid Biosynthesis", Plant Physiology 138:1083-1096 (Jun. 2005).
Muchero W. et al., "High-Resolution Genetic Mapping of Allelic Variants Associated With Cell Wall Chemistry in Populus", BMC Genomics 16:24 (2015).
Nakano Y. et al., "NAC-MYB-Based Transcriptional Regulation of Secondary Cell Wall Biosynthesis in Land Plants", Frontiers in Plant Science 6:288 (May 2015).
Perriman R. et al., "Effective Ribozyme Delivery in Plant Cells", Proc. Natl. Acad. Sci. USA 92(13):6175-6179 (Jun. 1995).
Preston J. et al., "AtMYB32 is Required for Normal Pollen Development in *Arabidopsis thaliana*", The Plant Journal 40:979-995 (2004).
Ran F A et al., "Genome Engineering Using the CRISPR-Cas9 System", Nature Protocols 8(11):2281-2308 (2013).

(56) References Cited

OTHER PUBLICATIONS

Rao X. et al., "Current Models for Transcriptional Regulation of Secondary Cell Wall Biosynthesis in Grasses", Frontiers in Plant Science 9:399 (Apr. 2018).
Rauf M. et al., "NAC Transcription Factors Speedy Hyponastic Growth Regulates Flooding-Induced Leaf Movement in *Arabidopsis*", The Plant Cell 25:4941-4955 (Dec. 2013).
Rogers L.A. et al., "The Genetic Control of Lignin Deposition During Plant Growth and Development", New Phytologist 164:17-30 (2004).
Satlewal A. et al., "Rice Straw as a Feedstock for Biofuels: Availability, Recalcitrance, and Chemical Properties", Biofuels Bioproducts & Biorefining 12:83-107 (2018).
Shannon P. et al., "Cytoscape: A Software Environment for Integrated Models of Biomolecular Interaction Networks", Genome Research 13:2498-2504 (2003).
Sommer D. et al., "TALEN-Mediated Genome Engineering to Generate Targeted Mice", Chromsome Res 23:43-55 (2015).
Summerton J. et al., "Morpholino Antisense Oligomers: Design, Preparation, and Properties", Antisense & Nucleic Acid Drug Development 7:187-195 (1997).
Tian T. et al., "AgriGO v2.0: A Go Analysis Toolkit for the Agricultural Community, 2017 Update", Nucleic Acids Research 45:W122-W129 (2017).

* cited by examiner

A

B

SEQUENCE LISTING

```
<160> NUMBER OF SEQ ID NOS: 33

<210> SEQ ID NO 1
<211> LENGTH: 1557
<212> TYPE: DNA
<213> ORGANISM: Populus balsamifera subsp. trichocarpa

<400> SEQUENCE: 1

atggctcaag tgagcaaaat cagcaatgga gcacaaaaca cctacacaac aatccatctt     60

ttaaaacccc aaatacccaa atctttgtct tcaatttcat ttagatcaca gctcattaaa    120

gggtcttctt ttggtttgaa gcaatgtaaa aaaatgggta gttgcaagct aaaggttgaa    180

cctttgaagg ttttagcttc aattgctaca gcagagaagc catcaactgt acctgagatc    240

gttttgcaac ccatcaaaga tatttctggt actgttactt taccgggttc caagtctctg    300

tcaaatcgga tactccttct tgctgctctc tctgagggta cgactgttgt tgacaatttg    360

ttgaatagtg atgatgttca ttacatgctt ggcgcgctaa gaacacttgg cctacatgtg    420

gaagagaata agaaactcaa acaagcaatt gtagaaggat gtggtggcca gtttcctgtg    480

ggaaaagaag caaatgttga tgttgaactt ttccttggaa atgctggaac agcaatgcgt    540

ccattgacag ctgctgtaac tgctgcaggt ggaaattcaa gctacatact tgatggggtg    600

ccacgaatga gggagagacc aattggtgat ttggttattg gtcttcagca gcttggtgca    660

gatgtttctt gttctcctac aaactgcccc cctgttcgca taaatgcaaa tgggggcctt    720

ccagggggaa aggttaaact ctctggatct ataagtagtc aatacttgac tgctttgctc    780

atggcagctc ctttagctct tggagatgtg gaaattgaga tcgttgacaa attgatttct    840

gttccatatg ttgagatgac tctgaagttg atggagcgct atggagtctt tgtagaacac    900

agtgataact gggatcgttt ctttgttcga ggaggtcaaa agtacaagtc tcctaaaaat    960

tcttttgttg agggcgatgc ttcaagtgcc agttacttcc tagctggtgc agcaatcact   1020

ggtgggacca tcactgtcga aggttgtggg atggatagtt tgcagggaga tgtaaagttt   1080

gcagaggttc ttgagaaaat gggagccaaa gttacttgga caaagaacag tgttactgtc   1140

actggaccgc cacgagattc ttctggtcag aaacacttgc gtgctgtcga tgtaaacatg   1200

aacaaaatgc cagatgttgc tatgactctg gctgttgttg cgcttttcgc tgatggtcct   1260

actgccataa gagatgtggc aagttggaga gtgaaagaaa cagaacggat gattgctatt   1320

tgcacagaac taaggaagtt gggagcaaca gttgaagaag gaccagatta ctgtgtgatc   1380

actccacctg agaaactaaa tgtgacagag attgacactt atgatgatca caggatggca   1440
```

atggcattct ctcttgctgc ttgtggagaa gtccaagtca ccatcaagga ccctggttgc 1500
actcgaaaaa ctttcccaga ctactttgag gttcttgaga ggtacacaaa gcattga 1557

<210> SEQ ID NO 2
<211> LENGTH: 518
<212> TYPE: PRT
<213> ORGANISM: Populus balsamifera subsp. trichocarpa

<400> SEQUENCE: 2

```
Met Ala Gln Val Ser Lys Ile Ser Asn Gly Ala Gln Asn Thr Tyr Thr
1               5                   10                  15

Thr Ile His Leu Leu Lys Pro Gln Ile Pro Lys Ser Leu Ser Ser Ile
            20                  25                  30

Ser Phe Arg Ser Gln Leu Ile Lys Gly Ser Ser Phe Gly Leu Lys Gln
        35                  40                  45

Cys Lys Lys Met Gly Ser Cys Lys Leu Lys Val Glu Pro Leu Lys Val
    50                  55                  60

Leu Ala Ser Ile Ala Thr Ala Glu Lys Pro Ser Thr Val Pro Glu Ile
65                  70                  75                  80

Val Leu Gln Pro Ile Lys Asp Ile Ser Gly Thr Val Thr Leu Pro Gly
                85                  90                  95

Ser Lys Ser Leu Ser Asn Arg Ile Leu Leu Leu Ala Ala Leu Ser Glu
            100                 105                 110

Gly Thr Thr Val Val Asp Asn Leu Leu Asn Ser Asp Asp Val His Tyr
        115                 120                 125

Met Leu Gly Ala Leu Arg Thr Leu Gly Leu His Val Glu Glu Asn Lys
    130                 135                 140

Lys Leu Lys Gln Ala Ile Val Glu Gly Cys Gly Gly Gln Phe Pro Val
145                 150                 155                 160

Gly Lys Glu Ala Asn Val Asp Val Glu Leu Phe Leu Gly Asn Ala Gly
                165                 170                 175

Thr Ala Met Arg Pro Leu Thr Ala Ala Val Thr Ala Ala Gly Gly Asn
            180                 185                 190

Ser Ser Tyr Ile Leu Asp Gly Val Pro Arg Met Arg Glu Arg Pro Ile
        195                 200                 205

Gly Asp Leu Val Ile Gly Leu Gln Gln Leu Gly Ala Asp Val Ser Cys
    210                 215                 220

Ser Pro Thr Asn Cys Pro Pro Val Arg Ile Asn Ala Asn Gly Gly Leu
225                 230                 235                 240

Pro Gly Gly Lys Val Lys Leu Ser Gly Ser Ile Ser Ser Gln Tyr Leu
                245                 250                 255

Thr Ala Leu Leu Met Ala Ala Pro Leu Ala Leu Gly Asp Val Glu Ile
            260                 265                 270

Glu Ile Val Asp Lys Leu Ile Ser Val Pro Tyr Val Glu Met Thr Leu
        275                 280                 285

Lys Leu Met Glu Arg Tyr Gly Val Phe Val Glu His Ser Asp Asn Trp
    290                 295                 300

Asp Arg Phe Phe Val Arg Gly Gly Gln Lys Tyr Lys Ser Pro Lys Asn
305                 310                 315                 320

Ser Phe Val Glu Gly Asp Ala Ser Ser Ala Ser Tyr Phe Leu Ala Gly
                325                 330                 335

Ala Ala Ile Thr Gly Gly Thr Ile Thr Val Glu Gly Cys Gly Met Asp
            340                 345                 350

Ser Leu Gln Gly Asp Val Lys Phe Ala Glu Val Leu Glu Lys Met Gly
```

```
        355                 360                 365

Ala Lys Val Thr Trp Thr Lys Asn Ser Val Thr Val Thr Gly Pro Pro
    370                 375                 380

Arg Asp Ser Ser Gly Gln Lys His Leu Arg Ala Val Asp Val Asn Met
385                 390                 395                 400

Asn Lys Met Pro Asp Val Ala Met Thr Leu Ala Val Val Ala Leu Phe
                405                 410                 415

Ala Asp Gly Pro Thr Ala Ile Arg Asp Val Ala Ser Trp Arg Val Lys
            420                 425                 430

Glu Thr Glu Arg Met Ile Ala Ile Cys Thr Glu Leu Arg Lys Leu Gly
        435                 440                 445

Ala Thr Val Glu Glu Gly Pro Asp Tyr Cys Val Ile Thr Pro Pro Glu
    450                 455                 460

Lys Leu Asn Val Thr Glu Ile Asp Thr Tyr Asp Asp His Arg Met Ala
465                 470                 475                 480

Met Ala Phe Ser Leu Ala Ala Cys Gly Glu Val Gln Val Thr Ile Lys
                485                 490                 495

Asp Pro Gly Cys Thr Arg Lys Thr Phe Pro Asp Tyr Phe Glu Val Leu
            500                 505                 510

Glu Arg Tyr Thr Lys His
        515


<210> SEQ ID NO 3
<211> LENGTH: 1557
<212> TYPE: DNA
<213> ORGANISM: Populus balsamifera subsp. trichocarpa

<400> SEQUENCE: 3

atggctcaag tgagcaaaat cagcaatgga gcacaaaaca cctacacaac aatccatctt      60

ttaaaacccc aaatacccaa atctttgtct tcaatttcat ttagatcaca gctcattaaa     120

gggtcttctt ttggtttgaa gcaatgtaaa aaaatgggta gttgcaagct aaaggttgaa     180

cctttgaagg ttttagcttc aattgctaca gcagagaagc catcaactgt acctgagatc     240

gttttgcaac ccatcaaaga tatttctggt actgttactt taccgggttc caagtctctg     300

tcaaatcgga tactccttct tgctgctctc tctgagggta cgactgttgt tgacaatttg     360

ttgaatagtg atgatgttca ttacatgctt ggcgcgctaa gaacacttgg cctacatgtg     420

gaagagaata agaaactcaa acaagcaatt gtagaaggat gtggtggcca gtttcctgtg     480

ggaaaagaag caaatgttga tgttgaactt ttccttggaa atgctggaac agcaatgcgt     540

ccattgacag ctgctgtaac tgctgcaggt ggaaattcaa gctacatact tgatggggtg     600

ccacgaatga gggagagacc aattggtgat ttggttattg gtcttcagca gcttggtgca     660

gatgtttctt gttctcctac aaactgcccc cctgttcgca taaatgcaaa tgggggcctt     720

ccagggggaa aggttaaact ctctggatct ataagtagtc aatacttgac tgctttgctc     780

atggcagctc ctttagctct tggagatgtg gaaattgaga tcgttgacaa attgatttct     840

gttccatatg ttgagatgac tctgaagttg atggagcgct atggagtctt tgtagaacac     900

agtgataact gggatcgttt ctttgttcga ggaggtcaaa agtacaagtc tcctaaaaat     960

tcttttgttg agggcgatgc ttcaagtgcc agttacttcc tagctggtgc agcaatcact    1020

ggtgggacca tcactgtcga aggttgtggg atggatagtt tgcagggaga tgtaaagttt    1080

gcagaggttc ctgagaaaat gggagccaaa gttacttgga caaagaacag tgttactgtc    1140

actggaccgc cacgagattc ttctggtcag aaacacttgc gtgctgtcga tgtaaacatg    1200
```

```
aacaaaatgc cagatgttgc tatgactctg gctgttgttg cgcttttcgc tgatggtcct   1260

actgccataa gagatgtggc aagttggaga gtgaaagaaa cagaacggat gattgctatt   1320

tgcacagaac taaggaagtt gggagcaaca gttgaagaag gaccagatta ctgtgtgatc   1380

actccacctg agaaactaaa tgtgacagag attgacactt atgatgatca caggatggca   1440

atggcattct ctcttgctgc ttgtggagaa gtccaagtca ccatcaagga ccctggttgc   1500

actcgaaaaa ctttcccaga ctactttgag gttcttgaga ggtacacaaa gcattga      1557
```

```
<210> SEQ ID NO 4
<211> LENGTH: 518
<212> TYPE: PRT
<213> ORGANISM: Populus balsamifera subsp. trichocarpa

<400> SEQUENCE: 4

Met Ala Gln Val Ser Lys Ile Ser Asn Gly Ala Gln Asn Thr Tyr Thr
1               5                   10                  15

Thr Ile His Leu Leu Lys Pro Gln Ile Pro Lys Ser Leu Ser Ser Ile
            20                  25                  30

Ser Phe Arg Ser Gln Leu Ile Lys Gly Ser Ser Phe Gly Leu Lys Gln
        35                  40                  45

Cys Lys Lys Met Gly Ser Cys Lys Leu Lys Val Glu Pro Leu Lys Val
    50                  55                  60

Leu Ala Ser Ile Ala Thr Ala Glu Lys Pro Ser Thr Val Pro Glu Ile
65                  70                  75                  80

Val Leu Gln Pro Ile Lys Asp Ile Ser Gly Thr Val Thr Leu Pro Gly
                85                  90                  95

Ser Lys Ser Leu Ser Asn Arg Ile Leu Leu Leu Ala Ala Leu Ser Glu
            100                 105                 110

Gly Thr Thr Val Val Asp Asn Leu Leu Asn Ser Asp Asp Val His Tyr
        115                 120                 125

Met Leu Gly Ala Leu Arg Thr Leu Gly Leu His Val Glu Glu Asn Lys
    130                 135                 140

Lys Leu Lys Gln Ala Ile Val Glu Gly Cys Gly Gly Gln Phe Pro Val
145                 150                 155                 160

Gly Lys Glu Ala Asn Val Asp Val Glu Leu Phe Leu Gly Asn Ala Gly
                165                 170                 175

Thr Ala Met Arg Pro Leu Thr Ala Ala Val Thr Ala Ala Gly Gly Asn
            180                 185                 190

Ser Ser Tyr Ile Leu Asp Gly Val Pro Arg Met Arg Glu Arg Pro Ile
        195                 200                 205

Gly Asp Leu Val Ile Gly Leu Gln Gln Leu Gly Ala Asp Val Ser Cys
    210                 215                 220

Ser Pro Thr Asn Cys Pro Pro Val Arg Ile Asn Ala Asn Gly Gly Leu
225                 230                 235                 240

Pro Gly Gly Lys Val Lys Leu Ser Gly Ser Ile Ser Ser Gln Tyr Leu
                245                 250                 255

Thr Ala Leu Leu Met Ala Ala Pro Leu Ala Leu Gly Asp Val Glu Ile
            260                 265                 270

Glu Ile Val Asp Lys Leu Ile Ser Val Pro Tyr Val Glu Met Thr Leu
        275                 280                 285

Lys Leu Met Glu Arg Tyr Gly Val Phe Val Glu His Ser Asp Asn Trp
    290                 295                 300

Asp Arg Phe Phe Val Arg Gly Gly Gln Lys Tyr Lys Ser Pro Lys Asn
```

```
305                 310                 315                 320

Ser Phe Val Glu Gly Asp Ala Ser Ser Ala Ser Tyr Phe Leu Ala Gly
                325                 330                 335

Ala Ala Ile Thr Gly Gly Thr Ile Thr Val Glu Gly Cys Gly Met Asp
            340                 345                 350

Ser Leu Gln Gly Asp Val Lys Phe Ala Glu Val Pro Glu Lys Met Gly
        355                 360                 365

Ala Lys Val Thr Trp Thr Lys Asn Ser Val Thr Val Thr Gly Pro Pro
    370                 375                 380

Arg Asp Ser Ser Gly Gln Lys His Leu Arg Ala Val Asp Val Asn Met
385                 390                 395                 400

Asn Lys Met Pro Asp Val Ala Met Thr Leu Ala Val Val Ala Leu Phe
                405                 410                 415

Ala Asp Gly Pro Thr Ala Ile Arg Asp Val Ala Ser Trp Arg Val Lys
            420                 425                 430

Glu Thr Glu Arg Met Ile Ala Ile Cys Thr Glu Leu Arg Lys Leu Gly
        435                 440                 445

Ala Thr Val Glu Glu Gly Pro Asp Tyr Cys Val Ile Thr Pro Pro Glu
    450                 455                 460

Lys Leu Asn Val Thr Glu Ile Asp Thr Tyr Asp Asp His Arg Met Ala
465                 470                 475                 480

Met Ala Phe Ser Leu Ala Ala Cys Gly Glu Val Gln Val Thr Ile Lys
                485                 490                 495

Asp Pro Gly Cys Thr Arg Lys Thr Phe Pro Asp Tyr Phe Glu Val Leu
            500                 505                 510

Glu Arg Tyr Thr Lys His
        515


<210> SEQ ID NO 5
<211> LENGTH: 23
<212> TYPE: DNA
<213> ORGANISM: Artificial Sequence
<220> FEATURE:
<223> OTHER INFORMATION: oligonucleotide

<400> SEQUENCE: 5

gctatgactc tggctgttgt tgc                                              23


<210> SEQ ID NO 6
<211> LENGTH: 21
<212> TYPE: DNA
<213> ORGANISM: Artificial Sequence
<220> FEATURE:
<223> OTHER INFORMATION: oligonucleotide

<400> SEQUENCE: 6

caacgtgcac aacagaattg a                                                21


<210> SEQ ID NO 7
<211> LENGTH: 518
<212> TYPE: PRT
<213> ORGANISM: Populus balsamifera subsp. trichocarpa

<400> SEQUENCE: 7

Met Ala Gln Val Ser Lys Ile Ser Asn Gly Ala Gln Asn Thr Tyr Thr
1               5                   10                  15

Thr Ile His Leu Leu Lys Pro Gln Ile Pro Lys Ser Leu Ser Ser Ile
            20                  25                  30
```

```
Ser Phe Arg Ser Gln Leu Ile Lys Gly Ser Ser Phe Gly Leu Lys Gln
        35                  40                  45

Cys Lys Lys Met Gly Ser Cys Lys Leu Lys Val Glu Pro Leu Lys Val
    50                  55                  60

Leu Ala Ser Ile Ala Thr Ala Glu Lys Pro Ser Thr Val Pro Glu Ile
65                  70                  75                  80

Val Leu Gln Pro Ile Lys Asp Ile Ser Gly Thr Val Thr Leu Pro Gly
                85                  90                  95

Ser Lys Ser Leu Ser Asn Arg Ile Leu Leu Leu Ala Ala Leu Ser Glu
            100                 105                 110

Gly Thr Thr Val Val Asp Asn Leu Leu Asn Ser Asp Asp Val His Tyr
        115                 120                 125

Met Leu Gly Ala Leu Arg Thr Leu Gly Leu His Val Glu Asp Asn Lys
    130                 135                 140

Lys Leu Lys Gln Ala Ile Val Glu Gly Cys Gly Gly Gln Phe Pro Val
145                 150                 155                 160

Gly Lys Glu Ala Asn Val Asp Val Glu Leu Phe Leu Gly Asn Ala Gly
                165                 170                 175

Thr Ala Met Arg Pro Leu Thr Ala Ala Val Thr Ala Ala Gly Gly Asn
            180                 185                 190

Ser Ser Tyr Ile Leu Asp Gly Val Pro Arg Met Arg Glu Arg Pro Ile
        195                 200                 205

Gly Asp Leu Val Ile Gly Leu Gln Gln Leu Gly Ala Asp Val Ser Cys
    210                 215                 220

Ser Pro Thr Asn Cys Pro Pro Val Arg Ile Asn Ala Asn Gly Gly Leu
225                 230                 235                 240

Pro Gly Gly Lys Val Lys Leu Ser Gly Ser Ile Ser Ser Gln Tyr Leu
                245                 250                 255

Thr Ala Leu Leu Met Ala Ala Pro Leu Ala Leu Gly Asp Val Glu Ile
            260                 265                 270

Glu Ile Val Asp Lys Leu Ile Ser Val Pro Tyr Val Glu Met Thr Leu
        275                 280                 285

Lys Leu Met Glu Arg Tyr Gly Val Phe Val Glu His Ser Asp Asn Trp
    290                 295                 300

Asp Arg Phe Phe Val Arg Gly Gly Gln Lys Tyr Lys Ser Pro Lys Asn
305                 310                 315                 320

Ser Phe Val Glu Gly Asp Ala Ser Ser Ala Ser Tyr Phe Leu Ala Gly
                325                 330                 335

Ala Ala Ile Thr Gly Gly Thr Ile Thr Val Glu Gly Cys Gly Met Asp
            340                 345                 350

Ser Leu Gln Gly Asp Val Lys Phe Ala Glu Val Leu Glu Lys Met Gly
        355                 360                 365

Ala Lys Val Thr Trp Thr Lys Asn Ser Val Thr Val Thr Gly Pro Pro
    370                 375                 380

Arg Asp Ser Ser Gly Gln Lys His Leu Arg Ala Val Asp Val Asn Met
385                 390                 395                 400

Asn Lys Met Pro Asp Val Ala Met Thr Leu Ala Val Val Ala Leu Phe
                405                 410                 415

Ala Asp Gly Pro Thr Ala Ile Arg Asp Val Ala Ser Trp Arg Val Lys
            420                 425                 430

Glu Thr Glu Arg Met Ile Ala Ile Cys Thr Glu Leu Arg Lys Leu Gly
        435                 440                 445

Ala Thr Val Glu Glu Gly Pro Asp Tyr Cys Val Ile Thr Pro Pro Glu
```

```
    450                 455                 460

Lys Leu Asn Val Thr Glu Ile Asp Thr Tyr Asp Asp His Arg Met Ala
465                 470                 475                 480

Met Ala Phe Ser Leu Ala Ala Cys Gly Glu Val Gln Val Thr Ile Lys
                485                 490                 495

Asp Pro Gly Cys Thr Arg Lys Thr Phe Pro Asp Tyr Phe Glu Val Leu
            500                 505                 510

Glu Arg Tyr Thr Lys His
        515


<210> SEQ ID NO 8
<211> LENGTH: 864
<212> TYPE: DNA
<213> ORGANISM: Oryza sativa

<400> SEQUENCE: 8

atggggaggt cgccatgctg cgagaaggcg cacacgaaca agggggcgtg gacgaaggag      60

gaggaccagc ggctgatcgc ctacatcaag gcgcacggcg agggttgctg gcggtcgctg     120

cccaaggcgg cggggctcct ccgctgcggc aagagctgcc gcctccgctg gatgaactac     180

ctccgccccg acctcaagcg cggcaacttc accgacgacg acgacgagct catcatcaag     240

ctccacgccc ttctcggcaa caagtggtcg ttgattgcgg ggcagctgcc ggggaggacg     300

gacaacgaga tcaagaacta ctggaacacg cacatcaagc gcaagctcct gagccggggc     360

atcgacccgc agacgcaccg gccggtcagc gccgggagca gcgccgccgc ggcgagcggg     420

ctgaccacga cggccagcac cgccgccttt ccgtcccttg cgccggcgcc gccgccgcag     480

cagcacaggc tacacaaccc ggtgcacgcc gcggcgccga gcaatgcgag cttcgccagg     540

tccgcggcgt ccccgccgtc ggaggacggc cacagcagca gcggcggcag ctcggacgcg     600

ccgcggtgcc ccgacctcaa cctcgacctc gacctcgacc tgtccatgag cctgccgagc     660

tcgccgccca agacgccggc cgccgcgtcg tccacgaccg cgtcgcgcca ccatcaccac     720

cagcagcaga agaccatctg cctctgctac cacctcggcg tccgcaacgg cgacgtctgc     780

agctgcaagg cggccgcgcc atcgccggcc ggcccacgcg cgttccggtt tctcaggcca     840

ctggaggagg gccagtacat atag                                            864


<210> SEQ ID NO 9
<211> LENGTH: 287
<212> TYPE: PRT
<213> ORGANISM: Oryza sativa

<400> SEQUENCE: 9

Met Gly Arg Ser Pro Cys Cys Glu Lys Ala His Thr Asn Lys Gly Ala
1               5                   10                  15

Trp Thr Lys Glu Glu Asp Gln Arg Leu Ile Ala Tyr Ile Lys Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Met Asn Tyr Leu Arg Pro Asp
    50                  55                  60

Leu Lys Arg Gly Asn Phe Thr Asp Asp Asp Asp Glu Leu Ile Ile Lys
65                  70                  75                  80

Leu His Ala Leu Leu Gly Asn Lys Trp Ser Leu Ile Ala Gly Gln Leu
                85                  90                  95

Pro Gly Arg Thr Asp Asn Glu Ile Lys Asn Tyr Trp Asn Thr His Ile
```

```
            100                 105                 110

Lys Arg Lys Leu Leu Ser Arg Gly Ile Asp Pro Gln Thr His Arg Pro
        115                 120                 125

Val Ser Ala Gly Ser Ser Ala Ala Ala Ala Ser Gly Leu Thr Thr Thr
    130                 135                 140

Ala Ser Thr Ala Ala Phe Pro Ser Leu Ala Pro Ala Pro Pro Pro Gln
145                 150                 155                 160

Gln His Arg Leu His Asn Pro Val His Ala Ala Ala Pro Ser Asn Ala
                165                 170                 175

Ser Phe Ala Arg Ser Ala Ala Ser Pro Pro Ser Glu Asp Gly His Ser
            180                 185                 190

Ser Ser Gly Gly Ser Ser Asp Ala Pro Arg Cys Pro Asp Leu Asn Leu
        195                 200                 205

Asp Leu Asp Leu Asp Leu Ser Met Ser Leu Pro Ser Ser Pro Pro Lys
    210                 215                 220

Thr Pro Ala Ala Ala Ser Ser Thr Thr Ala Ser Arg His His His His
225                 230                 235                 240

Gln Gln Gln Lys Thr Ile Cys Leu Cys Tyr His Leu Gly Val Arg Asn
                245                 250                 255

Gly Asp Val Cys Ser Cys Lys Ala Ala Ala Pro Ser Pro Ala Gly Pro
            260                 265                 270

Arg Ala Phe Arg Phe Leu Arg Pro Leu Glu Glu Gly Gln Tyr Ile
        275                 280                 285


<210> SEQ ID NO 10
<211> LENGTH: 732
<212> TYPE: DNA
<213> ORGANISM: Oryza sativa

<400> SEQUENCE: 10

atggggaggt cgccgtgctg cgagaaggag cacactaaca agggcgcgtg gaccaaggag      60

gaggacgagc gcctcgtcgc ctacatccgc gcccacggcg agggctgctg gcgctcgctc     120

cccaaggccg ccggcctcct ccgctgcggc aagagctgcc gcctccgctg gatcaactac     180

ctccgccccg acctcaagcg cggcaacttc accgccgacg aggacgacct catcatcaag     240

ctccacagcc tcctcggcaa caagtggtct ctgatcgcgg cgaggctgcc ggggaggacg     300

gacaacgaga tcaagaacta ctggaacacg cacatccgcc ggaagcttct cggcaggggg     360

atcgaccccg tcacgcaccg ccccgtcaac gccgccgccg ccaccatctc cttccatccc     420

cagccgccgc caacgacgaa ggaggagcag ctcatactca gcaagccgcc caagtgcccc     480

gacctcaacc tggacctctg catcagcccg ccgtcgtgcc aggaagaaga cgatgactat     540

gaggcgaagc cggcgatgat cgtgagggcg ccggagctgc agcgccgccg cggcggcctc     600

tgcttcggct gcagcctcgg cctccagaag gagtgcaagt gcagcggcgg cggcgccggc     660

gccggcgccg gcaacaactt cctcggcctc agggctggca tgctcgactt cagaagcctc     720

cccatgaaat ga                                                         732


<210> SEQ ID NO 11
<211> LENGTH: 243
<212> TYPE: PRT
<213> ORGANISM: Oryza sativa

<400> SEQUENCE: 11

Met Gly Arg Ser Pro Cys Cys Glu Lys Glu His Thr Asn Lys Gly Ala
1               5                   10                  15
```

```
Trp Thr Lys Glu Glu Asp Glu Arg Leu Val Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Ala Asp Glu Asp Asp Leu Ile Ile Lys
65                  70                  75                  80

Leu His Ser Leu Leu Gly Asn Lys Trp Ser Leu Ile Ala Ala Arg Leu
                85                  90                  95

Pro Gly Arg Thr Asp Asn Glu Ile Lys Asn Tyr Trp Asn Thr His Ile
            100                 105                 110

Arg Arg Lys Leu Leu Gly Arg Gly Ile Asp Pro Val Thr His Arg Pro
        115                 120                 125

Val Asn Ala Ala Ala Ala Thr Ile Ser Phe His Pro Gln Pro Pro Pro
    130                 135                 140

Thr Thr Lys Glu Glu Gln Leu Ile Leu Ser Lys Pro Pro Lys Cys Pro
145                 150                 155                 160

Asp Leu Asn Leu Asp Leu Cys Ile Ser Pro Pro Ser Cys Gln Glu Glu
                165                 170                 175

Asp Asp Asp Tyr Glu Ala Lys Pro Ala Met Ile Val Arg Ala Pro Glu
            180                 185                 190

Leu Gln Arg Arg Arg Gly Gly Leu Cys Phe Gly Cys Ser Leu Gly Leu
        195                 200                 205

Gln Lys Glu Cys Lys Cys Ser Gly Gly Gly Ala Gly Ala Gly Ala Gly
    210                 215                 220

Asn Asn Phe Leu Gly Leu Arg Ala Gly Met Leu Asp Phe Arg Ser Leu
225                 230                 235                 240

Pro Met Lys
```

<210> SEQ ID NO 12
<211> LENGTH: 801
<212> TYPE: DNA
<213> ORGANISM: Oryza sativa

<400> SEQUENCE: 12

```
atggggaggt cgccgtgctg cgagaaggcg cacacgaaca agggcgcgtg gaccaaggag     60

gaggaccagc gcctcatcgc ccacatcaac cagcacggcg agggctgctg gaggtcgctc    120

cccaaggccg ccgggttgct gcgttgcggg aagagctgcc gcctccggtg gatcaactac    180

ctccgccccg acctcaagcg cggcaacttc accgacgagg aagacgagct catcatcaag    240

ctccacgagc tcctcggcaa caagtggtcg ctgatcgccg ggaggctgcc ggggaggacg    300

gacaacgaga tcaagaacta ctggaacacc cacatcaagc gcaagctcct cgcccgcggc    360

ctcgacccgc tcacgcaccg cccgctcaat gccgccgccg ccgtcgccgg ccaccaccac    420

ctcgccgccg gcggctccag ctgctcgccc gacgcaacaa gcggccacag cagctgcagc    480

gacggcgacg agtaccgcgg cggcatcgac ctcaacctgt ccataagccc gccgtcgtcg    540

tcgtcccagc cgtcttcccc gccgccgccg ccgcacgaag cagaggcgag acgcgccgga    600

gcgacggcga gctacaccta ccaccaccac tactcggaga cgagggagaa gatatgcctg    660

tgcttgaacc acctcgggct gcacggcggc gacgagtgca gctgcggcgg ctcgtcggcc    720

tcttcctcct cctcgccgcc gccggcgacg gcgagctcgc gagcgttcac attcgccaat    780
```

```
gcatcgtcgt caacagtgta a                                                801


<210> SEQ ID NO 13
<211> LENGTH: 266
<212> TYPE: PRT
<213> ORGANISM: Oryza sativa

<400> SEQUENCE: 13

Met Gly Arg Ser Pro Cys Cys Glu Lys Ala His Thr Asn Lys Gly Ala
1               5                   10                  15

Trp Thr Lys Glu Glu Asp Gln Arg Leu Ile Ala His Ile Asn Gln His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Asp Glu Glu Asp Glu Leu Ile Ile Lys
65                  70                  75                  80

Leu His Glu Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Lys Arg Lys Leu Leu Ala Arg Gly Leu Asp Pro Leu Thr His Arg Pro
        115                 120                 125

Leu Asn Ala Ala Ala Ala Val Ala Gly His His His Leu Ala Ala Gly
    130                 135                 140

Gly Ser Ser Cys Ser Pro Asp Ala Thr Ser Gly His Ser Ser Cys Ser
145                 150                 155                 160

Asp Gly Asp Glu Tyr Arg Gly Gly Ile Asp Leu Asn Leu Ser Ile Ser
                165                 170                 175

Pro Pro Ser Ser Ser Ser Gln Pro Ser Ser Pro Pro Pro Pro Pro His
            180                 185                 190

Glu Ala Glu Ala Arg Arg Ala Gly Ala Thr Ala Ser Tyr Thr Tyr His
        195                 200                 205

His His Tyr Ser Glu Thr Arg Glu Lys Ile Cys Leu Cys Leu Asn His
    210                 215                 220

Leu Gly Leu His Gly Gly Asp Glu Cys Ser Cys Gly Gly Ser Ser Ala
225                 230                 235                 240

Ser Ser Ser Ser Ser Pro Pro Pro Ala Thr Ala Ser Ser Arg Ala Phe
                245                 250                 255

Thr Phe Ala Asn Ala Ser Ser Ser Thr Val
            260                 265


<210> SEQ ID NO 14
<211> LENGTH: 783
<212> TYPE: DNA
<213> ORGANISM: Oryza sativa

<400> SEQUENCE: 14

atggggaggt cgccgtgctg cgagaaggcg cacacgaaca agggggcgtg gacgaaggag      60

gaggaccagc ggctcatcgc gtacatcagg gcgcatggcg aaggctgctg gcgctcgctg     120

cccaaggcgg cgggcctcct tcgctgcggc aagagctgcc gcctccggtg gatgaactac     180

ctccgccccg acctcaagcg cggcaacttc accgacgacg aggacgagct catcatccgc     240

ctccacagcc tcctcggcaa caagtggtct ctgatcgccg ggcagctgcc ggggaggacg     300
```

```
gacaacgaga tcaagaacta ctggaacacg cacatcaagc gcaagctcct cgcccgcggc    360

atcgacccgc agacgcaccg cccgctgctc agcggcggtg acggcatcgc ggcgagcaac    420

aaggcggcac caccgccgcc gcatcccata tccgtcccgg cgaaggcggc ggccgcggcg    480

atcttcgccg tggcgaagcc gccgccgccg ccgcgcccgg tcgactcctc ggacgacggc    540

tgccgcagca gcagcggcac aacgagcacg gggagccgc ggtgccccga cctcaacctc    600

gagctctcgg tcgggccgac gccgagctcg ccgccggcgg agacgcccac cagcgcgcgg    660

ccggtctgcc tctgctacca cctcggcttc cgcggcgggg aggcgtgcag ctgtcaggct    720

gacagcaagg gcccacacga gtttagatat ttcaggccgt tggaacaagg ccagtacata    780

tga                                                                  783
```

<210> SEQ ID NO 15
<211> LENGTH: 260
<212> TYPE: PRT
<213> ORGANISM: Oryza sativa

<400> SEQUENCE: 15

```
Met Gly Arg Ser Pro Cys Cys Glu Lys Ala His Thr Asn Lys Gly Ala
1               5                   10                  15

Trp Thr Lys Glu Glu Asp Gln Arg Leu Ile Ala Tyr Ile Arg Ala His
            20                  25                  30

Gly Glu Gly Cys Trp Arg Ser Leu Pro Lys Ala Ala Gly Leu Leu Arg
        35                  40                  45

Cys Gly Lys Ser Cys Arg Leu Arg Trp Met Asn Tyr Leu Arg Pro Asp
    50                  55                  60

Leu Lys Arg Gly Asn Phe Thr Asp Asp Glu Asp Glu Leu Ile Ile Arg
65                  70                  75                  80

Leu His Ser Leu Leu Gly Asn Lys Trp Ser Leu Ile Ala Gly Gln Leu
                85                  90                  95

Pro Gly Arg Thr Asp Asn Glu Ile Lys Asn Tyr Trp Asn Thr His Ile
            100                 105                 110

Lys Arg Lys Leu Leu Ala Arg Gly Ile Asp Pro Gln Thr His Arg Pro
        115                 120                 125

Leu Leu Ser Gly Gly Asp Gly Ile Ala Ala Ser Asn Lys Ala Ala Pro
    130                 135                 140

Pro Pro Pro His Pro Ile Ser Val Pro Ala Lys Ala Ala Ala Ala Ala
145                 150                 155                 160

Ile Phe Ala Val Ala Lys Pro Pro Pro Pro Pro Arg Pro Val Asp Ser
                165                 170                 175

Ser Asp Asp Gly Cys Arg Ser Ser Ser Gly Thr Thr Ser Thr Gly Glu
            180                 185                 190

Pro Arg Cys Pro Asp Leu Asn Leu Glu Leu Ser Val Gly Pro Thr Pro
        195                 200                 205

Ser Ser Pro Pro Ala Glu Thr Pro Thr Ser Ala Arg Pro Val Cys Leu
    210                 215                 220

Cys Tyr His Leu Gly Phe Arg Gly Gly Glu Ala Cys Ser Cys Gln Ala
225                 230                 235                 240

Asp Ser Lys Gly Pro His Glu Phe Arg Tyr Phe Arg Pro Leu Glu Gln
                245                 250                 255

Gly Gln Tyr Ile
            260
```

<210> SEQ ID NO 16

<211> LENGTH: 1023
<212> TYPE: DNA
<213> ORGANISM: Oryza sativa

<400> SEQUENCE: 16

```
atggggaggg gacgagcgcc gtgctgcgcc aaggtggggc tgaacagggg ttcgtggacg      60
ccgcaggagg acatgcggct catcgcctac atccagaagc acggccacgc caactggcga     120
gccctcccca agcaggccgg attgctgcgg tgcggcaaga gctgccgcct ccggtggatc     180
aactacctgc gccccgacct gaagcgcggc aacttcaccg ccgacgagga ggacaccatc     240
atcaagctgc acggcctact cgggaacaag tggtccaaga tcgcgtcgtg cctgcccggg     300
aggacggaca acgagatcaa gaacgtgtgg aacacccacc tgaagaagag ggtgtcgcag     360
agagagaagc caggtgacac caagaagaag ggcaaggccg cggacgccag cgacgacgcc     420
gacgcgcatt ccccgtcgtc gtcggcgtcc tcctcgacga cgacggcggc caataacaac     480
aacagcggcg acacggccgg cgagcagtgc ggcacgagca aggagcccga gaacgtcgac     540
gtgtccttct tcgagcaaga catcgacatc tcggacatgc tggtggacgc gcccacggag     600
gcgccgctgg tcgcggcgcc aatgccgccg tccccgtgct cgtcgtcctc cctgacgacg     660
acgacgtgcg tcggcgccgt gtcggacgag ctgctcgacc tgccggagat cgacatcgag     720
ccggatatat ggagcatcat cgacggctac ggcggcgatg agcccggcga cggcgatgca     780
acagtgccat gtaccgccag cccgggagag gagggagcag agtggtgggt agagaatttg     840
gagaaggagc tcggcctgtg gggggcccatg gacgagtccc tggcccatcc ggacccaccc     900
ggacaggttt gttacccggg cccactcacg gaaacagagg gggacccagt ctccacctac     960
ttccagtccg ggcccaccgc ctctccgctc caggagatcg catcacccgc cgttctctca    1020
tga                                                                  1023
```

<210> SEQ ID NO 17
<211> LENGTH: 340
<212> TYPE: PRT
<213> ORGANISM: Oryza sativa

<400> SEQUENCE: 17

```
Met Gly Arg Gly Arg Ala Pro Cys Cys Ala Lys Val Gly Leu Asn Arg
1               5                   10                  15

Gly Ser Trp Thr Pro Gln Glu Asp Met Arg Leu Ile Ala Tyr Ile Gln
            20                  25                  30

Lys His Gly His Ala Asn Trp Arg Ala Leu Pro Lys Gln Ala Gly Leu
        35                  40                  45

Leu Arg Cys Gly Lys Ser Cys Arg Leu Arg Trp Ile Asn Tyr Leu Arg
    50                  55                  60

Pro Asp Leu Lys Arg Gly Asn Phe Thr Ala Asp Glu Glu Asp Thr Ile
65                  70                  75                  80

Ile Lys Leu His Gly Leu Leu Gly Asn Lys Trp Ser Lys Ile Ala Ser
                85                  90                  95

Cys Leu Pro Gly Arg Thr Asp Asn Glu Ile Lys Asn Val Trp Asn Thr
            100                 105                 110

His Leu Lys Lys Arg Val Ser Gln Arg Glu Lys Pro Gly Asp Thr Lys
        115                 120                 125

Lys Lys Gly Lys Ala Ala Asp Ala Ser Asp Asp Ala Asp Ala His Ser
    130                 135                 140

Pro Ser Ser Ser Ala Ser Ser Ser Thr Thr Thr Ala Ala Asn Asn Asn
145                 150                 155                 160
```

```
Asn Ser Gly Asp Thr Ala Gly Glu Gln Cys Gly Thr Ser Lys Glu Pro
                165                 170                 175

Glu Asn Val Asp Val Ser Phe Phe Glu Gln Asp Ile Asp Ile Ser Asp
            180                 185                 190

Met Leu Val Asp Ala Pro Thr Glu Ala Pro Leu Val Ala Ala Pro Met
        195                 200                 205

Pro Pro Ser Pro Cys Ser Ser Ser Ser Leu Thr Thr Thr Thr Cys Val
    210                 215                 220

Gly Ala Val Ser Asp Glu Leu Leu Asp Leu Pro Glu Ile Asp Ile Glu
225                 230                 235                 240

Pro Asp Ile Trp Ser Ile Ile Asp Gly Tyr Gly Gly Asp Glu Pro Gly
                245                 250                 255

Asp Gly Asp Ala Thr Val Pro Cys Thr Ala Ser Pro Gly Glu Glu Gly
            260                 265                 270

Ala Glu Trp Trp Val Glu Asn Leu Glu Lys Glu Leu Gly Leu Trp Gly
        275                 280                 285

Pro Met Asp Glu Ser Leu Ala His Pro Asp Pro Pro Gly Gln Val Cys
    290                 295                 300

Tyr Pro Gly Pro Leu Thr Glu Thr Glu Gly Asp Pro Val Ser Thr Tyr
305                 310                 315                 320

Phe Gln Ser Gly Pro Thr Ala Ser Pro Leu Gln Glu Ile Ala Ser Pro
                325                 330                 335

Ala Val Leu Ser
            340


<210> SEQ ID NO 18
<211> LENGTH: 945
<212> TYPE: DNA
<213> ORGANISM: Oryza sativa

<400> SEQUENCE: 18

atgacgtggt gcaacagctt cagcgacgtc cgcaccgccg tggacagcag cttgtcgccg      60

gccgccgccg tggccgccgc cgcggggaag aaggcggcgg cgtcgctcgc cgtcctcgtc     120

aagatgtgcc cctcctgcgg ccaccgcgcg cggtatgaac aggagacgac gacgatccag     180

gacctgccgg ggctgccggc cggagtgaag ttcgatccga cggaccagga gcttcttgag     240

catttggaag ggaaggcgag gccggactcg aggaagctcc accctctcgt cgacgagttc     300

atccccacca tcgagggcga gaatggcatc tgctacaccc atcccgagag gcttcccggt     360

gtgagcaagg acgggctggt gaggcacttc ttccaccggc cgtcgaaggc gtacacgacg     420

gggacgagga agcggcggaa ggtgcacagc gacgaggtcg acggcggcga gacgcggtgg     480

cacaagaccg gcaagacgag accggtgatg gccaacggcc ggcccagggg ctacaagaag     540

atcctcgtcc tctacaccaa ctacggcaag cagcgcaagc cggagaagac caactgggtg     600

atgcaccagt accacctcgg ctccgacgag gaggagcggg acggcgagct cgtcgtctcc     660

aaggtcttct tccagacgca gcccaggcag tgcggctcca ccgccgccgc cgccgccgcc     720

aaggaggcct ccgccgccgt cgccgccgcc gtggtgaaca gcaactactc catcgtccat     780

ggccatcaag gtggtggtgg tggtagcttt ctcaaggagg caaacgttgt gcacgagttc     840

tacgacccgg cagcaacgat gggttaccgg ccacctgctc ctgctgcgca cttcgcgcca     900

aacttcgcgg tgcacgcggc aaggaacagc tttggtggcc cttga                     945


<210> SEQ ID NO 19
```

```
<211> LENGTH: 314
<212> TYPE: PRT
<213> ORGANISM: Oryza sativa

<400> SEQUENCE: 19

Met Thr Trp Cys Asn Ser Phe Ser Asp Val Arg Thr Ala Val Asp Ser
1               5                   10                  15

Ser Leu Ser Pro Ala Ala Ala Val Ala Ala Ala Ala Gly Lys Lys Ala
            20                  25                  30

Ala Ala Ser Leu Ala Val Leu Val Lys Met Cys Pro Ser Cys Gly His
        35                  40                  45

Arg Ala Arg Tyr Glu Gln Glu Thr Thr Thr Ile Gln Asp Leu Pro Gly
    50                  55                  60

Leu Pro Ala Gly Val Lys Phe Asp Pro Thr Asp Gln Glu Leu Leu Glu
65                  70                  75                  80

His Leu Glu Gly Lys Ala Arg Pro Asp Ser Arg Lys Leu His Pro Leu
                85                  90                  95

Val Asp Glu Phe Ile Pro Thr Ile Glu Gly Glu Asn Gly Ile Cys Tyr
            100                 105                 110

Thr His Pro Glu Arg Leu Pro Gly Val Ser Lys Asp Gly Leu Val Arg
        115                 120                 125

His Phe Phe His Arg Pro Ser Lys Ala Tyr Thr Thr Gly Thr Arg Lys
    130                 135                 140

Arg Arg Lys Val His Ser Asp Glu Val Asp Gly Gly Glu Thr Arg Trp
145                 150                 155                 160

His Lys Thr Gly Lys Thr Arg Pro Val Met Ala Asn Gly Arg Pro Arg
                165                 170                 175

Gly Tyr Lys Lys Ile Leu Val Leu Tyr Thr Asn Tyr Gly Lys Gln Arg
            180                 185                 190

Lys Pro Glu Lys Thr Asn Trp Val Met His Gln Tyr His Leu Gly Ser
        195                 200                 205

Asp Glu Glu Glu Arg Asp Gly Glu Leu Val Val Ser Lys Val Phe Phe
    210                 215                 220

Gln Thr Gln Pro Arg Gln Cys Gly Ser Thr Ala Ala Ala Ala Ala Ala
225                 230                 235                 240

Lys Glu Ala Ser Ala Ala Val Ala Ala Ala Val Val Asn Ser Asn Tyr
                245                 250                 255

Ser Ile Val His Gly His Gln Gly Gly Gly Gly Gly Ser Phe Leu Lys
            260                 265                 270

Glu Ala Asn Val Val His Glu Phe Tyr Asp Pro Ala Ala Thr Met Gly
        275                 280                 285

Tyr Arg Pro Pro Ala Pro Ala Ala His Phe Ala Pro Asn Phe Ala Val
    290                 295                 300

His Ala Ala Arg Asn Ser Phe Gly Gly Pro
305                 310


<210> SEQ ID NO 20
<211> LENGTH: 687
<212> TYPE: DNA
<213> ORGANISM: Oryza sativa

<400> SEQUENCE: 20

atggcggcgg aggcggcctc cggtggcggt ggtgggtacc ggatgctgcc gcaggcgggg      60

ttgccgatcg gtttccggtt ccgacccacc gacgaggagc tcctgctcca ctacctccgc     120

cgcaaggtca tgtcgcgccc cctccccgcc gacgtcatcc ccgtcgccga cctcgcccgc     180
```

```
ctccatccat gggaccttcc aggcgaggga gacggcgaga ggtacttctt ccacctgccg    240

gcgacgagct gctggcggag gggcggcggc gggagcaggg cgggcggcgg cggcggcgcg    300

tggagggcgt ccgggaagga gaagctcgtc gtcgcgccgc gctgcggcaa gcggcccgtc    360

ggcgccaagc ggacgctcgt cttcttccgc cgcggcggcg cccgcaccga ctgggccatg    420

cacgagtacc gcctcctccc cgccgacgac catccgccgg aggccaacga cgtctgggtg    480

gtctgccgcg tattcaagaa gaccaccacg ctggctcacc gccgttcgcc gccgtccatc    540

cgtggcgcgc cacgccggcg agccgccgcc gccgacgacg acgacatgcc gtcctcgccg    600

tcgtcctgcg tgacggacgg cggcgacgcg ggggaggagg gagaagagag cagcagctgc    660

agcgtcgtcg cttctaattg tccatga                                        687
```

<210> SEQ ID NO 21
<211> LENGTH: 228
<212> TYPE: PRT
<213> ORGANISM: Oryza sativa

<400> SEQUENCE: 21

```
Met Ala Ala Glu Ala Ala Ser Gly Gly Gly Gly Gly Tyr Arg Met Leu
1               5                   10                  15

Pro Gln Ala Gly Leu Pro Ile Gly Phe Arg Phe Arg Pro Thr Asp Glu
            20                  25                  30

Glu Leu Leu Leu His Tyr Leu Arg Arg Lys Val Met Ser Arg Pro Leu
        35                  40                  45

Pro Ala Asp Val Ile Pro Val Ala Asp Leu Ala Arg Leu His Pro Trp
    50                  55                  60

Asp Leu Pro Gly Glu Gly Asp Gly Glu Arg Tyr Phe Phe His Leu Pro
65                  70                  75                  80

Ala Thr Ser Cys Trp Arg Arg Gly Gly Gly Gly Ser Arg Ala Gly Gly
                85                  90                  95

Gly Gly Gly Ala Trp Arg Ala Ser Gly Lys Glu Lys Leu Val Val Ala
            100                 105                 110

Pro Arg Cys Gly Lys Arg Pro Val Gly Ala Lys Arg Thr Leu Val Phe
        115                 120                 125

Phe Arg Arg Gly Gly Ala Arg Thr Asp Trp Ala Met His Glu Tyr Arg
    130                 135                 140

Leu Leu Pro Ala Asp Asp His Pro Pro Glu Ala Asn Asp Val Trp Val
145                 150                 155                 160

Val Cys Arg Val Phe Lys Lys Thr Thr Thr Leu Ala His Arg Arg Ser
                165                 170                 175

Pro Pro Ser Ile Arg Gly Ala Pro Arg Arg Arg Ala Ala Ala Ala Asp
            180                 185                 190

Asp Asp Asp Met Pro Ser Ser Pro Ser Ser Cys Val Thr Asp Gly Gly
        195                 200                 205

Asp Ala Gly Glu Glu Gly Glu Glu Ser Ser Ser Cys Ser Val Val Ala
    210                 215                 220

Ser Asn Cys Pro
225
```

<210> SEQ ID NO 22
<211> LENGTH: 783
<212> TYPE: DNA
<213> ORGANISM: Oryza sativa

<400> SEQUENCE: 22

```
atggagacga cggcggcgaa gaagctgccg ccggggttca ggttcaggcc caccgacgag     60

gagcttgtgg tgcactacct ccgccgccgc gcgctcggct cccctctccc gcccgccgtc    120

gacatccccg atgtccgcct cctcgcgcat gacccctccg acctgcttcc tccagggtgg    180

agtgagcagg agaggtactt cttcacgtgc aaggaggcca agtatgtcaa ggggcgccgc    240

gccaaccgcg ccacgggcgc cgggtactgg aaggcgacgg ggaaggagaa gccggtggcg    300

gtgtccgtgg cggcggcgcc gaggagccag gccgccgccg tcgtcgtcgg catgaagcgc    360

tccctcgtgt tctaccgcgg gaagccgccg accggcaaga agacggactg ggtcatgcac    420

gagtaccgcc tcgccggcgc cggcctcgcc ccgtgccgcc gcgccgccac cgccgaccac    480

ccggcgcgcc ccgccgaggg ctgggtgctc tgccgcgtgt tccggaagaa aggctccgcg    540

gccgcgtcga cagccagccc caccgccgac gccgacgacg acgacgccac cacggagcgc    600

gccgacgacg ccgcggcggg cgtccggttc atcgacttct tcgcccgcgc cgacgcgcgg    660

cggcgccgcg cggcgtcgcc ggtgtcgtcg agctgcgtga cggatgcgtc ggcggagcat    720

tgcagggagc aggagacgac gagccggaac ggcggcgccg ccgccggcga cgcctccgac    780

taa                                                                  783
```

<210> SEQ ID NO 23
<211> LENGTH: 260
<212> TYPE: PRT
<213> ORGANISM: Oryza sativa

<400> SEQUENCE: 23

```
Met Glu Thr Thr Ala Ala Lys Lys Leu Pro Pro Gly Phe Arg Phe Arg
1               5                   10                  15

Pro Thr Asp Glu Glu Leu Val Val His Tyr Leu Arg Arg Arg Ala Leu
            20                  25                  30

Gly Ser Pro Leu Pro Pro Ala Val Asp Ile Pro Asp Val Arg Leu Leu
        35                  40                  45

Ala His Asp Pro Ser Asp Leu Leu Pro Pro Gly Trp Ser Glu Gln Glu
    50                  55                  60

Arg Tyr Phe Phe Thr Cys Lys Glu Ala Lys Tyr Val Lys Gly Arg Arg
65                  70                  75                  80

Ala Asn Arg Ala Thr Gly Ala Gly Tyr Trp Lys Ala Thr Gly Lys Glu
                85                  90                  95

Lys Pro Val Ala Val Ser Val Ala Ala Ala Pro Arg Ser Gln Ala Ala
            100                 105                 110

Ala Val Val Val Gly Met Lys Arg Ser Leu Val Phe Tyr Arg Gly Lys
        115                 120                 125

Pro Pro Thr Gly Lys Lys Thr Asp Trp Val Met His Glu Tyr Arg Leu
    130                 135                 140

Ala Gly Ala Gly Leu Ala Pro Cys Arg Arg Ala Ala Thr Ala Asp His
145                 150                 155                 160

Pro Ala Arg Pro Ala Glu Gly Trp Val Leu Cys Arg Val Phe Arg Lys
                165                 170                 175

Lys Gly Ser Ala Ala Ala Ser Thr Ala Ser Pro Thr Ala Asp Ala Asp
            180                 185                 190

Asp Asp Asp Ala Thr Thr Glu Arg Ala Asp Asp Ala Ala Ala Gly Val
        195                 200                 205

Arg Phe Ile Asp Phe Phe Ala Arg Ala Asp Ala Arg Arg Arg Arg Ala
    210                 215                 220
```

```
Ala Ser Pro Val Ser Ser Ser Cys Val Thr Asp Ala Ser Ala Glu His
225                 230                 235                 240

Cys Arg Glu Gln Glu Thr Thr Ser Arg Asn Gly Gly Ala Ala Ala Gly
                245                 250                 255

Asp Ala Ser Asp
            260


<210> SEQ ID NO 24
<211> LENGTH: 615
<212> TYPE: DNA
<213> ORGANISM: Oryza sativa

<400> SEQUENCE: 24

atgggaggag ctacaaactt acctccaggt ttccacttct tcccctcgga tgaagagctc      60

gtcgtccatt tcctccgtcg caaggtctcc ctcctcccat gccaccctga catcatcccg     120

acgctgcttc cgcatcggta caatccatgg gagctgaatg gcaaagcact gcaagctggg     180

aaccagtggt acttcttctg ccatctaaca caaagtagga cctcatccaa tgggcactgg     240

agccccattg gagttgatga aacagtaaga agcggcggcc gcaatgttgg cttgaagaaa     300

acgctgctat tctccattgg agagccctct gaaggcatca gaaccaactg gatcatgcat     360

gagtaccatc tgctagacgg ggattgcgtc gctggcggta gcagcaactt gactagctcg     420

agctctaaca ggaggtctca taggaagaga ggccactcaa gcatggagtc caacaactgg     480

gtgctgtgcc gagtgttcga atcgagctgc ggttcacaag tgagcttcca cggtgagggc     540

accgagcttt catgcttaga tgaggtgttt ttgtcactag atgactacga tgaagtaagt     600

ttgccgaata aatag                                                      615


<210> SEQ ID NO 25
<211> LENGTH: 204
<212> TYPE: PRT
<213> ORGANISM: Oryza sativa

<400> SEQUENCE: 25

Met Gly Gly Ala Thr Asn Leu Pro Pro Gly Phe His Phe Phe Pro Ser
1               5                   10                  15

Asp Glu Glu Leu Val Val His Phe Leu Arg Arg Lys Val Ser Leu Leu
            20                  25                  30

Pro Cys His Pro Asp Ile Ile Pro Thr Leu Leu Pro His Arg Tyr Asn
        35                  40                  45

Pro Trp Glu Leu Asn Gly Lys Ala Leu Gln Ala Gly Asn Gln Trp Tyr
    50                  55                  60

Phe Phe Cys His Leu Thr Gln Ser Arg Thr Ser Ser Asn Gly His Trp
65                  70                  75                  80

Ser Pro Ile Gly Val Asp Glu Thr Val Arg Ser Gly Gly Arg Asn Val
                85                  90                  95

Gly Leu Lys Lys Thr Leu Leu Phe Ser Ile Gly Glu Pro Ser Glu Gly
            100                 105                 110

Ile Arg Thr Asn Trp Ile Met His Glu Tyr His Leu Leu Asp Gly Asp
        115                 120                 125

Cys Val Ala Gly Gly Ser Ser Asn Leu Thr Ser Ser Ser Ser Asn Arg
    130                 135                 140

Arg Ser His Arg Lys Arg Gly His Ser Ser Met Glu Ser Asn Asn Trp
145                 150                 155                 160

Val Leu Cys Arg Val Phe Glu Ser Ser Cys Gly Ser Gln Val Ser Phe
                165                 170                 175
```

```
His Gly Glu Gly Thr Glu Leu Ser Cys Leu Asp Glu Val Phe Leu Ser
            180                 185                 190

Leu Asp Asp Tyr Asp Glu Val Ser Leu Pro Asn Lys
        195                 200


<210> SEQ ID NO 26
<211> LENGTH: 831
<212> TYPE: DNA
<213> ORGANISM: Oryza sativa

<400> SEQUENCE: 26

atggtggtgg ccggcaagaa gcagggacgg cattcttttt ctgcatcatc atcgtcgtct      60

tcgtcttctt cttgttcagt agtgcagctg ggtcatcatc agcgcccaca gggtgaggac     120

cctctcatcg gcatcaaagc agcagcagca ggaggaggag gaataatgag aaagggcccg     180

tggacggagc aggaggacgt gcagttggtt tggttcgtgc ggctgctggg cgaacggcgg     240

tgggatttct tagcaaaggt gtcaggtttg cagcgcagcg ggaagagctg ccgtctccgg     300

tgggtgaact acctgcatcc agggctgaag cgagggagga tgagccccga ggaggagagg     360

atggtggtgc agctccacgc caagctcggc aacaggtggt ctcgcatcgc caagagcatt     420

cctggccgca ccgacaacga gatcaagaac tactggcgca cccacctgcg caagctcaag     480

ctcaaacagc aaaagcagca gcagtccgac gaccaccaca acgacaacga cgacgacgac     540

gaccgcaact cctcctcctc ttcgtcctcc tccaacagca acagcaacct gcagcagcag     600

ccgcagccag aggatgagtc gtcggccagt ggcagcctgc aggcccaaca tcatgaggac     660

cagcaccaac tgttccttca tcctctctgg aacgacgaca tcatcgtcga cgtcgactgc     720

tggagcagca gcaccaacgt cgtcgctccg ccgccgatgc ccgcctcgcc gctctgggat     780

atcgatgacg ccttcttctg ctcggattat tcgctacctc tctggggata g              831


<210> SEQ ID NO 27
<211> LENGTH: 276
<212> TYPE: PRT
<213> ORGANISM: Oryza sativa

<400> SEQUENCE: 27

Met Val Val Ala Gly Lys Lys Gln Gly Arg His Ser Phe Ser Ala Ser
1               5                   10                  15

Ser Ser Ser Ser Ser Ser Ser Ser Cys Ser Val Val Gln Leu Gly His
            20                  25                  30

His Gln Arg Pro Gln Gly Glu Asp Pro Leu Ile Gly Ile Lys Ala Ala
        35                  40                  45

Ala Ala Gly Gly Gly Gly Ile Met Arg Lys Gly Pro Trp Thr Glu Gln
    50                  55                  60

Glu Asp Val Gln Leu Val Trp Phe Val Arg Leu Leu Gly Glu Arg Arg
65                  70                  75                  80

Trp Asp Phe Leu Ala Lys Val Ser Gly Leu Gln Arg Ser Gly Lys Ser
                85                  90                  95

Cys Arg Leu Arg Trp Val Asn Tyr Leu His Pro Gly Leu Lys Arg Gly
            100                 105                 110

Arg Met Ser Pro Glu Glu Glu Arg Met Val Val Gln Leu His Ala Lys
        115                 120                 125

Leu Gly Asn Arg Trp Ser Arg Ile Ala Lys Ser Ile Pro Gly Arg Thr
    130                 135                 140

Asp Asn Glu Ile Lys Asn Tyr Trp Arg Thr His Leu Arg Lys Leu Lys
```

```
145                 150                 155                 160

Leu Lys Gln Gln Lys Gln Gln Gln Ser Asp Asp His His Asn Asp Asn
                165                 170                 175

Asp Asp Asp Asp Asp Arg Asn Ser Ser Ser Ser Ser Ser Ser Ser Asn
            180                 185                 190

Ser Asn Ser Asn Leu Gln Gln Gln Pro Gln Pro Glu Asp Glu Ser Ser
        195                 200                 205

Ala Ser Gly Ser Leu Gln Ala Gln His His Glu Asp Gln His Gln Leu
    210                 215                 220

Phe Leu His Pro Leu Trp Asn Asp Asp Ile Ile Val Asp Val Asp Cys
225                 230                 235                 240

Trp Ser Ser Ser Thr Asn Val Val Ala Pro Pro Pro Met Pro Ala Ser
                245                 250                 255

Pro Leu Trp Asp Ile Asp Asp Ala Phe Phe Cys Ser Asp Tyr Ser Leu
            260                 265                 270

Pro Leu Trp Gly
        275


<210> SEQ ID NO 28
<211> LENGTH: 2538
<212> TYPE: DNA
<213> ORGANISM: Oryza sativa

<400> SEQUENCE: 28

atgtcttcag tcatgatgac aagcgacaac ggaaaggctc cagagaaggg tggagaagct     60

tctggacctt catcagctcc ccaagaaggt gaaatcagca atgaaccaca aaggcgccgg    120

ccgctcagtg ggaggaccac tggtccaaca cggcgttcca cgaaaggaaa ttggacccct    180

gaagaggatt ccatattgtc cagagctgtt cagacatata aagggaagaa ttggaaaaaa    240

atagcggaat gttttccgga tagaaccgat gtacaatgct tgcacaggtg gcaaaaggtt    300

ctaaaccctg aattggtcaa agggccatgg tccaaagaag aagatgacat cattgttcag    360

atggtaaaca aacttggacc aaagaaatgg tcaaccattg ctcaagcttt gcctggacgt    420

ataggaaagc aatgtcggga acggtggcac aaccatctta accctggcat aaacaaggag    480

gcatggacac aagaagagga aattaccctc atacatgctc atcgaatgta tggaaataaa    540

tgggctgagc tgacaaaatt tttaccagga aggacggaca atgcaattaa aaatcactgg    600

aacagttcag taaagaagaa agtcgactca tacatgtcat caggtttact tacccaagtc    660

tcgtgtctcc ctctaaatga atactctgca cactgtaatt cctcacctgc gttgacccaa    720

caaaacagcg aagacagtgg tagctatgct gttcgagagg ttgaaaattc atcagtgtgt    780

agtcaatcat cacttgccaa ggtttcttgc tcccaagtgc acaatgctaa tgtggcattg    840

ggctgtgatt tgcaagtaaa tgcgaatgtt gacaataatg aagcgcatga ttctcaatct    900

tctgtgggtc acgaagcatg ctatacttct gtgggggctg ttgcaactgc tatacctgag    960

gtgcactacc acgtttcttc ctctaacttc gatccagatc aacacttgca agaggagttt   1020

gctcaaggat tgaatttgca tatgagtatg gatgaagtgc caagtaattc tagttttgca   1080

gacaacccaa ctatctgtag tatagaaaat catgaaaggt cattggaacc atatgatgta   1140

gcaatggaga tgcctctctc tatgttacca agtgattctg gagctgagca aaaactacat   1200

tttatgtcgg aggctgactt caatagtcct aattgtctga aatctgaact ttggcaggat   1260

atttccttgc aaagccttct ttctggacct gatgcagttg aaactgattc tttttcaaga   1320

tcaaatcatc aatcggatgt atattcctct caagcagata atgaattttt agcaccaccc   1380
```

```
tacctattac agacatcaaa ttcttccagt gtgatggagg ctacttatgg acagagtcca   1440

cagatgtcag taccaccatc tcttatctgt tcaaatgtta tgactgatgt accttctgat   1500

aatagatcag aaccaaaaga aatgacagtt tctcaggcag aaatggtcac acaatcttcc   1560

agttcttcag gtgacgctga aatgtctgct aaccctggta gtagtaatgg cagtgatatt   1620

ccttcaatga tggaaaggat acctgaatgt gcggaccaac atgttactaa tgcggaagaa   1680

cctgaagcca gtatagagaa agaaccatcg gttacaccga gtgctacagc agatgaaaag   1740

caggatgagg gagccctatt ctatgaacct cctcgttttc caagcatgga tgttccattt   1800

gtcagttgcg accttgtaac ttctggtgat ctccaagagt atagtcccct tggtattcgg   1860

cagttaatgc ggtcgaccat gaatgtctgc actccaatga gattgtgggg ctcccctaca   1920

catgatgaaa gccctgacat tttgctgaag agtgctgcca aaagcttcat atgcacacca   1980

tcaatactaa agaaacgtca cagagacctc gtgtctccta ttccggataa aagaatcgag   2040

aagaaatctg ggactgaaaa ggattgtggg gtatcagaca catcctccat cggcattcaa   2100

acatgtttta ttaatgccac taaagatgat gctgttataa ctaaatcagt tttgcgtatt   2160

gagcgatctg cttcttctaa acctctggaa aagaaacttg agttctctga tgagaacaag   2220

gaaaatttgg acaacacaat tgaacaggca aaagatggac agagtgcagg aaattacaaa   2280

cacattgacg agcaggcaag gggggaacgg cgtactgcaa caaatataac tactacttat   2340

gatgatctgc caggcaattt acaacctgca ggtattctta ttgagcacaa cggtgatgat   2400

cttgtttccc cagattatgg taaaaacacc atgaacagaa gcaaaaacaca aatatggaat   2460

ctttgtcagt ctgtaaggag ggagtgtctg ctaaaaagcc tgcggaactt attgtggaga   2520

aatcttcagc atgcataa                                                 2538
```

```
<210> SEQ ID NO 29
<211> LENGTH: 845
<212> TYPE: PRT
<213> ORGANISM: Oryza sativa

<400> SEQUENCE: 29

Met Ser Ser Val Met Met Thr Ser Asp Asn Gly Lys Ala Pro Glu Lys
1               5                   10                  15

Gly Gly Glu Ala Ser Gly Pro Ser Ser Ala Pro Gln Glu Gly Glu Ile
            20                  25                  30

Ser Asn Glu Pro Gln Arg Arg Arg Pro Leu Ser Gly Arg Thr Thr Gly
        35                  40                  45

Pro Thr Arg Arg Ser Thr Lys Gly Asn Trp Thr Pro Glu Glu Asp Ser
    50                  55                  60

Ile Leu Ser Arg Ala Val Gln Thr Tyr Lys Gly Lys Asn Trp Lys Lys
65                  70                  75                  80

Ile Ala Glu Cys Phe Pro Asp Arg Thr Asp Val Gln Cys Leu His Arg
                85                  90                  95

Trp Gln Lys Val Leu Asn Pro Glu Leu Val Lys Gly Pro Trp Ser Lys
            100                 105                 110

Glu Glu Asp Asp Ile Ile Val Gln Met Val Asn Lys Leu Gly Pro Lys
        115                 120                 125

Lys Trp Ser Thr Ile Ala Gln Ala Leu Pro Gly Arg Ile Gly Lys Gln
    130                 135                 140

Cys Arg Glu Arg Trp His Asn His Leu Asn Pro Gly Ile Asn Lys Glu
145                 150                 155                 160
```

```
Ala Trp Thr Gln Glu Glu Glu Ile Thr Leu Ile His Ala His Arg Met
                165                 170                 175

Tyr Gly Asn Lys Trp Ala Glu Leu Thr Lys Phe Leu Pro Gly Arg Thr
            180                 185                 190

Asp Asn Ala Ile Lys Asn His Trp Asn Ser Ser Val Lys Lys Lys Val
        195                 200                 205

Asp Ser Tyr Met Ser Ser Gly Leu Leu Thr Gln Val Ser Cys Leu Pro
    210                 215                 220

Leu Asn Glu Tyr Ser Ala His Cys Asn Ser Ser Pro Ala Leu Thr Gln
225                 230                 235                 240

Gln Asn Ser Glu Asp Ser Gly Ser Tyr Ala Val Arg Glu Val Glu Asn
                245                 250                 255

Ser Ser Val Cys Ser Gln Ser Ser Leu Ala Lys Val Ser Cys Ser Gln
            260                 265                 270

Val His Asn Ala Asn Val Ala Leu Gly Cys Asp Leu Gln Val Asn Ala
        275                 280                 285

Asn Val Asp Asn Asn Glu Ala His Asp Ser Gln Ser Ser Val Gly His
    290                 295                 300

Glu Ala Cys Tyr Thr Ser Val Gly Ala Val Ala Thr Ala Ile Pro Glu
305                 310                 315                 320

Val His Tyr His Val Ser Ser Ser Asn Phe Asp Pro Asp Gln His Leu
                325                 330                 335

Gln Glu Glu Phe Ala Gln Gly Leu Asn Leu His Met Ser Met Asp Glu
            340                 345                 350

Val Pro Ser Asn Ser Ser Phe Ala Asp Asn Pro Thr Ile Cys Ser Ile
        355                 360                 365

Glu Asn His Glu Arg Ser Leu Glu Pro Tyr Asp Val Ala Met Glu Met
    370                 375                 380

Pro Leu Ser Met Leu Pro Ser Asp Ser Gly Ala Glu Gln Lys Leu His
385                 390                 395                 400

Phe Met Ser Glu Ala Asp Phe Asn Ser Pro Asn Cys Leu Lys Ser Glu
                405                 410                 415

Leu Trp Gln Asp Ile Ser Leu Gln Ser Leu Leu Ser Gly Pro Asp Ala
            420                 425                 430

Val Glu Thr Asp Ser Phe Ser Arg Ser Asn His Gln Ser Asp Val Tyr
        435                 440                 445

Ser Ser Gln Ala Asp Asn Glu Phe Leu Ala Pro Pro Tyr Leu Leu Gln
    450                 455                 460

Thr Ser Asn Ser Ser Ser Val Met Glu Ala Thr Tyr Gly Gln Ser Pro
465                 470                 475                 480

Gln Met Ser Val Pro Pro Ser Leu Ile Cys Ser Asn Val Met Thr Asp
                485                 490                 495

Val Pro Ser Asp Asn Arg Ser Glu Pro Lys Glu Met Thr Val Ser Gln
            500                 505                 510

Ala Glu Met Val Thr Gln Ser Ser Ser Ser Ser Gly Asp Ala Glu Met
        515                 520                 525

Ser Ala Asn Pro Gly Ser Ser Asn Gly Ser Asp Ile Pro Ser Met Met
    530                 535                 540

Glu Arg Ile Pro Glu Cys Ala Asp Gln His Val Thr Asn Ala Glu Glu
545                 550                 555                 560

Pro Glu Ala Ser Ile Glu Lys Glu Pro Ser Val Thr Pro Ser Ala Thr
                565                 570                 575

Ala Asp Glu Lys Gln Asp Glu Gly Ala Leu Phe Tyr Glu Pro Pro Arg
```

```
            580                 585                 590

Phe Pro Ser Met Asp Val Pro Phe Val Ser Cys Asp Leu Val Thr Ser
        595                 600                 605

Gly Asp Leu Gln Glu Tyr Ser Pro Leu Gly Ile Arg Gln Leu Met Arg
    610                 615                 620

Ser Thr Met Asn Val Cys Thr Pro Met Arg Leu Trp Gly Ser Pro Thr
625                 630                 635                 640

His Asp Glu Ser Pro Asp Ile Leu Leu Lys Ser Ala Ala Lys Ser Phe
                645                 650                 655

Ile Cys Thr Pro Ser Ile Leu Lys Lys Arg His Arg Asp Leu Val Ser
            660                 665                 670

Pro Ile Pro Asp Lys Arg Ile Glu Lys Lys Ser Gly Thr Glu Lys Asp
        675                 680                 685

Cys Gly Val Ser Asp Thr Ser Ser Ile Gly Ile Gln Thr Cys Phe Ile
    690                 695                 700

Asn Ala Thr Lys Asp Asp Ala Val Ile Thr Lys Ser Val Leu Arg Ile
705                 710                 715                 720

Glu Arg Ser Ala Ser Ser Lys Pro Leu Glu Lys Lys Leu Glu Phe Ser
                725                 730                 735

Asp Glu Asn Lys Glu Asn Leu Asp Asn Thr Ile Glu Gln Ala Lys Asp
            740                 745                 750

Gly Gln Ser Ala Gly Asn Tyr Lys His Ile Asp Glu Gln Ala Arg Gly
        755                 760                 765

Glu Arg Arg Thr Ala Thr Asn Ile Thr Thr Thr Tyr Asp Asp Leu Pro
    770                 775                 780

Gly Asn Leu Gln Pro Ala Gly Ile Leu Ile Glu His Asn Gly Asp Asp
785                 790                 795                 800

Leu Val Ser Pro Asp Tyr Gly Lys Asn Thr Met Asn Arg Ser Lys Thr
                805                 810                 815

Gln Ile Trp Asn Leu Cys Gln Ser Val Arg Arg Glu Cys Leu Leu Lys
            820                 825                 830

Ser Leu Arg Asn Leu Leu Trp Arg Asn Leu Gln His Ala
        835                 840                 845
```

<210> SEQ ID NO 30
<211> LENGTH: 1767
<212> TYPE: DNA
<213> ORGANISM: Oryza sativa

<400> SEQUENCE: 30

```
atgggcgcga tgccggcggt gaaggtggag gaggaggagg aggagcggaa tccggtggcg     60

tcgagccctt cggtctcgga ggggagcgcg cacgccgccg cgctggcgtc gcccaccgcg    120

gcggattcca tcttcggtcg caggcgaaaa agtggcccgg taaggagagc taagggtggc    180

tggacaccag aagaggatga aaaattgcgg aaggcagttg atatttataa tggcaaaaac    240

tggaagaaga tagaagtaca atgtctgcat agatggcaga aagttcttga tcctgaactt    300

ataaaaggtc catggaccca agaggaagat gatgtcatca tcaatatggt aaagaagcat    360

ggaccaaaaa aatggtctgt tatagcaagg tcactaaatg gtcgaattgg taaacaatgc    420

cgagagaggt ggcataatca tttggaccca caaataagga aagaagcttg gactgttgaa    480

gaggagcgtg tgcttgcccg tgctcattgt atgtatggga ataaatgggc agaaattgct    540

aaacttcttc ctggaaggac agacaattct ataaaaaacc attggaacag ttcattaaga    600

aaaaaaatag atgactacaa taccagagat attctgccag ttcatccacc agttgttggt    660
```

```
gatggtttga aacagttacc aaagcggcca cctgctgaca accattttga cttaaacaaa    720

gagccaatta tctgttcaag agaccgctta ggagtagttc attctgaccc tacctctcat    780

caacgggcat ccaatttgaa agactttaag ggctgtgcag attacctctc acttggtcag    840

ccagtaactt catgtgaggc ttctgcagct gatgattctg cttttgatct agcaacacag    900

ggaatgagaa tggattctgt tcatgacaag ggtactggga acaattttgt ttgtgggaag    960

gttcagggaa tcaattttct tggtgacaag ggacttaaaa ttaatcagat atcagataaa   1020

atgggctgtt caagacaagc taagagagaa ggtgaagcag ccattaatgg cggcggatca   1080

tccttgcaga gtgaggctca ctctgttggt tctctttgtt atcagatacc taagatggaa   1140

gacattgctc ctgcccaatc cccagtgttt acagcaaatt atgtaccgga acactctagg   1200

aacgtaatgc actcacccaa tggctatact actccaccca ctcatggaaa aggatcagat   1260

cagcttagtg ttgaatccat attgagaagt gctgctgaaa aattccatgg tactccctca   1320

atactaagaa gaagaaaaag agataaaccg acgcctgctg aagataatga tttgaagatt   1380

ggcagattaa gcagtgatga cttccacact cccataggaa agtgtactac agatagccca   1440

cagtcattca aaactgcagc acttttgtcc ttgggtccta tggatgagca agggagtctt   1500

gatgtttccc ctccatatcg actaaggtca aaaagattgg ctgtcctgaa aactgttcaa   1560

aatcatctgg atttttcatc tgatgaaatg agcatttgtg atactacaat gaaatctgcc   1620

tgcgggaatt ctgattgtgc taatgccagt agtggtgttt caagcattca agggaagaaa   1680

ctggatgagc atatgattgg attggaaact ttaaccatga actttgcgca tacgacaaag   1740

ttggatgcta cccaacctaa tttgtag                                       1767

<210> SEQ ID NO 31
<211> LENGTH: 588
<212> TYPE: PRT
<213> ORGANISM: Oryza sativa

<400> SEQUENCE: 31

Met Gly Ala Met Pro Ala Val Lys Val Glu Glu Glu Glu Glu Glu Arg
1               5                   10                  15

Asn Pro Val Ala Ser Ser Pro Ser Val Ser Glu Gly Ser Ala His Ala
            20                  25                  30

Ala Ala Leu Ala Ser Pro Thr Ala Ala Asp Ser Ile Phe Gly Arg Arg
        35                  40                  45

Arg Lys Ser Gly Pro Val Arg Arg Ala Lys Gly Gly Trp Thr Pro Glu
    50                  55                  60

Glu Asp Glu Lys Leu Arg Lys Ala Val Asp Ile Tyr Asn Gly Lys Asn
65                  70                  75                  80

Trp Lys Lys Ile Glu Val Gln Cys Leu His Arg Trp Gln Lys Val Leu
                85                  90                  95

Asp Pro Glu Leu Ile Lys Gly Pro Trp Thr Gln Glu Glu Asp Asp Val
            100                 105                 110

Ile Ile Asn Met Val Lys Lys His Gly Pro Lys Lys Trp Ser Val Ile
        115                 120                 125

Ala Arg Ser Leu Asn Gly Arg Ile Gly Lys Gln Cys Arg Glu Arg Trp
    130                 135                 140

His Asn His Leu Asp Pro Gln Ile Arg Lys Glu Ala Trp Thr Val Glu
145                 150                 155                 160

Glu Glu Arg Val Leu Ala Arg Ala His Cys Met Tyr Gly Asn Lys Trp
                165                 170                 175
```

```
Ala Glu Ile Ala Lys Leu Leu Pro Gly Arg Thr Asp Asn Ser Ile Lys
            180                 185                 190

Asn His Trp Asn Ser Ser Leu Arg Lys Lys Ile Asp Asp Tyr Asn Thr
        195                 200                 205

Arg Asp Ile Leu Pro Val His Pro Pro Val Val Gly Asp Gly Leu Lys
    210                 215                 220

Gln Leu Pro Lys Arg Pro Pro Ala Asp Asn His Phe Asp Leu Asn Lys
225                 230                 235                 240

Glu Pro Ile Ile Cys Ser Arg Asp Arg Leu Gly Val Val His Ser Asp
                245                 250                 255

Pro Thr Ser His Gln Arg Ala Ser Asn Leu Lys Asp Phe Lys Gly Cys
            260                 265                 270

Ala Asp Tyr Leu Ser Leu Gly Gln Pro Val Thr Ser Cys Glu Ala Ser
        275                 280                 285

Ala Ala Asp Asp Ser Ala Phe Asp Leu Ala Thr Gln Gly Met Arg Met
    290                 295                 300

Asp Ser Val His Asp Lys Gly Thr Gly Asn Asn Phe Val Cys Gly Lys
305                 310                 315                 320

Val Gln Gly Ile Asn Phe Leu Gly Asp Lys Gly Leu Lys Ile Asn Gln
                325                 330                 335

Ile Ser Asp Lys Met Gly Cys Ser Arg Gln Ala Lys Arg Glu Gly Glu
            340                 345                 350

Ala Ala Ile Asn Gly Gly Gly Ser Ser Leu Gln Ser Glu Ala His Ser
        355                 360                 365

Val Gly Ser Leu Cys Tyr Gln Ile Pro Lys Met Glu Asp Ile Ala Pro
    370                 375                 380

Ala Gln Ser Pro Val Phe Thr Ala Asn Tyr Val Pro Glu His Ser Arg
385                 390                 395                 400

Asn Val Met His Ser Pro Asn Gly Tyr Thr Thr Pro Pro Thr His Gly
                405                 410                 415

Lys Gly Ser Asp Gln Leu Ser Val Glu Ser Ile Leu Arg Ser Ala Ala
            420                 425                 430

Glu Lys Phe His Gly Thr Pro Ser Ile Leu Arg Arg Arg Lys Arg Asp
        435                 440                 445

Lys Pro Thr Pro Ala Glu Asp Asn Asp Leu Lys Ile Gly Arg Leu Ser
    450                 455                 460

Ser Asp Asp Phe His Thr Pro Ile Gly Lys Cys Thr Thr Asp Ser Pro
465                 470                 475                 480

Gln Ser Phe Lys Thr Ala Ala Leu Leu Ser Leu Gly Pro Met Asp Glu
                485                 490                 495

Gln Gly Ser Leu Asp Val Ser Pro Pro Tyr Arg Leu Arg Ser Lys Arg
            500                 505                 510

Leu Ala Val Leu Lys Thr Val Gln Asn His Leu Asp Phe Ser Ser Asp
        515                 520                 525

Glu Met Ser Ile Cys Asp Thr Thr Met Lys Ser Ala Cys Gly Asn Ser
    530                 535                 540

Asp Cys Ala Asn Ala Ser Ser Gly Val Ser Ser Ile Gln Gly Lys Lys
545                 550                 555                 560

Leu Asp Glu His Met Ile Gly Leu Glu Thr Leu Thr Met Asn Phe Ala
                565                 570                 575

His Thr Thr Lys Leu Asp Ala Thr Gln Pro Asn Leu
            580                 585
```

<210> SEQ ID NO 32
<211> LENGTH: 1176
<212> TYPE: DNA
<213> ORGANISM: Oryza sativa

<400> SEQUENCE: 32

```
atgccgagca gcggcggcgc catgcctgcc cttccaccag gcttccgctt ccacccccacc     60

gacgaggagc tcatcgttca ctacctcatg aaccaggccg cctccgtcaa gtgccccgtg    120

ccaatcatcg ccgaggtcaa catctacaag tgcaacccat gggaccttcc tggtaaggct    180

ttgttcggcg agaacgaatg gtacttcttc agcccgaggg accgcaagta ccccaacggc    240

gctcgcccca accgcgccgc cggctcgggg tactggaagg ccaccggcac cgacaagtcc    300

atcctctcca ctccgaccag cgacaacatc ggcgtcaaga aggccctcgt cttctacaag    360

ggcaagcctc ccaagggcgt caagaccgac tggatcatgc acgagtaccg tctcaccggc    420

acatcagcta acagcaccac caccacaaag cagcgtagag cgtcatccat gaccatgagg    480

ctggacgact gggtgctgtg cagaatccac aagaagagca acgacttcaa ttcctctgac    540

caacacgacc aagaacccga ggaatcaacc gtcgaacagc ttgaagacat ccatgacaac    600

aactcctctg aacaacctcc agctccagct gacatgaaca accaacagtc agatttccag    660

cccatgacgg cgatgagcat gagcaagtca tgctccctca ccgatctcct caacaccatc    720

gactgcgccg cgctctcgca gtttctcctc gacggctcat ccgacgccat cgctgagcct    780

cctgctcctc ccagcccccct aatatacaca acacctcatc caaattacca aacactaaac    840

tataacatta acagcaacag cagcatgcca cacgccttcg agtcacgcct agatcatcac    900

gatggttacg ttaacaatta taatgttaat ggcctgagga ggaagagaat gatggcgtgt    960

agtgcaactt cctttgatga tggcagcagc agcaatgact ttgtgcatgc cgttgtcaag   1020

aaaccgcagc tgctgccaag tgattcgagg ggtagtggtt ttggaggagg ttactgcaac   1080

cagcagcttt cagagactgc gactggcttt cagtttcaga acggcaatct gctgagccat   1140

ccatttcctc tgaacaatca tctgcagatg cagtag                             1176
```

<210> SEQ ID NO 33
<211> LENGTH: 391
<212> TYPE: PRT
<213> ORGANISM: Oryza sativa

<400> SEQUENCE: 33

```
Met Pro Ser Ser Gly Gly Ala Met Pro Ala Leu Pro Pro Gly Phe Arg
1               5                   10                  15

Phe His Pro Thr Asp Glu Glu Leu Ile Val His Tyr Leu Met Asn Gln
            20                  25                  30

Ala Ala Ser Val Lys Cys Pro Val Pro Ile Ile Ala Glu Val Asn Ile
        35                  40                  45

Tyr Lys Cys Asn Pro Trp Asp Leu Pro Gly Lys Ala Leu Phe Gly Glu
    50                  55                  60

Asn Glu Trp Tyr Phe Phe Ser Pro Arg Asp Arg Lys Tyr Pro Asn Gly
65                  70                  75                  80

Ala Arg Pro Asn Arg Ala Ala Gly Ser Gly Tyr Trp Lys Ala Thr Gly
                85                  90                  95

Thr Asp Lys Ser Ile Leu Ser Thr Pro Thr Ser Asp Asn Ile Gly Val
            100                 105                 110

Lys Lys Ala Leu Val Phe Tyr Lys Gly Lys Pro Pro Lys Gly Val Lys
        115                 120                 125
```

```
Thr Asp Trp Ile Met His Glu Tyr Arg Leu Thr Gly Thr Ser Ala Asn
    130                 135                 140

Ser Thr Thr Thr Thr Lys Gln Arg Arg Ala Ser Ser Met Thr Met Arg
145                 150                 155                 160

Leu Asp Asp Trp Val Leu Cys Arg Ile His Lys Lys Ser Asn Asp Phe
                165                 170                 175

Asn Ser Ser Asp Gln His Asp Gln Glu Pro Glu Glu Ser Thr Val Glu
            180                 185                 190

Gln Leu Glu Asp Ile His Asp Asn Asn Ser Ser Glu Gln Pro Pro Ala
        195                 200                 205

Pro Ala Asp Met Asn Asn Gln Gln Ser Asp Phe Gln Pro Met Thr Ala
    210                 215                 220

Met Ser Met Ser Lys Ser Cys Ser Leu Thr Asp Leu Leu Asn Thr Ile
225                 230                 235                 240

Asp Cys Ala Ala Leu Ser Gln Phe Leu Leu Asp Gly Ser Ser Asp Ala
                245                 250                 255

Ile Ala Glu Pro Pro Ala Pro Pro Ser Pro Leu Ile Tyr Thr Thr Pro
            260                 265                 270

His Pro Asn Tyr Gln Thr Leu Asn Tyr Asn Ile Asn Ser Asn Ser Ser
        275                 280                 285

Met Pro His Ala Phe Glu Ser Arg Leu Asp His His Asp Gly Tyr Val
    290                 295                 300

Asn Asn Tyr Asn Val Asn Gly Leu Arg Arg Lys Arg Met Met Ala Cys
305                 310                 315                 320

Ser Ala Thr Ser Phe Asp Asp Gly Ser Ser Ser Asn Asp Phe Val His
                325                 330                 335

Ala Val Val Lys Lys Pro Gln Leu Leu Pro Ser Asp Ser Arg Gly Ser
            340                 345                 350

Gly Phe Gly Gly Gly Tyr Cys Asn Gln Gln Leu Ser Glu Thr Ala Thr
        355                 360                 365

Gly Phe Gln Phe Gln Asn Gly Asn Leu Leu Ser His Pro Phe Pro Leu
    370                 375                 380

Asn Asn His Leu Gln Met Gln
385                 390
```

LOSS OF FUNCTION ALLELES OF PTEPSP-TF AND ITS REGULATORY TARGETS IN RICE

STATEMENT REGARDING FEDERALLY SPONSORED RESEARCH OR DEVELOPMENT

This disclosure was made with government support under a research project supported by Contract No. DE-AC05-00OR22725 awarded by the U.S. Department of Energy. The government has certain rights in this disclosure.

INCORPORATION BY REFERENCE OF SEQUENCE LISTING

The Sequence Listing in the ASCII text file, named as 37357_3892_SEQ_ST25.txt of 75 KB and created on Jun. 17, 2019, and submitted to the United States Patent and Trademark Office via EFS-Web, is incorporated herein by reference.

BACKGROUND

In plants, the phenylpropanoid pathway is responsible for the synthesis of secondary metabolites, including lignin monomers, flavonoids, and coumarins, which play essential roles in determining plant structure, biomass recalcitrance, and stress tolerance (Vogt., (2010). *Molecular plant* 3, 2-20). Thus, a comprehensive understanding of the phenylpropanoid pathway and its regulation in rice can lead to more sustainable agriculture and energy.

In plants, the phenylpropanoid pathway is catalyzed by a set of enzymes (Xie et al., (2018a). *Frontiers in plant science* 9, 1427). Phenylalanine ammonia-lyase (PAL), cinnamate 4-hydroxylase (C4H), and 4-coumarate: CoA ligase (4CL) catalyze the first three steps of the general phenylpropanoid pathway to convert phenylalanine into p-coumaroyl-CoA, which serves as the precursor for phenylpropanoids. Downstream of 4CL, quinate/shikimate p-hydroxycinnamoyltransferase (HCT), p-coumaroylshikimate 3'-hydroxylase (C3'H), caffeoyl shikimate esterase (CSE), caffeic acid O-methyltransferase (COMT), and caffeoyl-CoA O-methyltransferase (CCoAOMT) are involved in the remaining steps of the general phenylpropanoid pathway and the biosynthesis of lignin monomers. In addition, enzymes, including cinnamoyl-CoA reductase (CCR), ferulate 5-hydroxylase (F5H), and cinnamyl alcohol dehydrogenase (CAD), specifically catalyze the biosynthesis of lignin monomers.

The phenylpropanoid pathway is tightly regulated by a transcriptional regulatory hierarchy to ensure precise spatial and temporal deposition of phenolics in plant cells. In *Arabidopsis* and grasses (e.g. rice), several MYB transcription factors directly target phenylpropanoid biosynthetic genes via binding to AC elements, which widely exist in the promoters of major phenylpropanoid pathway genes (e.g. PAL, C4H, 4CL, C3H, HCT, CCoAOMT, CCR, F5H, CAD) (Rogers and Campbell., (2004). *New phytologist* 164, 17-30). MYB46 and its paralog MYB83 activate the expression of phenylpropanoid biosynthetic genes, as well as other MYBs (Zhong et al., (2011). *Plant Cell Physiol* 52, 1856-1871; Zhong and Ye., (2012). *Plant Cell Physiol* 53, 368-380; Kim et al., (2014). *Plant molecular biology* 85, 589-599). In rice, the overexpression of OsMYB46 was shown to up-regulate the expression of 4CL, MYB58, MYB63, and MYB85 (Zhong, R., et al., (2011). *Plant Cell Physiol* 52, 1856-1871). Downstream of MYB46/83, clades of MYBs, such as MYB58/63, MYB42/85, and MYB4/32, are also involved in the regulation of the phenylpropanoid pathway (Rao, X., and Dixon, R. A. (2018). *Front Plant Sci* 9, 399). In rice, overexpression of OsMYB58/63 or OsMYB42/85 resulted in the up-regulation of the expression of one CAD gene and lignin biosynthesis (Hirano, K., et al., (2013a). *Plant and Cell Physiology* 54, 1791-1802). In *Arabidopsis*, genes in the MYB4/32 clade (e.g. AtMYB4, AtMYB32, and AtMYB7) are proposed to negatively regulate the phenylpropanoid pathway via suppressing the expression of C4H and 4CL genes (Jin, H., et al., (2000). *The EMBO journal* 19, 6150-6161; Preston, J., et al., (2004). *The Plant Journal* 40, 979-995; Fornalé, S., et al., (2014). *Plant and Cell Physiology* 55, 507-516). However, rice Osmyb4, one member of MYB4 family, was shown to activate the expression of PAL gene and the phenylpropanoid pathway in *Arabidopsis, Nicotiana tabacum*, and *Salvia sclarea* (V annini, C., et al., (2004). *The Plant Journal* 37, 115-127; Docimo, T. et al., (2008). *Planta Medica* 74, PG87), suggesting that MYB4/32 genes in grasses may be involved in different regulatory mechanisms to fine-tune the phenylpropanoid flux. Upstream of MYB46/83, a group of NAC transcription factors, called secondary wall-associated NACs (SWNs), function as master switches for the phenylpropanoid pathway and secondary cell wall biosynthesis (Rao, X., and Dixon, R. A. (2018). *Front Plant Sci,* 9, 399). The promoter of OsMYB46 contains secondary wall NAC-binding elements (SNBEs) and is directly activated by OsSWNs (Zhong, R., et al., (2011). *Plant Cell Physiol,* 52, 1856-1871). Besides OsMYB46, overexpression of OsSWNs was able to up-regulate the expression of SND3, MYB83, MYB85, MYB58, MYB63, etc (Zhong, R., et al., (2011). *Plant Cell Physiol,* 52, 1856-1871). Furthermore, the existence of feed-forward and feed-back regulations, as well as the continual discovery of new transcription factors (e.g. WRKY12, E2Fc, etc.) in the transcriptional regulatory hierarchy (Xie, M., et al., (2018a). *Frontiers in plant science* 9, 1427), demonstrate the complexity of the transcriptional regulation of the phenylpropanoid pathway.

5-enolpyruvylshikimate 3-phosphate (EPSP) synthase widely exists in plants, bacteria, and fungi. EPSP synthase has carboxyvinyl transferase activity and catalyzes the conversion of phosphoenolpyruvate and shikimate-3-phosphate to EPSP in the shikimate pathway, which is responsible for the biosynthesis of aromatic amino acids (Maeda, H., and Dudareva, N., (2012). *Annual review of plant biology* 63, 73-105). Recently, the inventors discovered one isoform of EPSP synthase in *Populus* (PtrEPSP-TF) that is involved in the regulation of the phenylpropanoid pathway. Besides the EPSP synthase activity, PtrEPSP-TF has transcriptional activity and regulates the expression of PtrMYB021 (Xie, M., et al., (2018b). *The Plant Cell* 30, 1645-1660), one functional homolog of MYB46 in *Populus* (Wilkins, O., et al., (2009). *Plant Physiology* 149, 981-993; Zhong, R., et al., (2013). *PLoS One* 8, e69219).

Genome-wide association studies (GWAS) have been conducted using interspecific mapping of populations to identify genomic regions associated with cell wall phenotypes linked to recalcitrance. *Populus* genotypes showing significant reduced lignin content have been identified.

Studies of molecular mechanisms behind phenotype changes are critical to understand the functional consequences of loci found by genome-wide association studies and to discover reliable biomarkers and effective strategies for screening genotypes with less cell wall recalcitrance and enhanced glucose release and ethanol yield, which will have great commercial value for biofuel production. Less cell wall recalcitrance is also desirable for increasing the nutritional quality of forage crops used as animal feed.

Flowering plants can be divided into two major groups, Dicots and Monocots. Dicots and monocots have major morphological differences in flower, leaf, stem, and secondary growth, suggesting some biological mechanisms may have huge variations among them. *Populus* belongs to Dicot group. While monocot plants contain some important food crops such as maize and rice.

Rice (*Oryza sativa*) is currently one of the most important cultivated crops in the world, which feeds about half of the human population. Meanwhile, with the production of approximately 1,140 million tons per year world-wide, the lignocellulosic biomass derived from rice straws has emerged as an attractive renewable feedstock for biofuels (Satlewal et al., 2018. *Biofuels, Bioproducts and Biorefining* 12, 83-107).

Identification and manipulation of genes regulating cell wall biosynthesis and recalcitrance is critical both for efficient production of cellulosic sugars and ethanol from plant biomass, and for production of improved cellulose-based products, such as paper and pulp.

BRIEF SUMMARY OF THE DISCLOSURE

One aspect of this disclosure is directed to a genetically modified plant, plant cell or plant tissue, the genetic modification comprising (a) a mutation to an endogenous PtrEPSP-TF gene, or a homolog thereof; or (b) a transcription factor that is regulated by PtrEPSP-TF, wherein the expression of the transcription factor is altered.

Another aspect of this disclosure is directed to a method comprising: (a) introducing in a plant a mutation to the endogenous transcription factor PtrEPSP-TF, or a homolog thereof, wherein the mutated PtrEPSP-TF lacks DNA binding activity; or (b) modulating in a plant the expression of a transcription factor that is regulated by PtrEPSP-TF.

In some embodiments, the mutation results in loss of DNA binding activity of the PtrEPSP-TF protein and the mutant PtrEPSP-TF gene has at least 90% sequence homology to SEQ ID NO: 1 or the mutant PtrEPSP-TF protein has at least 90% sequence homology to SEQ ID NO: 2.

In some embodiments, the mutant PtrEPSP-TF comprises a mutation at a position that is analogous to the amino acid 142 or amino acid 364 of SEQ ID NO: 7, resulting in reduced lignin content in the plant, plant cell or plant tissue.

In some embodiments, the mutation is introduced by genome editing, which is achieved by a method selected from the group consisting of CRISPR/Cas system, Cre/Lox system, TALEN system, ZFNs system and homologous recombination.

In some embodiments, the CRISPR/Cas system comprises introducing into the plant a first nucleic acid encoding a Cas9 or Cas12 nuclease, a second nucleic acid comprising a guide RNA (gRNA), and a third nucleic acid comprising a homologous repair template of a PtrEPSP-TF gene comprising at least one mutation in the PtrEPSP-TF gene sequence that results in loss of DNA binding activity.

In some embodiments, the transcription factor that is regulated by PtrEPSP-TF is selected from the group consisting of MYB4, MYB58, SND2, and VIN2, and wherein the alteration comprises inactivation of the selected transcription factor in the plant, resulting in reduced lignin content in the plant, plant cell or plant tissue.

In some embodiments, the inactivation of the selected gene is achieved by introducing a nucleic acid inhibitor of the selected gene to the plant, plant cell or plant tissue.

In some embodiments, the nucleic acid inhibitor is selected from the group consisting of an antisense RNA, a small interfering RNA, an RNAi, a microRNA, an artificial microRNA, and a ribozyme.

In some embodiments, the inactivation of the selected gene is achieved by genome editing, which is achieved by a method selected from the group consisting of CRISPR/Cas system, Cre/Lox system, TALEN system, ZFNs system and homologous recombination.

In some embodiments, the CRISPR-mediated genome editing comprises introducing into the plant a first nucleic acid encoding a Cas9 nuclease, a second nucleic acid comprising a guide RNA (gRNA), wherein said gRNA is specific to the selected gene.

In some embodiments, the transcription factor that is regulated by PtrEPSP-TF is selected from the group consisting of XND1, MYB48, MYB3R1, MYB3R3, and NAC047, and wherein the modulation comprises expressing in the plant, plant cell or plant tissue an exogenous nucleic acid comprising the selected gene, resulting in reduced lignin content in the plant, plant cell or plant tissue.

In some embodiments, the plant is a monocot or a dicot.

In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*.

Another aspect of this disclosure is directed to a method for producing a bioproduct, comprising subjecting the described genetically modified plant to a bioproduct conversion process.

In some embodiments, the bioproduct is selected from the group consisting of a bioenergy product, a biomaterial, a biopharmaceutical and a biocosmetics.

In some embodiments, the bioenergy product is ethanol and the bioproduct conversion process is an ethanol fermentation process.

In some embodiments, the bioproduct is selected from the group consisting of ethanol, biodiesel, biogas, bioplastics, biofoams, biorubber, biocomposites, and biofibres.

Another aspect of this disclosure is directed to a method for production of pulp or paper, comprising producing pulp or paper from the described genetically modified plant.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF THE DISCLOSURE

Definitions

Figure 1:
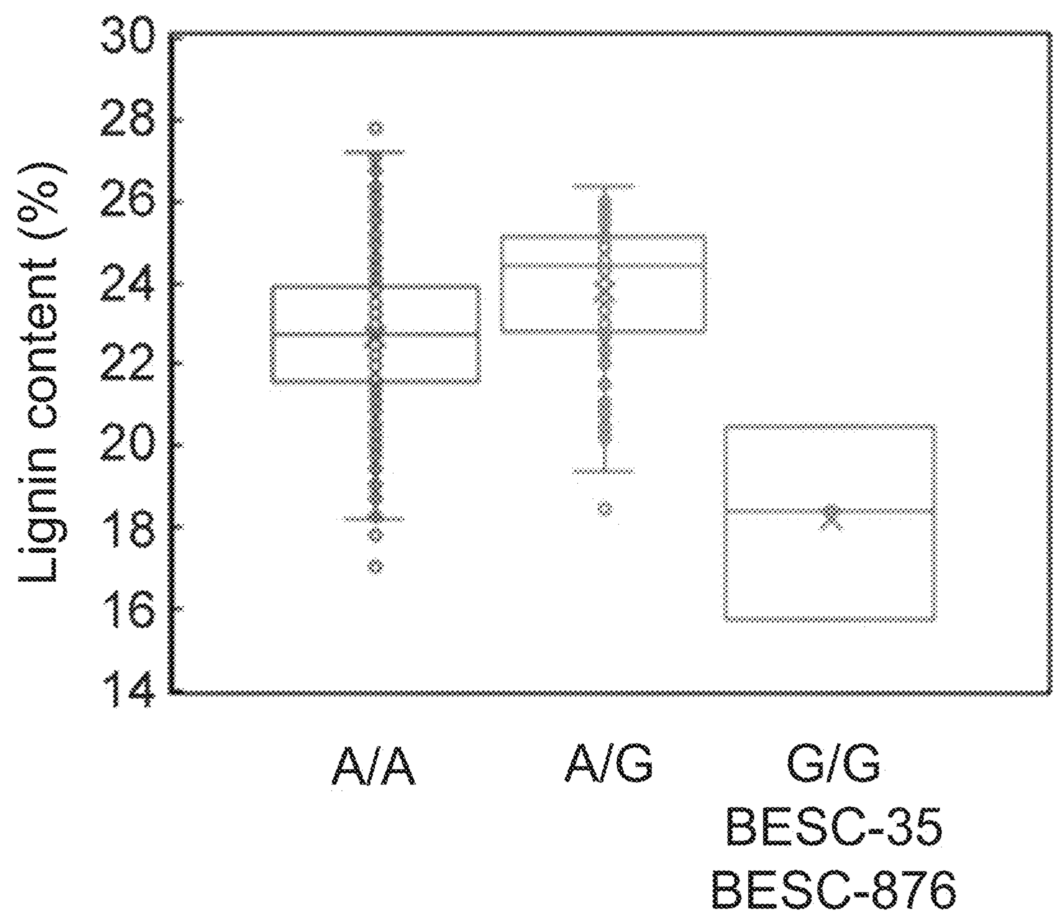
FIG. 1. Lignin content in *Populus* genotypes carrying loss of function PtrEPSP-TF allele (yellow) compared to *Populus* genotypes carrying the wild-type allele (blue and green). A/A indicates the two copies of PtrEPSP-TF have wild-type sequence. A/G indicates one PtrEPSP-TF copy has the mutation. G/G indicates the two copies of PtrEPSP-TF have the mutation.

Unless defined otherwise, all technical and scientific terms used herein have the same meaning as commonly understood by one of ordinary skill in the art to which this invention belongs.

As used herein, the term "about" refers to an approximately ±10% variation from a given value.

An "altered level of gene expression" refers to a measurable or observable change in the level of expression of a transcript of a gene, or the amount of its corresponding polypeptide, relative to a control plant or plant cell under the same conditions (e.g., as measured through a suitable assay such as quantitative RT-PCR, a Northern blot, a Western blot or through an observable change in phenotype, chemical profile or metabolic profile). An altered level of gene expression can include up-regulated or down-regulated expression of a transcript of a gene or polypeptide relative to a control plant or plant cell under the same conditions. Altered expression levels can occur under different environmental or developmental conditions or in different locations than those exhibited by a plant or plant cell in its native state.

The term "biofuel" refers to any type of fuel which is derived in any way from biomass. In some embodiments, the biofuel in the context of the present invention is a liquid biofuel. The biofuel may mainly comprise an extensively pure compound, thus, may be a biofuel comprising more than 95% of said compound and less than 5% of one or more other compound(s), of more than 80% of said compound and less than 20% of one or more other compound(s) or of more than 75% of said compound and less than 25% of one or more other compound(s). Alternatively, the biofuel may be a mixture of different compounds.

In some embodiments, the biofuel comprises one or more alcohol(s), one or more ester(s), one or more carbonic acid(s), one or more ketone(s), one or more aldehyde(s) or one and/or more terpene(s). In some embodiments, the biofuel comprises one or more alcohol(s), one or more ketone(s) (e.g., acetone), one or more aldehyde(s) and/or comprises one or more ester(s). In some embodiments, the biofuel comprises one or more alcohol(s) and/or comprises one or more ester(s). In some embodiments, the biofuel may comprise more than 50% (v/v), more than 70% (v/v), more than 80% (v/v), more than 90% (v/v) or more than 95% (v/v) of one or more alcohol(s). In some embodiments, these alcohols are aliphatic alcohols (e.g., methanol, ethanol, n-propanol, isopropanol and/or butanol), specifically aliphatic alcohols of the general molecular formula H—C—$H_{2n}$—OH, even more specifically, one of the first four aliphatic alcohols with n=1-4 (i.e., methanol, ethanol, propanol and/or butanol). In the context of the present invention these alcohols may also be designated as "bioalcohols" (i.e., as "biomethanol", "bioethanol", "biopropanol" and "biobutanol"). Due to its chemical and technical characteristics, in the context of biofuel, butanol is sometimes also designated as "biogasoline". In some embodiments, the alcohol may be a di-, tri or polyalcohol such as, e.g., glycerol. In some embodiments, the biofuel in the context of the present invention comprises more than 50% (v/v), more than 70% (v/v), more than 80% (v/v), more than 90% (v/v), or more than 95% (v/v) ethanol. In a specific embodiment, the biofuel of the present invention comprises at least 90% (v/v) ethanol.

As used herein, the term "biomass" refers to any cellulosic or lignocellulosic raw material and includes materials containing cellulose, and optionally further containing hemicellulose, lignin, starch, oligosaccharides and/or monosaccharides.

The term "cellulose" (also "lignocellulose" or "cellulosic substrate") refers to a structural material that comprises much of the mass of plants. Lignocellulose is composed mainly of carbohydrate polymers (cellulose, hemicelluloses) and an aromatic polymer (lignin).

The term "control plant" as used herein refers to a plant cell, an explant, seed, plant component, plant tissue, plant organ, or whole plant used to compare against transgenic or genetically modified plant for the purpose of identifying an enhanced phenotype or a desirable trait in the transgenic or genetically modified plant. A "control plant" may in some cases be a transgenic plant line that comprises an empty vector or marker gene, but does not contain the recombinant polynucleotide of interest that is present in the transgenic or genetically modified plant being evaluated. A control plant may be a plant of the same line or variety as the transgenic or genetically modified plant being tested, or it may be another line or variety, such as a plant known to have a specific phenotype, characteristic, or known genotype. A suitable control plant would include a genetically unaltered or non-transgenic plant of the parental line used to generate a transgenic plant herein.

As used herein, the term "CRISPR" refers to a RNA-guided endonuclease comprising a nuclease, such as Cas9, and a guide RNA that directs cleavage of the DNA by hybridizing to a recognition site in the genomic DNA.

The term "DNA," as used herein, refers to a nucleic acid molecule of one or more nucleotides in length, wherein the nucleotide(s) are nucleotides. By "nucleotide" it is meant a naturally-occurring nucleotide, as well as modified versions thereof. The term "DNA" includes double-stranded DNA, single-stranded DNA, isolated DNA such as cDNA, as well as modified DNA that differs from naturally-occurring DNA by the addition, deletion, substitution and/or alteration of one or more nucleotides as described herein.

The term "exogenous," as used herein, refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant or genetically modified cell. An "endogenous" nucleic acid molecule, gene, or protein can represent the organism's own gene or protein as it is naturally produced by the organism.

The term "expression" refers to the process of converting genetic information of a polynucleotide into RNA through transcription, which is catalyzed by an enzyme, RNA polymerase and into protein, through translation of mRNA on ribosomes. Expression can be, for example, constitutive or regulated, such as, by an inducible promoter (e.g., lac operon, which can be triggered by Isopropyl β-D-1-thiogalactopyranoside (IPTG)). Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states.

As used herein, the term "fermentation" refers to the enzymatic and/or anaerobic breakdown of organic substances by microorganisms to produce simpler organic compounds such as alcohols. While fermentation may occur under anaerobic conditions, it is not intended that the term be solely limited to strict anaerobic conditions, as fermentation may also occur under aerobic (e.g., in the presence of oxygen) or microaerobic conditions.

The term "gene," as used herein, refers to a segment of nucleic acid that encodes an individual protein or RNA and can include both exons and introns together with associated regulatory regions such as promoters, operators, terminators, 5' untranslated regions, 3' untranslated regions, and the like.

The term "genetically engineered" (or "genetically modified") refers to a microorganism comprising a manipulated genome or nucleic acids.

The term "hexose" refers to a monosaccharide with six carbon atoms, having the chemical formula $C_6H_{12}O_6$. Examples of hexose include glucose and fructose.

The term "homolog" means a gene related to a second gene by descent from a common ancestral DNA sequence, therefore, the corresponding polynucleotide/polypeptide has a certain degree of homology, i.e., sequence identity (at least 40%, at least 60%, at least 65%, particularly preferred at least 66%, 68%, 70%, 75%, 80%, 86%, 88%, 90%, 92%, 95%, 97% or 99% sequence identity). A "homolog" furthermore means that the function is equivalent to the function of the original gene. Homologs of a given gene and homologous positions in the gene can be determined by sequence alignment programs, e.g., including but not limited to, NCBI BLAST, ClustalW, DIAMOND, CS-BLAST, and MAFFT.

"Lignin", as used herein, refers to a complex polymer composed of monolignol subunits, primarily syringyl (S), guaiacyl (G) and p-hydroxyphenyl (H) monolignols, derived from sinapyl, coniferyl and p-coumaryl alcohols, respectively. Differences in the ratio of monolignols, and differences in expression and/or activity of lignin biosynthetic anabolic enzymes, create considerable variability in lignin structures, which differ between species, within species, within different tissues of a single plant and even within a single plant cell.

Lignin "synthesis" or "biosynthesis" refers to the production of lignin in a plant, plant tissue, or plant cell. "Lignin synthesis characteristics" or "lignin biosynthesis characteristics" include the total amount of lignin ("lignin content") in a plant or plant cell, the ratio or amount of monolignol subunits, and expression and/or activity of lignin biosynthetic enzymes.

As used herein, the term "nucleic acid" has its general meaning in the art and refers to a coding or non coding nucleic acid sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non coding region of a genome (i.e., nuclear or mitochondrial).

A "nucleic acid inhibitor" is a nucleic acid that can reduce or prevent expression or activity of a target gene. For example, an inhibitor of expression of a gene can reduce or eliminate transcription and/or translation of the gene product, thus reducing the gene protein expression.

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell* 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

The vectors provided herein also can include, for example origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

The term "variant," as used herein, refers to an alteration, variant or polymorphism in a nucleic acid sample or genome of a subject. Such alteration, variant or polymorphism can be with respect to a reference genome, which may be a reference genome of the subject or other individual. Single nucleotide polymorphisms (SNPs) are a form of polymorphisms. In some examples, one or more polymorphisms comprise one or more single nucleotide variations (SNVs), insertions, deletions, repeats, small insertions, small deletions, small repeats, structural variant junctions, variable length tandem repeats, and/or flanking sequences. Copy number variants (CNVs), transversions and other rearrangements are also forms of genetic variation. A genomic alternation may be a base change, insertion, deletion, repeat, copy number variation, or transversion.

General Description

Genetically-Modified Plants, Plant Tissues or Plant Cells

Disclosed herein is a genetically-modified plant, plant tissue or plant cell that has reduced lignin content as compared to a control plant which was not genetically modified. All the embodiments described herein for genetically modified plants are applicable to genetically modified plant cells and genetically modified plant tissues as well.

In some embodiments, the genetically modified plant, plant tissue or plant cell comprises a mutation in the endogenous, wild-type transcription factor PtrEPSP-TF gene (or a 5-enolpyruvylshikimate 3-phosphate synthase (EPSP) gene homolog in the plant) that destroys the DNA binding ability of the transcription factor. In some embodiments, the plant, plant tissue or plant cell expresses a PtrEPSP-TF mutant that lacks DNA binding activity. In some embodiments, mutations to the PtrRPSP-TF protein are introduced relative to the wild-type protein shown in SEQ ID NO: 7 or a variant or homolog thereof.

In some embodiments, the mutation in an endogenous PtrEPSP-TF gene or homolog or variant thereof, causes the PtrEPSP-TF transcription factor (protein) to lose DNA binding activity. In some embodiments, the PtrEPSP-TF mutant gene has at least 90% sequence homology to SEQ ID NO: 1 or the mutant PtrEPSP-TF protein has at least 90% sequence homology to SEQ ID NO: 2. In some embodiments, the mutant PtrEPSP-TF gene has at least 90%, 91%, 92%, 93%, 94%, 95%, 96%, 97%, 98% or 99% sequence homology to SEQ ID NO: 1 or the mutant PtrEPSP-TF protein has at least 90%, 91%, 92%, 93%, 94%, 95%, 96%, 97%, 98% or 99% sequence homology to SEQ ID NO: 2.

In some embodiments, the introduced mutation to the endogenous PtrEPSP-TF protein or homolog thereof is a non-conservative amino acid substitution at a position that corresponds to the amino acid 142 or amino acid 364 of SEQ ID NO: 7. A "non-conservative amino acid substitution" refers to replacement of an amino acid with another amino acid that differs from the first amino acid in its biochemical properties (charge, hydrophobicity or size) such that the substitution alters or destroys the function of the protein.

In a specific embodiment, the mutation is introduced by genome editing, which is achieved by a method selected from the group consisting of CRISPR/Cas system, Cre/Lox system, TALEN system, ZFNs system and homologous recombination.

In some embodiments, the CRISPR/Cas system comprises introducing into the plant a first nucleic acid encoding a Cas9 or Cas12 (previously called Cpf1) nuclease, a second nucleic acid comprising a guide RNA (gRNA), and a third nucleic acid comprising a homologous repair template of a PtrEPSP-TF gene wherein a mutation is present at the nucleotides corresponding to the DNA binding site of the protein, abolishing DNA binding activity. In a specific embodiment, the mutation at the DNA binding site of PtrEPSP is located at amino acid 142 or amino acid 364 of SEQ ID NO: 7, which abolishes PtrEPSP-TF DNA binding ability.

In some embodiments, the mutation is introduced by site-directed mutagenesis. Site-directed mutagenesis is described in Molecular Cloning, 3rd Ed., *Current Protocols in Molecular Biology*, and U.S. patent application Ser. No. 12/442,143, incorporated herein in its entirety.

In some embodiments, the disclosure is directed to plants, plant tissues or plant cells genetically modified with altered expression of a transcription factor that is regulated by PtrEPSP-TF, or a PtrEPSP-TF gene homolog. In some embodiments, the transcription factor that is regulated by PtrEPSP-TF is selected from the group consisting of MYB4, MYB58, SND2, VIN2, XND1, MYB48, MYB3R1, MYB3R3, and NAC047.

In some embodiments, the transcription factor that is regulated by PtrEPSP-TF is selected from the group consisting of MYB4, MYB58, SND2, and VIN2 (or homologs thereof), and the alteration comprises inactivation of the selected transcription factor, or homolog thereof, in the plant, resulting in reduced lignin content in the plant. The term "inactivation," as used herein, includes knocking out (e.g., deleting the gene using genome editing), knocking down (reducing the protein expression of a gene at least by 70%, e.g., by using nucleic acid inhibitor), or abolishing at least one function (e.g., DNA binding ability) of a gene.

In some embodiments, the inactivation of the selected gene is achieved by introducing a nucleic acid inhibitor of the selected gene to the plant. In some embodiments, the nucleic acid inhibitor is selected from the group consisting of an antisense RNA, a small interfering RNA, an RNAi, a microRNA, an artificial microRNA, and a ribozyme.

In some embodiments, the inactivation of the selected gene is achieved by genome editing, which is achieved by a method selected from the group consisting of CRISPR/Cas system, Cre/Lox system, TALEN system, ZFNs system and homologous recombination.

In some embodiments, the transcription factor that is regulated by PtrEPSP-TF is selected from the group consisting of XND1, MYB48, MYB3R1, MYB3R3, and NAC047, and wherein the alteration comprises expressing in the plant an exogenous nucleic acid comprising the selected gene, resulting in reduced lignin content in the plant.

In a specific embodiment, the exogenous nucleic acid comprises the XND1 gene shown by SEQ ID NO: 24, encoding the protein SEQ ID NO: 25. In some embodiments, the exogenous nucleic acid comprises a sequence that shows at least 90%, 91%, 92%, 93%, 94%, 95%, 96%, 97%, 98% or 99% identity to SEQ ID NO: 24. In some embodiments, the exogenous nucleic acid encodes a protein that shows at least 90%, 91%, 92%, 93%, 94%, 95%, 96%, 97%, 98% or 99% identity to SEQ ID NO: 25.

In a specific embodiment, the exogenous nucleic acid comprises the MYB48 gene shown by SEQ ID NO: 26, encoding the protein SEQ ID NO: 27. In some embodiments, the exogenous nucleic acid comprises a sequence that shows at least 90%, 91%, 92%, 93%, 94%, 95%, 96%, 97%, 98% or 99% identity to SEQ ID NO: 26. In some embodiments, the exogenous nucleic acid encodes a protein that shows at least 90%, 91%, 92%, 93%, 94%, 95%, 96%, 97%, 98% or 99% identity to SEQ ID NO: 27.

In a specific embodiment, the exogenous nucleic acid comprises the MYB3R1 gene shown by SEQ ID NO: 28, encoding the protein SEQ ID NO: 29. In some embodiments, the exogenous nucleic acid comprises a sequence that shows at least 90%, 91%, 92%, 93%, 94%, 95%, 96%, 97%, 98% or 99% identity to SEQ ID NO: 28. In some embodiments, the exogenous nucleic acid encodes a protein that shows at least 90%, 91%, 92%, 93%, 94%, 95%, 96%, 97%, 98% or 99% identity to SEQ ID NO: 29.

In a specific embodiment, the exogenous nucleic acid comprises the MYB3R3 gene shown by SEQ ID NO: 30, encoding the protein SEQ ID NO: 31. In some embodiments, the exogenous nucleic acid comprises a sequence that shows at least 90%, 91%, 92%, 93%, 94%, 95%, 96%, 97%, 98% or 99% identity to SEQ ID NO: 30. In some embodiments, the exogenous nucleic acid encodes a protein that shows at least 90%, 91%, 92%, 93%, 94%, 95%, 96%, 97%, 98% or 99% identity to SEQ ID NO: 31.

In a specific embodiment, the exogenous nucleic acid comprises the NAC047 gene shown by SEQ ID NO: 32, encoding the protein SEQ ID NO: 33. In some embodiments, the exogenous nucleic acid comprises a sequence that shows at least 90%, 91%, 92%, 93%, 94%, 95%, 96%, 97%, 98% or 99% identity to SEQ ID NO: 32. In some embodiments, the exogenous nucleic acid encodes a protein that shows at least 90%, 91%, 92%, 93%, 94%, 95%, 96%, 97%, 98% or 99% identity to SEQ ID NO: 33.

In some embodiments, the plant is a monocot or a dicot. In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*. In a specific embodiment, the plant is rice *Oryza sativa* or *Oryza glaberrima*.

A plant or plant cell used in methods of the invention may contain a recombinant nucleic acid construct as described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions.

Both transiently transformed and stably transformed transgenic plants and plant cells can be useful in the methods described herein.

Typically, genetically modified (transgenic) plant cells used in methods described herein constitute part or all of a whole plant. Such plants can be grown in a manner suitable for the species under consideration, either in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days or about 1-3 days. The use of transient assays is particularly convenient for rapid analysis in different species or to confirm expression of a heterologous BESC-35 and/or BESC-876 allelic variant whose expression has not previously been confirmed in particular recipient cells.

Initial and immediate application of the expression of BESC-35 and/or BESC-876 allelic variants can be made in the bioenergy crops *Populus* and switchgrass, but the application can be extended to other bioenergy crops such as corn, other sources of lignocellulosic biomass and other model plants e.g., *Salix, Miscanthus*, rice and *Medicago.*

For example, the vectors described herein can be used to transform a number of monocotyledonous and dicotyledonous plants and plant cell systems, including alfalfa, ash, beech, birch, canola, cherry, clover, cotton, cottonseed, eucalyptus, flax, jatropha, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, miscanthus, oat, rice, rye, ryegrass, sorghum, sudangrass, sugarcane, sweet corn, switchgrass, turf grasses, timothy and wheat. Gymnosperms such as fir, pine and spruce can also be suitable.

The methods and compositions can be used over a broad range of plant species, including species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium; and the monocot genera Agrostis, Avena, Festuca, Hordeum, Lemna, Lolium, Milium, Miscanthus oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*. In some embodiments, a plant is a member of the species *Festuca arundinacea, Miscanthus* hybrid (*Miscanthus×giganteus*), *Miscanthus sinensis, Miscanthus sacchariflorus, Panicum virgatum, Pennisetum purpureum, Phalaris arundinacea, Populus* spp including but not limited to *balsamifera, deltoides, tremuloides, tremula, alba* and *maximowiczii, Saccharum* spp., *Secale cereale, Sorghum almum, Sorghum halcapense* or *Sorghum vulgare*. In certain embodiments, the polynucleotides and vectors described herein can be used to transform a number of monocotyledonous and dicotyledonous plants and plant cell systems, wherein such plants are hybrids of different species.

Methods of Modulating Sugar Release and Lignin Content in a Plant

This disclosure further provides methods for regulating sugar release and lignin content of a plant.

In some embodiments, the method comprises introducing in a plant a mutation to the endogenous transcription factor PtrEPSP-TF, or a homolog thereof, wherein the mutated PtrEPSP-TF lacks DNA binding activity.

In a specific embodiment, the mutation is introduced by genome editing, which is achieved by a method selected from the group consisting of CRISPR/Cas system, Cre/Lox system, TALEN system, ZFNs system and homologous recombination.

In some embodiments, the CRISPR/Cas system comprises introducing into the plant a first nucleic acid encoding a Cas9 or Cas12 (previously called Cpf1) nuclease, a second nucleic acid comprising a guide RNA (gRNA), and a third nucleic acid comprising a homologous repair template of a PtrEPSP-TF gene wherein a mutation is present at the DNA binding site, abolishing DNA binding activity. In a specific embodiment, the mutation at the DNA binding site of PtrEPSP is located at amino acid 142 or amino acid 364 of SEQ ID NO: 7, which abolishes PtrEPSP-TF DNA binding ability.

In some embodiments, the mutation is introduced by site-directed mutagenesis. Site-directed mutagenesis is described in Molecular Cloning, 3rd Ed., *Current Protocols in Molecular Biology*, and U.S. patent application Ser. No. 12/442,143, incorporated herein in its entirety.

In some embodiments, the disclosure is directed to a method to modulate a transcription factor in a plant that is regulated by PtrEPSP-TF, or a PtrEPSP-TF gene homolog. In some embodiments, the transcription factor that is regulated by PtrEPSP-TF is selected from the group consisting of MYB4, MYB58, SND2, VIN2, XND1, MYB48, MYB3R1, MYB3R3, and NAC047.

In some embodiments, the transcription factor that is regulated by PtrEPSP-TF is selected from the group consisting of MYB4, MYB58, SND2, and VIN2 (or homologs thereof), and the alteration comprises inactivation of the selected transcription factor, or homolog thereof, in the plant, resulting in reduced lignin content in the plant.

In some embodiments, the inactivation of the selected gene is achieved by introducing a nucleic acid inhibitor of the selected gene to the plant. In some embodiments, the nucleic acid inhibitor is selected from the group consisting of an antisense RNA, a small interfering RNA, an RNAi, a microRNA, an artificial microRNA, and a ribozyme.

In some embodiments, the inactivation of the selected gene is achieved by genome editing, which is achieved by a method selected from the group consisting of CRISPR/Cas system, Cre/Lox system, TALEN system, ZFNs system and homologous recombination.

In some embodiments, the transcription factor that is regulated by PtrEPSP-TF is selected from the group consisting of XND1, MYB48, MYB3R1, MYB3R3, and NAC047, and wherein the modulation/alteration comprises expressing in the plant an exogenous nucleic acid comprising the selected gene, resulting in reduced lignin content in the plant.

In a specific embodiment, the exogenous nucleic acid comprises the XND1 gene shown by SEQ ID NO: 24, encoding the protein SEQ ID NO: 25. In some embodiments, the exogenous nucleic acid comprises a sequence that shows at least 90%, 91%, 92%, 93%, 94%, 95%, 96%, 97%, 98% or 99% identity to SEQ ID NO: 24. In some embodiments, the exogenous nucleic acid encodes a protein that shows at least 90%, 91%, 92%, 93%, 94%, 95%, 96%, 97%, 98% or 99% identity to SEQ ID NO: 25.

In a specific embodiment, the exogenous nucleic acid comprises the MYB48 gene shown by SEQ ID NO: 26, encoding the protein SEQ ID NO: 27. In some embodiments, the exogenous nucleic acid comprises a sequence that shows at least 90%, 91%, 92%, 93%, 94%, 95%, 96%, 97%, 98% or 99% identity to SEQ ID NO: 26. In some embodiments, the exogenous nucleic acid encodes a protein that shows at least 90%, 91%, 92%, 93%, 94%, 95%, 96%, 97%, 98% or 99% identity to SEQ ID NO: 27.

In a specific embodiment, the exogenous nucleic acid comprises the MYB3R1 gene shown by SEQ ID NO: 28, encoding the protein SEQ ID NO: 29. In some embodiments, the exogenous nucleic acid comprises a sequence that shows at least 90%, 91%, 92%, 93%, 94%, 95%, 96%, 97%, 98% or 99% identity to SEQ ID NO: 28. In some embodiments, the exogenous nucleic acid encodes a protein that shows at least 90%, 91%, 92%, 93%, 94%, 95%, 96%, 97%, 98% or 99% identity to SEQ ID NO: 29.

In a specific embodiment, the exogenous nucleic acid comprises the MYB3R3 gene shown by SEQ ID NO: 30, encoding the protein SEQ ID NO: 31. In some embodiments, the exogenous nucleic acid comprises a sequence that shows at least 90%, 91%, 92%, 93%, 94%, 95%, 96%, 97%, 98% or 99% identity to SEQ ID NO: 30. In some embodiments, the exogenous nucleic acid encodes a protein that shows at least 90%, 91%, 92%, 93%, 94%, 95%, 96%, 97%, 98% or 99% identity to SEQ ID NO: 31.

In a specific embodiment, the exogenous nucleic acid comprises the NAC047 gene shown by SEQ ID NO: 32, encoding the protein SEQ ID NO: 33. In some embodiments, the exogenous nucleic acid comprises a sequence that shows at least 90%, 91%, 92%, 93%, 94%, 95%, 96%, 97%, 98% or 99% identity to SEQ ID NO: 32. In some embodiments, the exogenous nucleic acid encodes a protein that shows at least 90%, 91%, 92%, 93%, 94%, 95%, 96%, 97%, 98% or 99% identity to SEQ ID NO: 33.

In some embodiments, gene modulation (either increasing or decreasing gene expression or activity) is achieved using available gene targeting technologies in the art. Examples of gene targeting technologies include the Cre/Lox system (described in Kuhn, R., & M. Tones, R., 2002. *Transgenesis Techniques: Principles and Protocols,* 175-204.), homologous recombination (described in Capecchi, Mario R. 1989. *Science,* 244: 1288-1292), TALENs (described in Sommer et al., 2015. *Chromosome Research,* 23: 43-55, and Cermak et al., 2011. *Nucleic Acids Research*: gkr218.), and CRISPR Cas system as described in Ran F A et al., 2013. *Nature Protocols.*

In one embodiment, gene modulation is achieved by a CRISPR/Cas system. CRISPR-Cas and similar gene targeting systems are well known in the art with reagents and protocols readily available (Mali, P. et al., 2013. *Science,* 339(6121), 823-826; Hsu, P. D. et al., 2014. *Cell,* 157.6: 1262-1278; Jiang et al., 2013. *Nature Biotechnology,* 31, 233-239). Exemplary genome editing protocols are described in Jennifer Doudna, and Prashant *Mali,* 2016. *"CRISPR-Cas: A Laboratory Manual"* (CSHL Press, ISBN: 978-1-621821-30-4) and Ran, F. Ann, et al. 2013. *Nature Protocols,* 8 (11): 2281-2308.

A CRISPR endonuclease comprises two components: (1) an RNA-dependent nuclease, typically microbial Cas9; and (2) a short "guide RNA" (gRNA or sgRNA) comprising a ~20 nucleotide targeting sequence that directs the nuclease to a location of interest in the genome. When co-expressed with an artificial sgRNA targeting a cellular gene, the Cas9 endonuclease generates double-stranded breaks of DNA at the targeted locus. In addition, when CRISPR endonuclease is supplemented with a stretch of DNA template homologous to the break region, the break is repaired using the supplied homologous DNA template via the process of homologous recombination (HR). CRISPR-mediated HR makes it possible to specifically edit the target DNA sequence and/or alter gene expression.

Modulation of the PtrEPSP-TF gene, a PtrEPSP-TF homolog, or a transcription factor that is regulated by PtrEPSP-TF, in a plant can lead to proteins with altered activity. "Altered activity" includes an increase or decrease in a known activity of a protein encoded by a gene of interest, including loss of an established or proposed function, or gain of a new function. For example, the inventors have determined that modulating the PtrEPSP-TF gene, a PtrEPSP-TF homolog, or a transcription factor that is regulated by PtrEPSP-TF, for example, by mutating the PtrEPSP-TF gene, a PtrEPSP-TF homolog such that the PtrEPSP-TF protein lacks DNA binding ability, or manipulating the expression of a transcription factor that is regulated by PtrEPSP-TF, can affect cellulose and lignin content and/or sugar release.

Altered S/G ratios in a plant (e.g., *Populus* species) include, for example, alterations from essentially 50% syringyl ("S"):50% guaiacyl ("G") units to essentially 100% syringyl units, or essentially 100% guaiacyl units. The terms "units" and "subunits" are used interchangeably herein. Specific S/G ratios include, for example, greater than 2:1, e.g., 2.1:1, 2.2:1, 2.5:1, 2.8:1, 3.0:1, 3.5:1, 4:1, etc; or less than 2:1, e.g., 0.5:1, 0.8:1, 1:1, 1.2:1, 1.5:1, 1.8:1, or 2:1.3, 2:1.5, 2:1.7, 2:1.9, etc. The ratio of syringyl to guaiacyl units can be increased or decreased, e.g., by 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold or more than 3.0-fold, in a plant as compared to the corresponding S/G ratio in a control plant. In some cases, the ratio of syringyl units incorporated into lignin in a plant described herein can be increased or decreased, e.g., by 5%, 10%, 15%, 20%, 25%, 30%, 35%, 40%, 45%, 50%, 60%, 70%, 80%, 90%, 100% or more than 100%, as compared to the corresponding ratio in a control plant.

By manipulating the PtrEPSP-TF gene, a PtrEPSP-TF homolog, or a transcription factor that is regulated by PtrEPSP-TF, the amount and/or rate of S subunit to G subunit biosynthesis, or the incorporation of S to G subunits into the lignin structure, can be altered. Alteration in the S/G subunit ratio alters the lignin composition of the plant cell wall. Manipulating the BESC-35 and/or BESC-876 gene can thus modulate the lignin composition of a plant.

G units have greater capacity for cross-linking between monomers relative to S units. Thus, increasing the ratio of S/G subunits to greater than 2:1 increases S subunits and decreases G subunits in lignin and thus decreases cross-linking between subunits incorporated into lignin. This makes plants with an S/G ratio greater than 2:1 more degradable than wild-type plants because there is less cross-linkage between lignin units and therefore plants with an S/G ratio greater than 2:1 are more susceptible to extraction processes, which decreases recalcitrance and increases sugar release. Higher S/G ratio has been shown to increase sugar release in *Populus* at values above 2.0. The exact way this occurs is not known though it is speculated that lignin remains intact during saccharification under high temperature and/or pressure. Nevertheless, biomass with an S/G ratio above 2.0 releases more sugar.

"Sugar release" includes high or low release of sugars, also referred to as low or high recalcitrance. "High" sugar release (i.e., low recalcitrance) means that sugar can be extracted more easily, or more sugar can be extracted, from a plant, under conditions that would result in less sugar release in a plant without the particular allelic variant or genetic modification. "Low" sugar release (i.e., high recalcitrance) means that sugar can be extracted less easily, or less sugar can be extracted, from a plant, under conditions that would result in more sugar release in a plant without the particular allelic variant or genetic modification. In one example, sugar release refers to the amount of 5- and 6-carbon sugars that can be recovered from a plant using standard techniques to extract these sugars from plant materials. Sugars that can be released include, but are not limited to, glucose, xylose, fructose, arabinose, lactose, ribose, mannose, galactose, and sucrose. Examples of 5-carbon sugars (pentoses) include xylose, ribose, and arabinose; examples of 6-carbon sugars include glucose, fructose, mannose, and galactose.

Sugar release can be measured, for example, by saccharification analysis. In one example of saccharification analysis, sugars are extracted with alpha-amylase and β-glucosidase in sodium acetate, followed by an ethanol soxhlet extraction. After drying overnight, water is added, and samples are sealed and reacted. Once cooled, a buffer-enzyme mix with cellulose oxidative enzymes is added and incubated with the sample. After incubation, an aliquot of the saccharified hydrolysate is tested for sugar content/release, such as by addition of glucose oxidase/peroxidase for measuring glucose content, and/or xylose dehydrogenase to measure xylose content.

High or low sugar release can be an increase or decrease in sugar release or sugar recovery of 2%, 5%, 8%, 10%, 15%, 20%, 25%, 30%, 40%, 50%, 60%, 70%, 80%, 90%, or 100% in a plant with a particular modulation of the Potri.011G009500 gene, relative to sugar release or sugar recovery from a plant that does not have the modulation of the Potri.008G064000 gene. In one example, "low" glucose release is glucose release of less than 0.1, 0.15, 0.2, or 0.25 g glucose per g biomass. "High" glucose release is glucose release of 0.3, 0.35, 0.4, or 0.45 g glucose per g biomass or more. "Low" glucose/xylose release is combined release of glucose and xylose of less than 0.2, 0.25, 0.3, 0.35, or 0.4 g combined glucose/xylose per g biomass. "High" glucose/xylose release is combined release of glucose and xylose above 0.4, 0.45, 0.5, 0.55, or 0.6 g combined glucose/xylose per g biomass.

Lignin forms strong bonds with sugars and interferes with access to these carbohydrates, making it difficult to extract the plant's sugars contained in cellulose and hemicellulose. Differences in lignin content alter the sugar release properties of a plant in the extraction process. Lower lignin levels in a plant are associated with higher levels of sugar release, while higher lignin levels are associated with lower levels of sugar release. Thus, sugar release and lignin content can show an inverse correlation. In addition, the higher interactions of cell wall components (including lignins) also determine the amount of sugar that can be released.

In some embodiments, the plant is a monocot or a dicot. In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*. In a specific embodiment, the plant is rice *Oryza sativa* or *Oryza glaberrima*.

Inhibitors and Expression Vectors for Modulating the Activity of Genes

Further disclosed herein are nucleic acid inhibitors of expression of PtrEPSP-TF, a PtrEPSP-TF homolog and/or a transcription factor that is regulated by PtrEPSP-TF, or inhibitors of expression of allelic variants of PtrEPSP-TF, a PtrEPSP-TF homolog and/or a transcription factor that is regulated by PtrEPSP-TF, which can be used to reduce expression of the PtrEPSP-TF, a PtrEPSP-TF homolog and/or a transcription factor that is regulated by PtrEPSP-TF gene and allelic variants thereof, to provide high sugar release, and/or altered S/G ratio. Specific nucleic acid inhibitors include antisense RNA, small interfering RNA, RNAi, microRNA, artificial microRNA, and ribozymes.

In some embodiments, the transcription factor that is regulated by PtrEPSP-TF is selected from the group consisting of MYB4, MYB58, SND2, and VIN2 (or homologs thereof).

Techniques for introducing nucleic acids (inhibitors and expression vectors) into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204,253, 6,329,571 and 6,013,863. If a cell or tissue culture is used as the recipient tissue for transformation, plants can be regenerated from transformed cultures if desired, by techniques known to those skilled in the art. See, e.g., Niu et al., 2000. *Plant Cell Rep. V*19:304-310; Chang and Yang, 1996. *Bot. Bull. Acad. Sin.*, V37:35-40 and Han et al., Biotechnology in Agriculture and Forestry, V44:291 (ed. by Y. P. S. Bajaj), Springer-Vernag, (1999).

Nucleic Acid Inhibitors

A number of nucleic acid based methods, including antisense RNA, ribozyme directed RNA cleavage, post-transcriptional gene silencing (PTGS), e.g., RNA interference (RNAi), microRNA and artificial microRNA and transcriptional gene silencing (TGS) can be used to inhibit the expression of PtrEPSP-TF, a PtrEPSP-TF homolog and/or a transcription factor that is regulated by PtrEPSP-TF in plants. In some embodiments, the transcription factor that is regulated by PtrEPSP-TF is selected from the group consisting of MYB4, MYB58, SND2, and VIN2 (or homologs thereof).

Suitable nucleic acid inhibitors, i.e., nucleic acids capable of inhibiting the expression of a target gene, include full-length nucleic acids of allelic variants of PtrEPSP-TF, a PtrEPSP-TF homolog and/or a transcription factor that is regulated by PtrEPSP-TF, or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid segment from a gene to be repressed is cloned and operably linked to a regulatory region and a transcription termination sequence so that the antisense strand of RNA is transcribed. The recombinant vector is then transformed into plants, as described below and the antisense strand of RNA is produced. The nucleic acid segment need not be the entire sequence of the gene to be repressed, but typically will be substantially complementary to at least a portion of the sense strand of the gene to be repressed.

In another method, a nucleic acid can be transcribed into a ribozyme or catalytic RNA, which affects expression of an mRNA. See, U.S. Pat. No. 6,423,885. Ribozymes can be designed to specifically pair with a target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes cleave mRNAs at locations dictated by flanking regions that form complementary base pairs with the target mRNA. See, for example, U.S. Pat. No. 5,254,678; Perriman et al., *PNAS* 92(13):6175-6179 (1995); de Feyter and Gaudron, Methods in Molecular Biology, Vol. 74, Chapter 43, Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof, of the polypeptide of interest. The length of the sequence that is similar or identical to the sense coding sequence can be from 10 nucleotides to 500 nucleotides, from 15 nucleotides to 300 nucleotides, from 20 nucleotides to 100 nucleotides or from 25 nucleotides to 100 nucleotides. The other strand of the stem portion of a double stranded RNA comprises a sequence that is similar or identical to the antisense strand or a fragment thereof, of the coding sequence of the polypeptide of interest and can have a length that is shorter, the same as or longer than the corresponding length of the sense sequence. In some cases, one strand of the stem portion of a double stranded RNA comprises a sequence that is similar or identical to the 3' or 5' untranslated region or a fragment thereof, of the mRNA encoding the polypeptide of interest and the other strand of the stem portion of the double stranded RNA comprises a sequence that is similar or identical to the sequence that is complementary to the 3' or 5' untranslated region, respectively or a fragment thereof, of the mRNA encoding the polypeptide of interest. In other embodiments, one strand of the stem portion of a double stranded RNA comprises a sequence that is similar or identical to the sequence of an intron or a fragment thereof in the pre-mRNA encoding the polypeptide of interest and the other strand of the stem portion comprises a sequence that is similar or identical to the sequence that is complementary to the sequence of the intron or fragment thereof in the pre-mRNA.

A construct including a sequence that is operably linked to a regulatory region and a transcription termination sequence and that is transcribed into an RNA that can form a double stranded RNA, can be transformed into plants as described below. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330 and 20030180945.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA or an intron in a pre-mRNA encoding a polypeptide of interest or a fragment of such sequences. In some embodiments, the sense or antisense sequence is identical or complementary to a sequence of the regulatory region that drives transcription of the gene encoding a polypeptide of interest. In each case, the sense sequence is the sequence that is complementary to the antisense sequence.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand and one from the bottom strand. See, for example, Yan et al., *Plant Physiol.,* 141: 1508-1518 (2006). The two regulatory regions can be the same or different. The two transcripts can form double-stranded RNA molecules that induce degradation of the target RNA. In some cases, a nucleic acid can be positioned within a P-DNA such that the left and right border-like sequences of the P-DNA are on either side of the nucleic acid.

In some embodiments, a suitable nucleic acid inhibitor can be a nucleic acid analog. Nucleic acid analogs can be modified at the base moiety, sugar moiety or phosphate backbone to improve, for example, stability, hybridization or solubility of the nucleic acid. Modifications at the base moiety include deoxyuridine for deoxythymidine and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring or peptide nucleic acids, in which the deoxyphosphate backbone is replaced by a pseudopeptide backbone and the four bases are retained. See, for example, Summerton and Weller, 1997, *Antisense Nucleic Acid Drug Dev.,* 7:187-195; Hyrup et al., *Bioorgan. Med. Chem.,* 4:5-23 (1996). In addition, the deoxyphosphate backbone can be replaced with, for example, a phosphorothioate or phosphorodithioate backbone, a phosphoroamidite or an alkyl phosphotriester backbone.

Expression Vector Modulators

This disclosure provides a exogenous nucleic acid vector that comprises a nucleotide sequence that is transcribed into expression or overexpression of a transcription factor that is regulated by PtrEPSP-TF operably linked to a regulatory region that is functional in a plant as described above, where a tissue of a plant produced from the plant cell has an altered cell wall compared to the cell wall in tissue of a control plant that does not comprise the nucleic acid inhibitor.

In some embodiments, the transcription factor that is regulated by PtrEPSP-TF is selected from the group consisting of XND1, MYB48, MYB3R1, MYB3R3, and NAC047.

In a specific embodiment, the exogenous nucleic acid comprises the XND1 gene shown by SEQ ID NO: 24, encoding the protein SEQ ID NO: 25. In some embodiments, the exogenous nucleic acid comprises a sequence that shows at least 90%, 91%, 92%, 93%, 94%, 95%, 96%, 97%, 98% or 99% identity to SEQ ID NO: 24. In some embodiments, the exogenous nucleic acid encodes a protein that shows at least 90%, 91%, 92%, 93%, 94%, 95%, 96%, 97%, 98% or 99% identity to SEQ ID NO: 25.

In a specific embodiment, the exogenous nucleic acid comprises the MYB48 gene shown by SEQ ID NO: 26, encoding the protein SEQ ID NO: 27. In some embodiments, the exogenous nucleic acid comprises a sequence that shows at least 90%, 91%, 92%, 93%, 94%, 95%, 96%, 97%, 98% or 99% identity to SEQ ID NO: 26. In some embodiments, the exogenous nucleic acid encodes a protein that shows at least 90%, 91%, 92%, 93%, 94%, 95%, 96%, 97%, 98% or 99% identity to SEQ ID NO: 27.

In a specific embodiment, the exogenous nucleic acid comprises the MYB3R1 gene shown by SEQ ID NO: 28, encoding the protein SEQ ID NO: 29. In some embodiments, the exogenous nucleic acid comprises a sequence that shows at least 90%, 91%, 92%, 93%, 94%, 95%, 96%, 97%, 98% or 99% identity to SEQ ID NO: 28. In some embodiments, the exogenous nucleic acid encodes a protein that shows at least 90%, 91%, 92%, 93%, 94%, 95%, 96%, 97%, 98% or 99% identity to SEQ ID NO: 29.

In a specific embodiment, the exogenous nucleic acid comprises the MYB3R3 gene shown by SEQ ID NO: 30, encoding the protein SEQ ID NO: 31. In some embodiments, the exogenous nucleic acid comprises a sequence that shows at least 90%, 91%, 92%, 93%, 94%, 95%, 96%, 97%, 98% or 99% identity to SEQ ID NO: 30. In some embodiments, the exogenous nucleic acid encodes a protein that shows at least 90%, 91%, 92%, 93%, 94%, 95%, 96%, 97%, 98% or 99% identity to SEQ ID NO: 31.

In a specific embodiment, the exogenous nucleic acid comprises the NAC047 gene shown by SEQ ID NO: 32, encoding the protein SEQ ID NO: 33. In some embodiments, the exogenous nucleic acid comprises a sequence that shows at least 90%, 91%, 92%, 93%, 94%, 95%, 96%, 97%, 98% or 99% identity to SEQ ID NO: 32. In some embodiments, the exogenous nucleic acid encodes a protein that shows at least 90%, 91%, 92%, 93%, 94%, 95%, 96%, 97%, 98% or 99% identity to SEQ ID NO: 33.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

Some suitable regulatory regions initiate transcription, only or predominantly, in certain cell types. For example, a promoter that is active predominantly in a reproductive tissue (e.g., fruit, ovule or inflorescence) can be used. Thus, as used herein a cell type- or tissue-preferential promoter is one that drives expression preferentially in the target tissue, but may also lead to some expression in other cell types or tissues as well.

Root-active and root-preferential promoters confer transcription in root tissue, e.g., root endodermis, root epidermis or root vascular tissues. Root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990) and the tobacco RD2 promoter.

Promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cab IR promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis* SUC2 sucrose-H+ symporter promoter (Truernit et al., *Planta,* 196:564-570 (1995)) and thylakoid membrane protein promoters from spinach (psaD, psaF, psaE, PC, FNR, atpC, atpD, cab, rbcS).

Lignin biosynthesis promoters are promoters that drive transcription of nucleic acids encoding enzymes involved in lignin biosynthesis. Examples of lignin biosynthesis promoters include promoters of the switchgrass (*Panicum virgatum*), rice (*Oryza sativa*), corn (*Zea mays*) and wheat (*Triticum aestivum*) homologs of the *Populus* cinnamate 4-hydroxylase, caffeoyl-CoA O-methyltransferase and caffeic acid O-methyltransferase genes. Also suitable are promoters of *Arabidopsis* genes encoding phenylalanin ammonia lyase (genomic locus At3g10340), trans-cinnamate 4-hydroxylase (genomic locus At2g30490), 4-coumarate: CoA ligase (genomic locus At1g51680), hydroxycinnamoyl-CoA:shikimate/quinate hydroxycinnamoyltransferase (genomic locus At5g48930), p-coumarate 3-hydroxylase (genomic locus At2g40890), caffeoyl-CoA 3-O-methyltransferase (genomic locus At4g34050), cinnamoyl CoA reductase (genomic locus At1g15950), ferulate 5-hydroxylase (genomic locus At4g36220), caffeic acid O-methyltransferase (genomic locus At5g54160) and cinnamyl alcohol dehydrogenase (genomic locus At4g34230).

Useful promoters also include cell wall related promoters, such as cellulose biosynthesis promoters. Cellulose biosynthesis promoters are promoters that drive transcription of nucleic acids encoding enzymes involved in cellulose biosynthesis. Examples of cellulose biosynthesis promoters include the promoter of the rice cellulose synthase gene (genomic locus Os08g25710), the promoter of the rice cellulose synthase gene (genomic locus Os08g06380) and the promoter of the rice cellulose synthase-like A2 gene (genomic locus Os10g26630).

Examples of promoters that have high or preferential activity in vascular bundles include the glycine-rich cell wall protein GRP 1.8 promoter (Keller and Baumgartner, *Plant Cell,* 3(10):1051-1061 (1991)), the Commelina yellow mottle virus (CoYMV) promoter (Medberry et al., *Plant Cell,* 4(2):185-192 (1992)) and the rice tungro bacilliform virus (RTBV) promoter (Dai et al., *Proc. Natl. Acad. Sci. USA,* 101(2):687-692 (2004)). Promoters having preferential activity in the phloem region (e.g., primary phloem cells, companion cells and sieve cells), the xylem region (e.g., tracheids and vessels), the bundle sheath layer and/or the endodermis are also considered vascular tissue promoters. Promoters that have preferential activity in the pith, cortex, epidermis and/or in the vascular bundles or vascular layers of the stem are considered stem promoters. In some cases, the activity of stem promoters can also be induced by stress like drought.

Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators and inducible elements. Thus, for example, more than one regulatory region can be operably linked to the sequence of a polynucleotide encoding a Gene Y homolog or other lignin-modulating polypeptide. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

In one aspect, a plant cell comprising a BESC-35 and/or BESC-876 nucleic acid inhibitor is provided. The plant cell comprises an exogenous nucleic acid, the exogenous nucleic acid comprising a regulatory region operably linked to a polynucleotide that is transcribed into an interfering RNA effective for inhibiting expression of BESC-35 and/or BESC-876 or a BESC-35 and/or BESC-876 allelic variant. The exogenous nucleic acid can further comprise a 3' UTR operably linked to the polynucleotide. The polynucleotide can be transcribed into an interfering RNA comprising a stem-loop structure. The stem-loop structure can comprise an inverted repeat of the 3' UTR.

In another aspect, a plant is provided. The plant comprises any of the plant cells described above. Progeny of the plant also are provided, where the progeny have altered lignin content, sugar release and cell wall structure.

Methods of Use of Genetically Modified (Transgenic) Plants

Disclosed herein are methods to increase glucose and/or xylose release in a plant or plant cell, or to alter lignin content, by expressing the disclosed inhibitors in plants and plant cells.

Further improved methods of producing biofuel from cellulosic biomass, by using plants with a mutant transcription factor PtrEPSP-TF, or homolog thereof, that lacks DNA binding ability, or modulated expression of a transcription factor that is regulated by PtrEPSP-TF in biofuel production processes. Methods of pretreatment and saccharification of biomass to fermentable sugars, followed by fermentation of the sugars to ethanol, are known in the art.

Articles of Manufacture

The materials and methods described herein are useful for modifying biomass characteristics, such as characteristics of biomass renewable energy source plants. According to the invention, biomass may be derived from a single source, or biomass can contain a mixture derived from more than one source; for example, biomass can contain a mixture of corn cobs and corn stover, or a mixture of grass and leaves. Examples of biomass include, but are not limited to, tree crops such as *Populus*, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from processing of grains, trees, branches, roots, leaves, wood chips, sawdust, shrubs and bushes, vegetables, and fruits.

Lignin itself, which can be gathered from transgenic plants provided herein, can be converted into valuable fuel additives. Lignin can be recovered from any bioethanol production process using agricultural materials such as straw, corn stalks and switchgrass engineered to have increased lignin content. Lignin can be combusted to provide heat and/or power for the ethanol process; however, increasing the value of the lignin by converting it to higher value fuel additives can significantly enhance the competitiveness of bioethanol technology. Lignins removed from wood pulp as sulphates can be used as dust suppression agents for roads, as dispersants in high performance cement applications, water treatment formulations and textile dyes or as raw materials for several chemicals, such as vanillin, DMSA, ethanol, torula yeast, xylitol sugar and humic acid.

Seeds of transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material or a label inserted within the package. The package label may indicate that the seed herein incorporates transgenes that provide altered lignin content in one or more tissues of plants grown from such seeds.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

EXAMPLES

Example 1: Characterization of BESC-35 and BESC-876 and Sequences

The inventors have studied the sequence of Potri.002G146400 (*Populus trichocarpa* 5-enolpyruvylshikimate 3-phosphate synthase gene (PtrEPSP)) loss of function alleles BESC-35 and BESC-876 (SEQ. ID. NO: 1-4). BESC-35 contains two nucleotide changes: at position 426, T is substituted by G; at position 585, T is substituted by C (SEQ. ID. NO: 1). These changes in DNA sequence results in one amino acid change: at position 142, Asp is substituted by Glu (SEQ. ID. NO: 2). BESC-876 contains three nucleotide changes: at position 426, T is substituted by G; at position 585, T is substituted by C; at position 1091, T is substituted by C (SEQ. ID. NO: 3). These changes in DNA sequence results in two amino acid changes: at position 142, Asp is substituted by Eau; at position 364, Leu is substituted by Pro (SEQ. ID. NO: 4).

Sequences

SEQ ID NO: 1: nucleic acid sequence of PtrEPSP in BESC-35

SEQ ID NO: 2: amino acid sequence of PtrEPSP in BESC-35

SEQ ID NO: 3: nucleic acid sequence of PtrEPSP in BESC-876

SEQ ID NO: 4: amino acid sequence of PtrEPSP in BESC-876

SEQ ID NO: 5: EPSP-1219F forward primer

SEQ ID NO: 6: OCS-R reverse primer

SEQ ID NO: 7: PtrEPSP wild type amino acid sequence

SEQ ID NO: 8: MYB4a nucleic acid sequence

SEQ ID NO: 9: MYB4a amino acid sequence

SEQ ID NO: 10: MYB4b nucleic acid sequence

SEQ ID NO: 11: MYB4b amino acid sequence

SEQ ID NO: 12: MYB4c nucleic acid sequence

SEQ ID NO: 13: MYB4c amino acid sequence

SEQ ID NO: 14: MYB4d nucleic acid sequence

SEQ ID NO: 15: MYB4d amino acid sequence

SEQ ID NO: 16: MYB58 nucleic acid sequence

SEQ ID NO: 17: MYB58 amino acid sequence

SEQ ID NO: 18: SND2 nucleic acid sequence

SEQ ID NO: 19: SND2 amino acid sequence

SEQ ID NO: 20: VIN2a nucleic acid sequence

SEQ ID NO: 21: VIN2a amino acid sequence

SEQ ID NO: 22: VIN2b nucleic acid sequence

SEQ ID NO: 23: VNI2b amino acid sequence

SEQ ID NO: 24: XND1 nucleic acid sequence

SEQ ID NO: 25: XND1 amino acid sequence

SEQ ID NO: 26: MYB48 nucleic acid sequence

SEQ ID NO: 27: MYB48 amino acid sequence

SEQ ID NO: 28: MYB3R1 nucleic acid sequence

SEQ ID NO: 29: MYB3R1 amino acid sequence

SEQ ID NO: 30: MYB3R3 nucleic acid sequence

SEQ ID NO: 31: MYB3R3 amino acid sequence

SEQ ID NO: 32: NAC047 nucleic acid sequence

SEQ ID NO: 33: NAC047 amino acid sequence.

Transgenic Plants/Plant Species/Plant Cells

BESC-35 and BESC-876 *Populus* plants are separated from natural *Populus* population.

For transgenic rice, Potri.002G146400, BESC-35, and BESC-876 are cloned into pANIC10A vector, and then transformed into rice genotype *Japonica taipei* 309, respectively.

Transiently transformed plant cells are used to analyze the repression of PtrhAT. Cells are isolated from 2-month-old *Populus* leaves. For reporter construct, ~250-bp PtrhAT promoter (−460 to −210 from start codon) is inserted between 35S promoter and GUS reporter gene. GUS activity is measured 16 hours after transfection. This is a convenient and quick method to determine the transcriptional repression activity of Potri.002G146400 and its alleles.

The molecular basis of BESC-35 and BESC-876 will provide promising targets to modulate the activity of PtrEPSP-TF, which will reduce side-effects of introducing exogenous genes into plants. This will then facilitate the engineering of plants with promoted cell wall recalcitrance and flavonoid production. The result that PtrEPSP-TF also affects cell wall biosynthesis and MYB46 expression in rice will extend the application of PtEPSP-TF to monocot plants, especially important food crops. By modulating the expression of PfrEPSP-TF, the nutrient value of food crops will be improved. New targets of PtrEPSP-TF in rice will provide new engineering targets to modify cell wall property.

BESC-35 and BESC-876 are two loss of function alleles of PtrEPSP-TF. The loss of the DNA binding activity and transcriptional activity of the two alleles are due to amino acid substitution at position 142 and 364. This discovery provides one strategy to modulate the activity of PtrEPSP-TF without introducing exogenous genes in *Populus* plants. In monocot plant rice, overexpression of PtrEPSP-TF can enhance the expression of cell wall biosynthesis genes and MYB46, which is similar to the phenotype in dicot plant *Populus*. This will broaden the utility of PtrEPSP-TF on enhancing biofuel production, flavonoids production, carben fiber production, and nutritional values of monocot plants, especially food crops. Besides MYB46, the expression of four rice transcription factors controlling cell wall biosynthesis can be regulated by PtEPSP-TF. This will extend the engineering targets to prevent cell wall recalcitrance and promote efficient biofuel production from biomass.

Example 2: Materials and Methods

Plant Growth Conditions

To generate transgenic rice, cDNAs of the archetypic PtrEPSP-TF, the BESC-35 PtrEPSP-TF, and BESC-876 PtrEPSP-TF were cloned into binary vector pANIC10A (Mann, D. G., et al., (2012). *Plant biotechnology journal* 10, 226-236) and then transformed into *Japonica* rice Taipei 309, using biolistics and the procedures as described in Mann et al. 2011 (Mann, D. G., et al., (2011). *BMC biotechnology* 11, 74). The empty pANIC10A vector was transformed in parallel as a negative control. Positive transgenic events were selected by measuring PtrEPSP-TF expression using RT-PCR in hygromycin-resistant plants. RNA was isolated as described (Jacobs, T. B., et al., (2016). *Plant biotechnology journal* 14, 117-127). Total RNA was treated with RNase-free DNase I (Thermo Fisher Scientific). End-point RT-PCR was performed with the GoScript Reverse Transcription System (Promega) according to the manufacturer's instructions using primers EPSP-1219F (5'-GCTATGACTCTGGCTGTTGTTGC-3' (SEQ ID NO: 5) and OCS-R (5'-CAACGTGCACAACAGAATTGA-3' (SEQ ID NO: 6)). Rice plants were grown in soil under natural sunlight in a closed greenhouse at 22-32° C. with controlled water and nutrient supply and a 16-hour light period.

RNA-Seq Experiments

RNAs were extracted from stem tissues of three-month-old rice plants prior to flower emergence (i.e., the vegetative stage). Four biological replicates were collected for each construct. The cDNA libraries were constructed following Illumina standard protocols and sequenced with Illumina HiSeq 2500. After filtering out low-quality reads, RNA-Seq reads were aligned to the *Oryza sativa* genome using TopHat (Kim, D., et al., (2013). *Genome Biol,* 14, R36). Differentially-expressed genes (DEGs) were identified using the R package DESeq2 (Love, M. I., et al., (2014). *Genome Biol.,* 15, 550). Raw p-values were adjusted for multiple comparison effects using the false discovery rate (FDR). The cutoff for significant DEGs was set as >2 absolute fold change (FC) and FDR≤0.05.

Principal components analysis (PCA) was conducted based on the genome-wide gene expression data from all the samples using R software. K-means clustering of DEGs was performed using MeV software (Howe, E. A., et al., (2011). *Bioinformatics,* 27, 3209-3210). Gene Ontology (GO) enrichment analysis was performed for DEGs in each cluster using agriGO (Tian, T., et al., (2017). *Nucleic Acids Res,* 45, W122-W129). A multiple testing correction was performed using the FDR under dependency (Yekutieli, D., and Benjamini, Y. (1999). *Jour. of Stat.l Planning and Inference,* 82, 171-196). GO terms with a corrected p≤0.05 were considered to be significantly enriched. For transcription factor binding sites (TFBS) prediction, 1-kb sequences upstream of the translation start site of DEGs in each cluster were analyzed using PlantPAN (Chow, C. N. et al., (2016). *Nucleic Acids Res.,* 44, D1154-1160).

Metabolite Analysis

Freeze-dried stems were ground with a micro-Wiley mill and ~50 mg DW was subsequently twice extracted with 2.5 mL 80% ethanol overnight and then combined prior to drying a 0.5 ml aliquot in a nitrogen stream. Sorbitol was added before extraction as an internal standard to correct for differences in extraction efficiency, subsequent differences in derivatization efficiency and changes in sample volume during heating. Dried extracts were silylated for 1 h at 70° C. to generate trimethylsilyl (TMS) derivatives, which were analyzed after 2 days with an Agilent Technologies Inc. (Santa Clara, Calif.) 5975C inert XL gas chromatograph-mass spectrometer as described elsewhere (Li, Y., et al., (2012). *Biotechnol Biofuels,* 5, 2; Tschaplinski, T. J., et al., (2012). *Biotechnol Biofuels,* 5, 71). Metabolite peak extraction, identification, and quantification were described previously (Tschaplinski, T. J., et al., (2012). *Biotechnol Biofuels,* 5, 71), and unidentified metabolites were denoted by their retention time as well as key mass-to-charge (m/z) ratios. Data were pooled across lines and treatment means were tested for statistical significance (p≤0.05) using Student's t-tests.

Electrophoretic Mobility Shift Assay (EMSA)

The archetypic PtrEPSP-TF, BESC-35 PtrEPSP-TF, and BESC-876 PtrEPSP-TF were cloned into the pGEX-6P-1 vector (GE Healthcare) by BamHI and EcoRI for GST fusion constructs. The constructs were transformed into *E. coli* strain BL21(DE3)pLysS (Invitrogen) for protein expression. GST fusion proteins were extracted and purified as previously described using Glutathione Sepharose 4B beads (GE Healthcare) (Xie, M., et al., (2012). *Nucleic Acids Res* 40, 4422-4431). To perform EMSA, proteins were then eluted from beads by incubating with Elution Buffer (50 mM Tris-HCl pH 8.0, 10 mM reduced glutathione) at 4° C. for 30 min. For DNA probes, PtrhAT promoter DNA was PCR amplified, gel purified, and end labeled with biotin as described previously (Xie, M., et al., (2018b). *The Plant Cell* 30, 1645-1660). The DNA binding reaction included 0.25 nM Biotin-labeled probe, 0.4 μg of purified protein, 10 mM Tris-HCl (pH 7.5), 50 mM KCl, 1 mM DTT, 2.5% Glycerol, 5 mM $MgCl_2$, 1 μg Poly (dI-dC), 0.05% NP-40. Reactions were incubated at room temperature for 20 min. The reaction mixtures were then resolved in 6% DNA retardation gel (Novex) by electrophoresis at 100 V for 1-2 h and electrophoretically transferred to Nylon membrane. Signals of biotin were detected using Chemiluminescent Nucleic Acid Detection Module (Thermo Scientific) as suggested by manufacturer.

Transcriptional Activity Assay

The protoplast transfection-based transcriptional activity assay was performed according to the previously describe method (Tiwari, S. B., et al., (2003). *Plant Cell* 15, 533-543). Ten μg of effector and reporter plasmids were co-transfected into 100 μl of *Populus* protoplasts using PEG-calcium transfection method and incubated under the darkness for 18-20 h at room temperature. GUS activity assay was performed as described (Yoo, S. D., et al., (2007). *Nat Protoc* 2, 1565-1572). GUS activity was measured using a Fluoroskan microplate reader. To normalize GUS activity, 100 ng of 35S: Luciferase plasmid was co-transfected for each transfection. Luciferase activity was measured using Promega Luciferase Assay System according to the manufacturer's manual.

Phloroglucinol-HCl Staining

Stems of rice were sectioned into 60 μm thickness and then stained with 1% phloroglucinol in HCl for 5 min and immediately observed under a light microscope (Ziess). The internal diameters of sclerenchyma cells were measured under microscope using the manufacturer's software (Ziess).

Co-Expression Analysis

The microarray data of rice was downloaded from the NCBI GEO database under the series accession numbers GSE19024 (190 samples corresponding to 39 tissues from two indica varieties; Minghui 63 and Zhenshan 97) (Wang, L., et al., (2010). *Plant J* 61, 752-766), and GSE51289 (59 samples corresponding to 20 data points of internodes during secondary cell wall formation and 143 samples corresponding to 48 tissue and organ types) (Hirano, K., et al., (2013). *Plant and Cell Physiology* 54, 1803-1821). For co-expression analysis, a matrix of DEGs in the RNA-Seq was constructed by calculating pairwise Pearson correlation coefficients (PCC) based on the normalized expression data across all samples from GSE19024 and GSE51289. Cytoscape (Shannon, P., et al., (2003). *Genome Res* 13, 2498-2504) was used to visualize the resulting network. Only co-expression relationships with p≤0.05 were indicated in the network.

Example 3: BESC-35 and BESC-876

In genome-wide association studies, it was discovered that BESC-35 and BESC-876 are two rare variants at the PtrEPSP-TF loci. Compared to alternate homozygous alleles, the lignin content of BESC-35 and BESC-876 exhibits significant reduction in the Native environment (FIG. 1, 18% versus 23%), which will reduce cell wall recalcitrance and increase sugar release and ethanol production. At the molecular level, the amino acids substitution at position 142 and 364 results in impaired DNA binding and transcription activity of the two loss of function alleles.

Figure 2A:
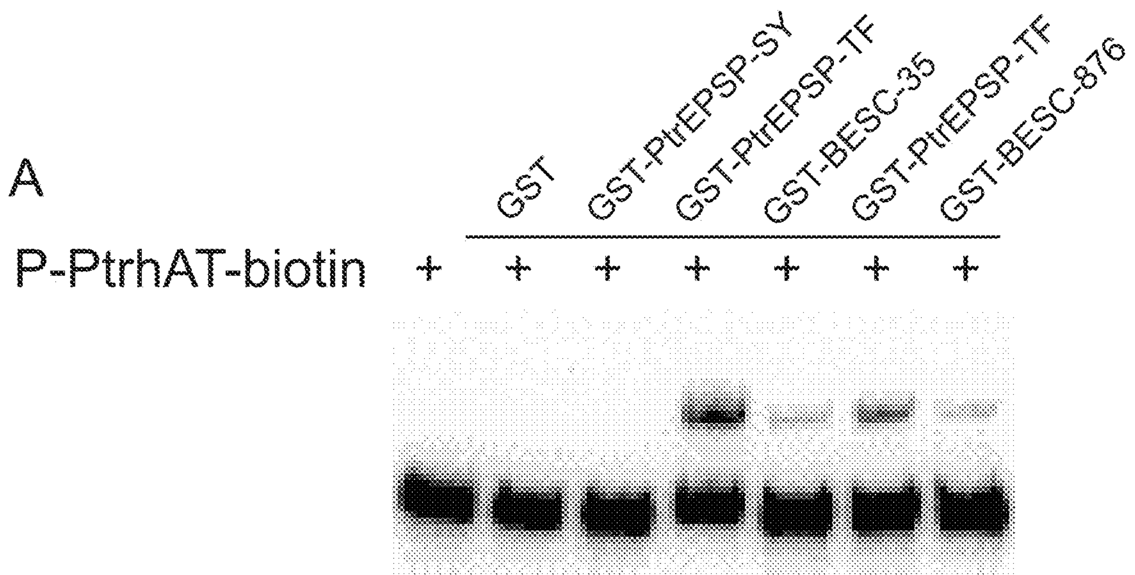
FIGS. 2A-2B. (A) Electrophoretic mobility shift assay (EMSA) shows that BESC-35 (lane 5) and BESC-876 (lane 7) have reduced DNA binding activity. (B) BESC-35 (Bar 4) and BESC-876 (Bar 6) have impaired transcriptional repression activity. Transcriptional repression of PtrhAT (the target of PtrEPSP-TF) is analyzed in protoplasts. PtrEPSP-TF can repress PtrhAT promoter and reduce GUS expression (Bar 3 and 5), but BESC-35 (Bar 4) and BESC-876 (Bar 6) cannot.
Figure 2B:
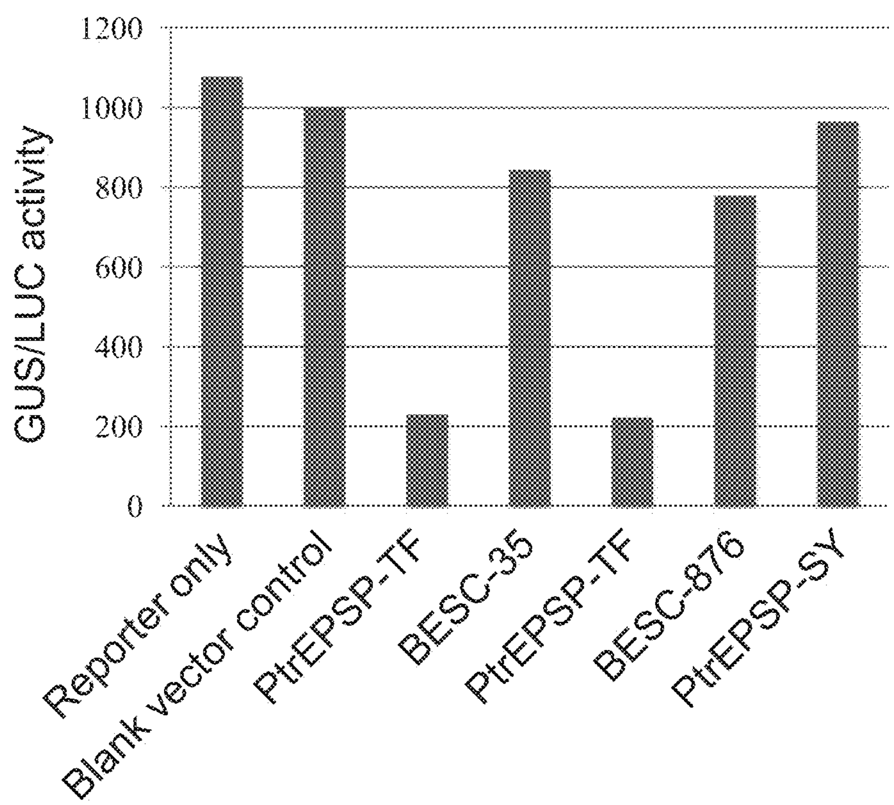

To confirm that BESC-35 and BESC-876 are loss of function alleles of PtrEPSP-TF at molecular level, the inventors examined their DNA binding activity and transcription activity, which are critical for the transcriptional functions of PtrEPSP-TF. Compared to wild-type PtrEPSP-TF, the binding affinity to PtrhAT promoter DNA of BESC-35 and BESC-876 is significantly reduced in the analysis of electrophoretic mobility shift assay (EMSA) (FIG. 2A). The transcriptional repression activity on PtrhAT promoter is almost abolished for BESC-35 and BESC-876 (FIG. 2B). These results provide strong evidence that BESC-35 and BESC-876 are loss of function alleles of PtrEPSP-TF. To determine the molecular basis of changed DNA binding and transcription activity of BESC-35 and BESC-876, amino acid sequence analysis was performed on BESC-35 and BESC-876 proteins. The analysis results show that BESC-35 protein has one amino acids substitution: Aspartic acid at position 142 is substituted with Glutamic acid. For BESC-876, two amino acids are substituted: Aspartic acid at position 142 changes to Glutamic acids, Leucine at position 364 changes to Proline. Therefore, the amino acids at position 142 and 364 are critical for DNA binding activity and transcriptional activity of PtrEPSP-TF. Substitutions at the two positions will impair PtrEPSP-TF transcriptional regulator function.

Figure 3:
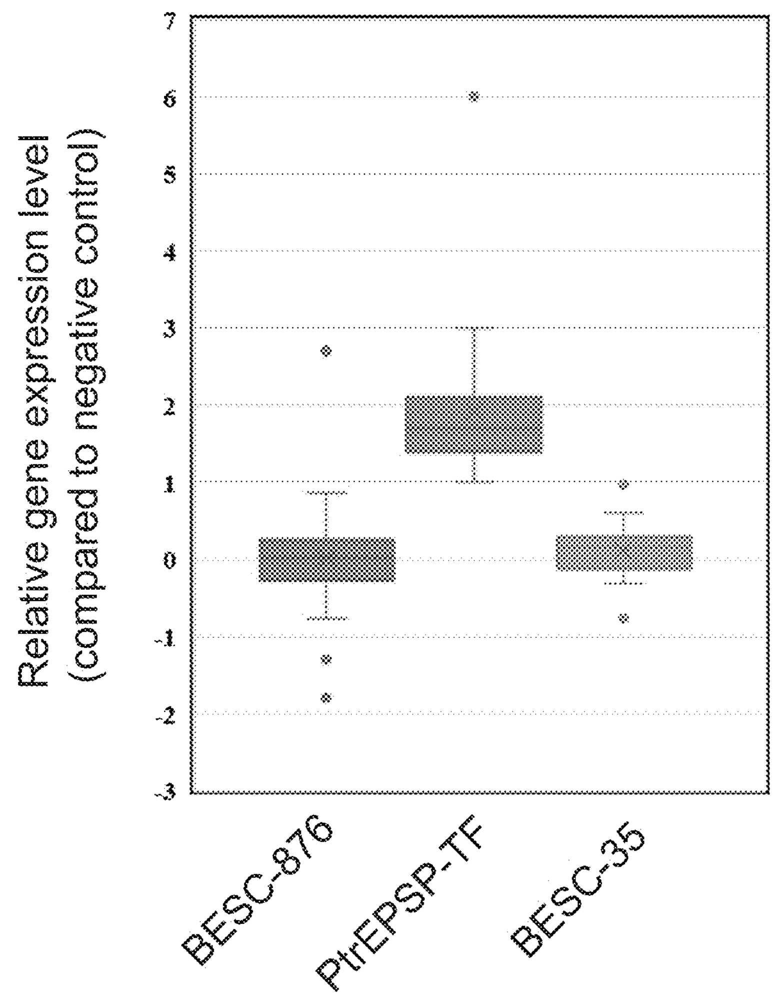
FIG. 3. Expression level changes of cell wall synthesis genes. Plants overexpressing PtrEPSP-TF have increased expression levels of cell wall synthesis genes (orange color). Plants overexpressing BESC-35 and BESC-876 variants have no significant difference in the expression level compared to negative control.
Figure 4:
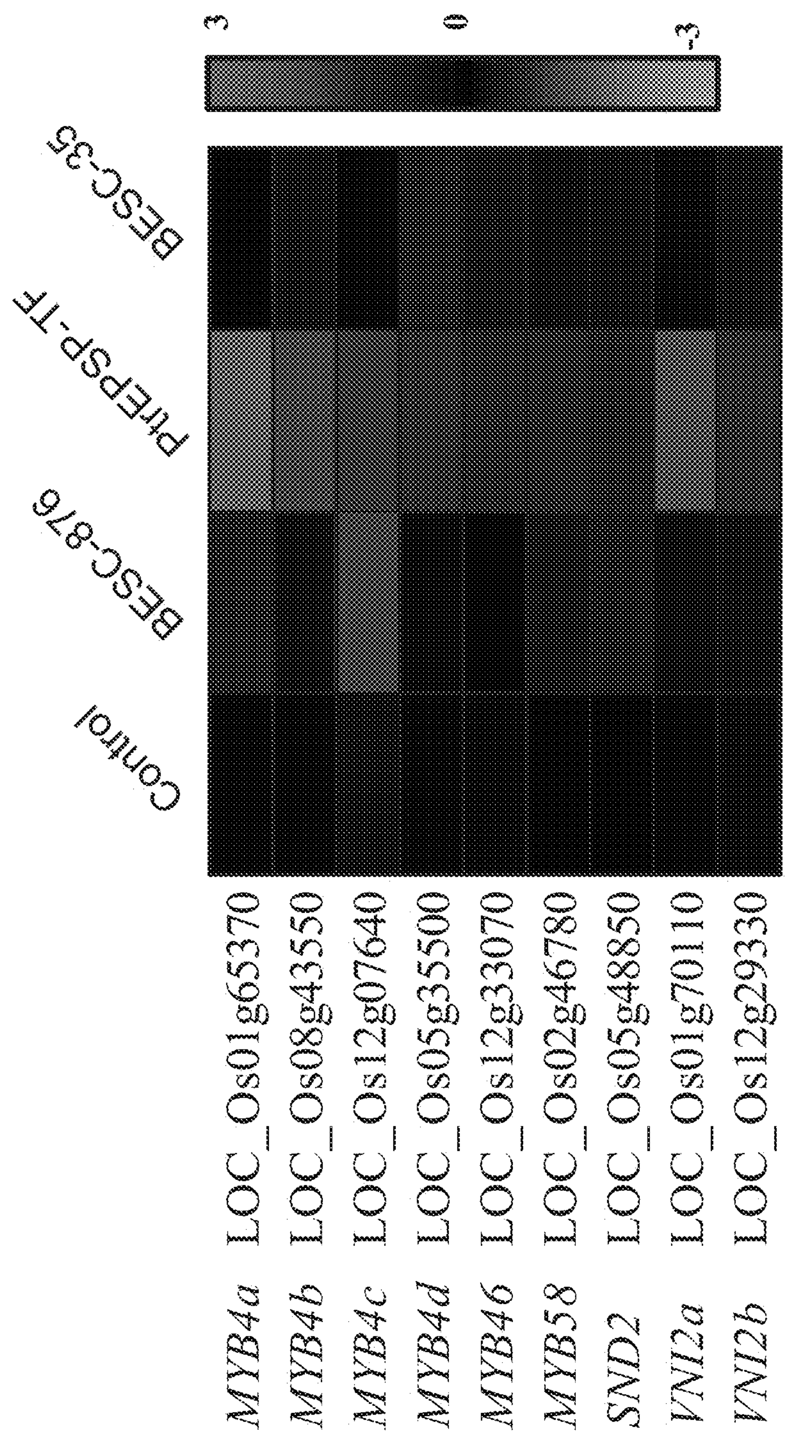
FIG. 4. The expression levels of MYB46, MYB4, MYB48, SND2, and VNI2 are up-regulated in rice plants overexpressing PtrEPSP-TF. Green color represents down-regulation, red color represents up-regulation.

To evaluate effects of PtrEPSP-TF on monocot plants, transgenic rice plants overexpressing PtrEPSP-TF, BESC-35 (PtrEPSP-TF$^{D142E}$), and BESC-876 (PtrEPSP-TF$^{D142E/L364P}$) were generated. Then, RNA-seq was used to analyze transcript profiles in each plant. By comparing with the transcript profile of rice transfected with empty vector, it was found that expression levels of cell wall synthesis genes are up-regulated in plants overexpressing PtrEPSP-TF, but not plants overexpression loss of function alleles (FIG. 3). These results suggest that PtrEPSP-TF also affects cell wall biosynthesis in monocot plants. Beyond cell wall synthesis genes, the expression level of rice MYB46, the master regulator of secondary cell wall biosynthesis and secondary metabolic pathways, is increased in rice plants overexpressing PtrEPSP-TF (FIG. 4). These results provide strong evidence that PtrEPSP-TF transcriptional regulates cell wall synthesis and secondary metabolic pathways via modulating the expression of key regulator MYB46 in rice, which is the same mechanism in *Populus*.

To discover broader impact of PtrEPSP-TF on rice transcript profiles, the expression levels of other transcription factors were determined and four new targets of PtrEPSP-TF were identified in rice: MYB4, MYB58, SND2, and VIN2. The expression levels of all the four transcription factors are increased by overexpressing PtrEPSP-TF (FIG. 4). Whereas, BESC-35 and BESC-876 have no effect on the expression level of the four transcription factors (FIG. 4). Because the four transcription factors are key regulators of secondary cell wall biosynthesis, the regulation of secondary cell wall biosynthesis by PtrEPSP-TF is not limited to modulating the expression of MYB46.

Figure 5A:
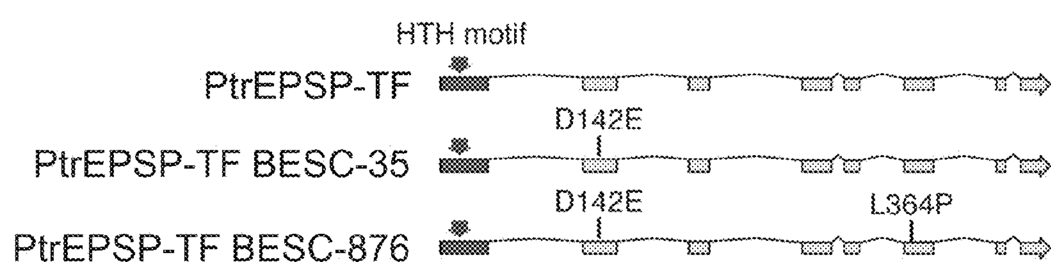
FIGS. 5A-5C. The reduced DNA binding and transcriptional activities of BESC-35 and BESC-876 variants. (A) A scheme of point mutations in BESC-35 and BESC-876 variants. The HTH motif is indicated by a red arrow. Amino acid abbreviation: D, Aspartic acid; E, Glutamic acid; L, Leucine; P, Proline. (B) BESC-35 and BESC-876 variants display reduced DNA binding affinity to PtrhAT promoter. Left panel: purified GST, GST-PtrEPSP-SY (an ESPS homolog of PtrEPSP-TF that lacks the HTH domain), GST-PtrEPSP-TF, GST-PtrEPSP-TF from BESC-35, and GST-PtrEPSP-TF from BESC-876 were resolved in SDS-PAGE gel and stained with Coomassie Blue. Right panel: EMSA assay of DNA binding to biotin-labeled PtrhAT promoter. Free probe and GST are negative controls. (C) Transactivation assay of repression activities of archetypic PtrEPSP-TF, BESC-35 PtrEPSP-TF, and BESC-876 PtrEPSP-TF on PthAT promoter. The repression activity of the blank vector was analyzed in parallel as a negative control. All transfection assays were performed in triplicate. P-value comparison is calculated using two-tailed Student t-tests (** $p \leq 0.01$, * $p \leq 0.05$, ns $p>0.05$).

Example 4: DNA Binding and Transcriptional Activities of Allelic Variants from BESC-35 and BESC-876 are Impaired The inventors previously identified two *Populus* natural variants containing PtrEPSP-TF rare alleles: BESC-35 and BESC-876 that showed reduced lignin content compared with the average of the *Populus trichocarpa* population (Xie, M., et al., (2018). *The Plant Cell* 30, 1645-1660). To determine how mutations in these genotypes affect PtrEPSP-TF protein function, the inventors cloned PtrEPSP-TF allelic variants from both genotypes. Sequencing and amino acid alignments revealed that both BESC-35 and BESC-876 variants carry a point-mutation that results in the substitution of the 142$^{nd}$ amino acid from aspartic acid (D) to glutamic acid (E) (D142E, FIG. 1A). BESC-876 has an additional point mutation at position 364 that leads to the substitution of leucine (L) with proline (P) (L364P, FIG. 5A).

Figure 5B:
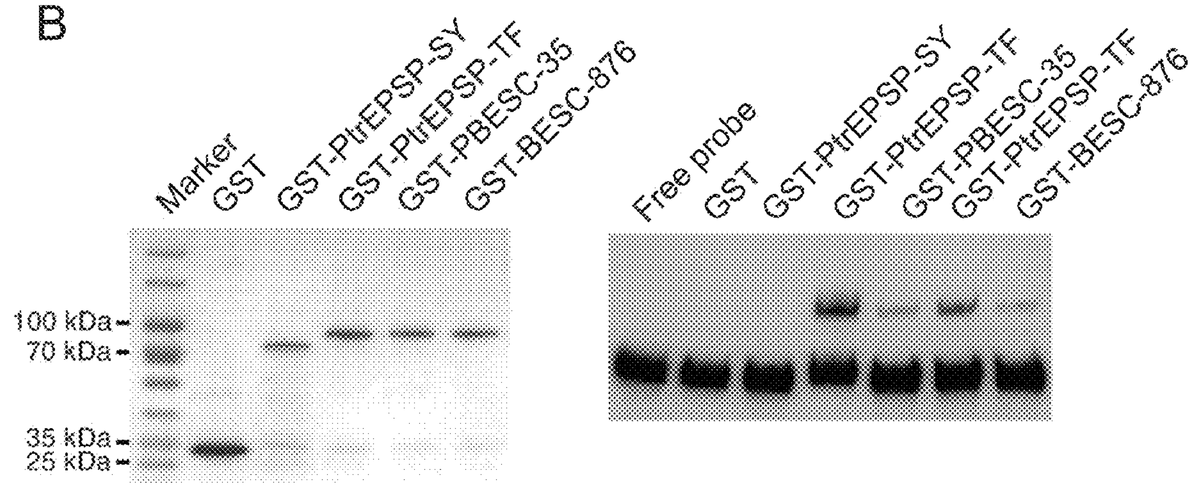
Figure 5C:
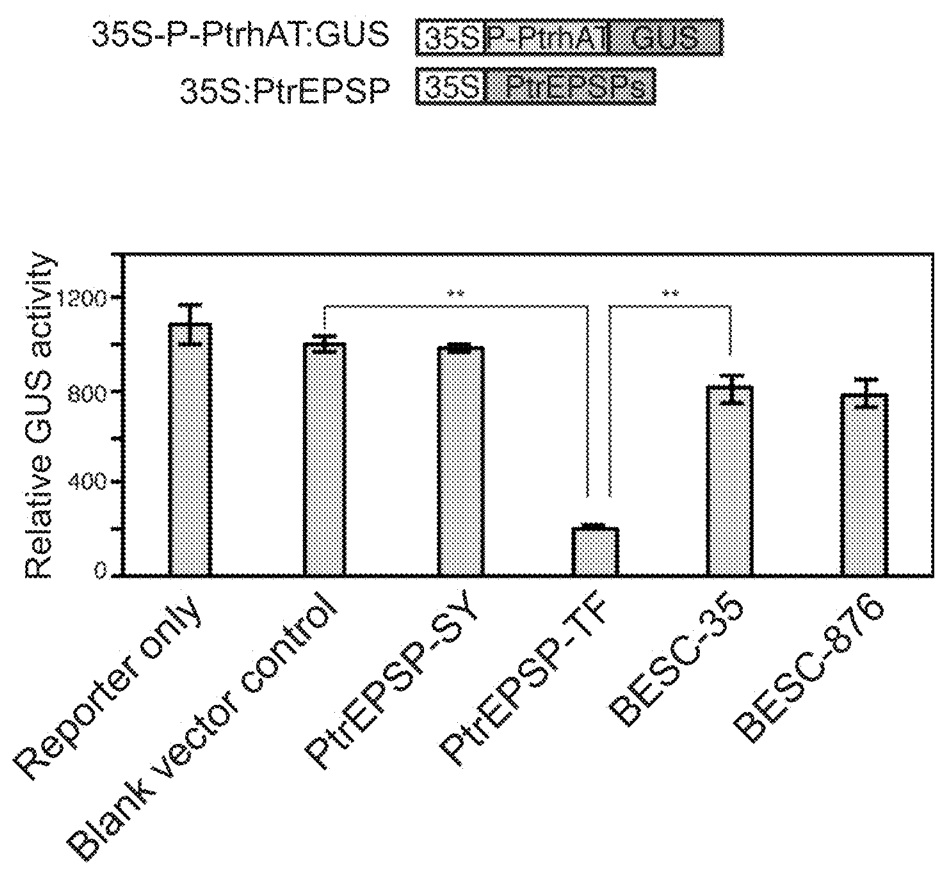

Given that the HTH motif (amino acids 30-70) is responsible for DNA binding and transcriptional activity of PtrEPSP-TF (Xie, M., et al., (2018). *The Plant Cell* 30, 1645-1660), the inventors speculated that the amino acid substitution adjacent to the HTH motif (i.e., D142E) may affect the transcriptional function of PtrEPSP-TF. To examine this possibility, the inventors analyzed the binding affinity of BESC-35 and BESC-876 variants to the promoter of PtrhAT, which is the direct regulatory target of PtrEPSP-TF in *Populus* (Xie, M., et al., (2018). *The Plant Cell* 30, 1645-1660). PtrEPSP-TF and the variant proteins were tagged with GST and expressed in *E. coli*. After purification, these proteins were subjected to in vitro electrophoretic mobility shift assay (EMSA) to determine their binding affinities to the PtrhAT promoter, which was labeled with biotin for visualization. As shown in FIG. 5B, signals of shift bands of both variants were dramatically reduced compared with that of the archetypic PtrEPSP-TF. These results demonstrate that BESC-35 and BESC-876 variants have significantly reduced DNA binding activity. Consistent with reduced DNA binding activity, both PtrEPSP-TF variants display impaired transcriptional repression on the PthAT promoter (FIG. 5C). In contrast to the archetypic PtrEPSP-TF, neither BESC-35 nor BESC-876 variants can reduce the expression of the GUS gene downstream of the PtrhAT promoter in the transactivation assays using the protoplast transient expression system. Thus, the BESC-35 and BESC-876 allelic variants carry mutations impacting the transcriptional repressor activity of PtrEPSP-TF. Given the promoting effects of the archetypic PtrEPSP-TF allele on PtrMYB021 (MYB46 close homolog (Wilkins, O., et al., (2009). *Plant Physiology* 149, 981-993)) expression and lignin biosynthesis in *Populus*, the reduced lignin content of BESC-35 and BESC-876 *Populus* genotypes is likely due to the impaired function of PtrEPSP-TF. As such, BESC-35 and BESC-876 variants can be viewed as loss-of-function alleles of PtrEPSP-TF.

Figures 6A, 6B:
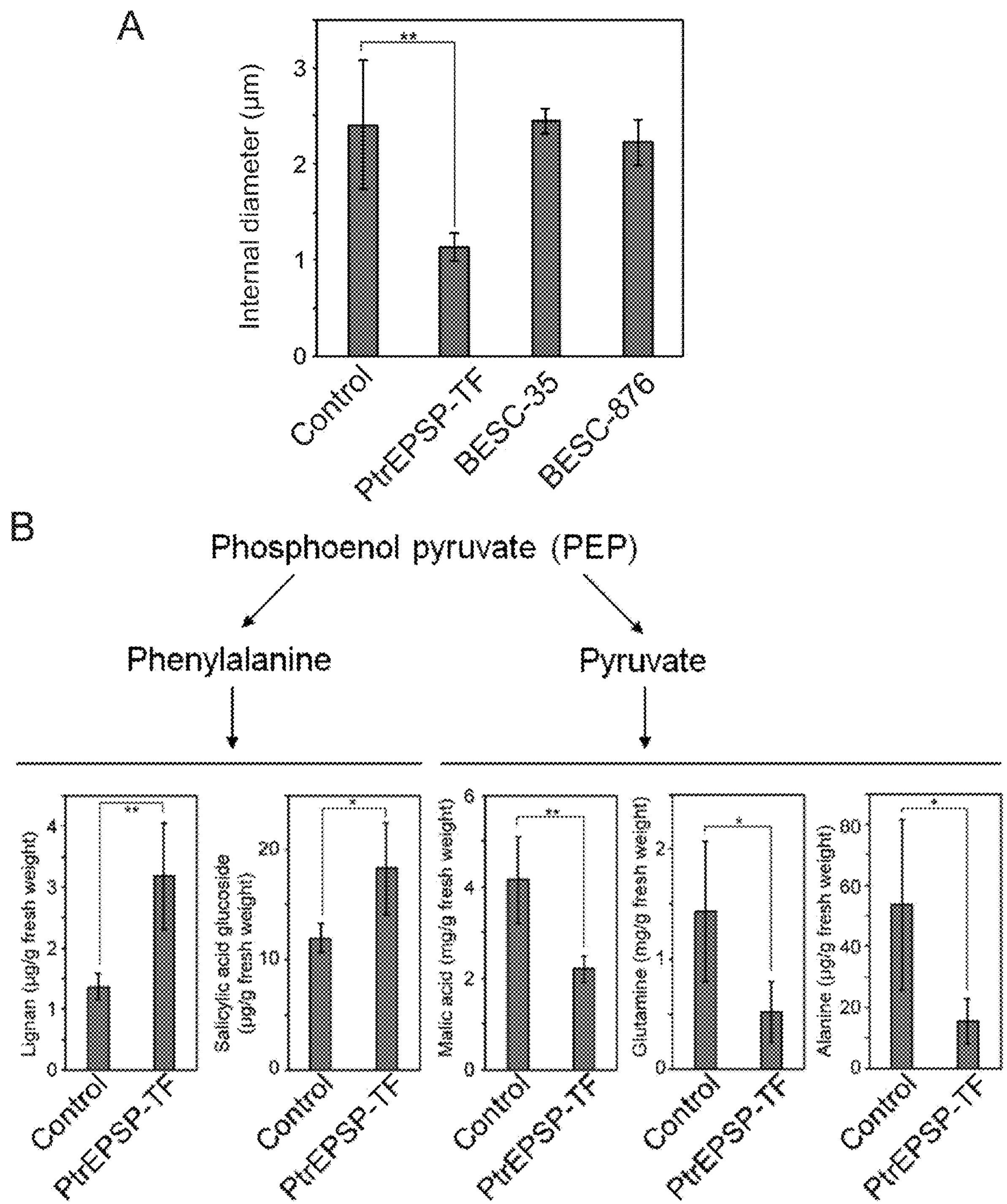
FIGS. 6A-6B. Transgenic rice plants expressing PtrEPSP-TF display thickened sclerenchyma and altered secondary metabolism. (A) The Sclerenchyma cells of PtrEPSP-TF have smaller internal diameter. The internal diameters of ten sclerenchyma cells were measured under a microscope to calculate mean values and standard errors (error bars). P-value comparison was calculated using two-tailed Student t-tests (** $p \leq 0.01$, * $p \leq 0.05$, ns $p>0.05$). (B) Rice plants expressing functional archetypic PtrEPSP-TF have increased accumulation of phenylpropanoid metabolites, but reduced accumulation of pyruvate metabolites. Four independent replicates were measured to calculate mean values and standard errors (error bars). P-value comparison was calculated using two-tailed Student t-tests (** $p \leq 0.01$, * $p \leq 0.05$, ns $p>0.05$).

Example 5: Heterologous Expression of PtrEPSP-TF in Transgenic Rice Alters Sclerenchyma Thickening and Secondary Metabolism The absence of the HTH motif in monocot EPSP synthases (Xie, M., et al., (2018). The Plant Cell 30, 1645-1660) prompted us to compare functions of archetypic PtrEPSP-TF with BESC-35 and BESC-876 variants via heterologous expression. Transgenic rice plants heterogeneously expressing the functional PtrEPSP-TF, or the BESC-35 (PtrEPSP- $TF^{D142E}$) and BESC-876 ($PtrEPSP-TF^{D142E/L364P}$) variants were generated. To visualize secondary cell walls, transverse cross sections of the S8 segment of rice internode II (Lin, F., et al., (2017). *Front Plant Sci.* 8, 1134) were stained with phloroglucinol-HCl, which turns lignin into a red-purple color. Under a low-magnification dissecting microscope, each sclerenchyma cell of the empty-vector control was clearly observed, and their cell walls were stained red. Different from the empty-vector control, the whole sclerenchyma cell region of rice plants expressing the archetypic PtrEPSP-TF stained red and it was hard to distinguish individual sclerenchyma cells. On the other side, transgenic rice plants expressing $PtrEPSP-TF^{D142E}$ and $PtrEPSP-TF^{D142E/L364P}$ variants exhibit similar staining results as that of the empty-vector control, suggesting the difference of sclerenchyma cell staining is likely induced by difference in functions between PtrEPSP-TF and $PtrEPSP-TF^{D142E}$ or $PtrEPSP-TF^{D142E/L364P}$. To further determine the cause of the difference of sclerenchyma cell staining, the inventors observed stained stems using a high-magnification compound microscope. Expression of the functional PtrEPSP-TF resulted in thickened secondary cell walls and reduced internal diameter in the sclerenchyma cells that form the cortical layers in bundle sheath fibers surrounding vascular vessels (FIG. 6A). In contrast, $PtrEPSP-TF^{D142E}$ and $PtrEPSP-TF^{D142E/L364P}$ variants resulted in little differences from the empty-vector control in the thickness of secondary cell walls of the sclerenchyma cells (FIG. 6A). Unexpectedly, the secondary cell wall thickening induced by the archetypic PtrEPSP-TF suggested that PtrEPSP-TF may affect the transcriptional regulation of secondary cell wall biosynthesis in rice as it does in *Populus*, although the EPSP form found in rice lacks the HTH domain and thus lacking transcriptional control.

Besides sclerenchyma thickening, the lignin content of rice expressing archetypic PtrEPSP-TF (31.98±0.24 (% of dry weight)) was significantly higher ($p \leq 0.01$) than that of the empty-vector control (29.11±0.00 (% of dry weight)). Gas chromatography mass spectrometry (GC-MS) analysis revealed that secondary metabolism of transgenic rice was altered by archetypic PtrEPSP-TF, where metabolites in the phenylalanine branch (FIG. 6B), including salicylic acid glucoside exhibited 52.3% (p=0.028) and lignan exhibited 132.5% (p=0.007) increases, respectively, relative to the empty-vector controls (FIG. 6B). This same response occurred in *Populus* over-expressing PtrEPSP-TF (Xie, M., et al., (2018). The Plant Cell 30, 1645-1660). Oppositely, metabolites in the pyruvate branch (FIG. 6B), including malic acid, alanine, and glutamine, exhibited significant reductions, 46.8% (p=0.008), 63.8% (p=0.039), and 71.3% (p=0.037) respectively, in rice expressing PtrEPSP-TF (FIG. 6B). Since phenylalanine and pyruvate are synthesized using the same precursor phosphoenol pyruvate (PEP) (Davies, 1979) and phenylalanine is the precursor of the phenylpropanoid pathway (Fraser, C. M., and Chapple, C. (2011). *Arabidopsis* Book 9, e0152), these metabolic changes suggest that PtrEPSP-TF can guide carbon flux into the phenylpropanoid pathway in rice.

Figure 7A:
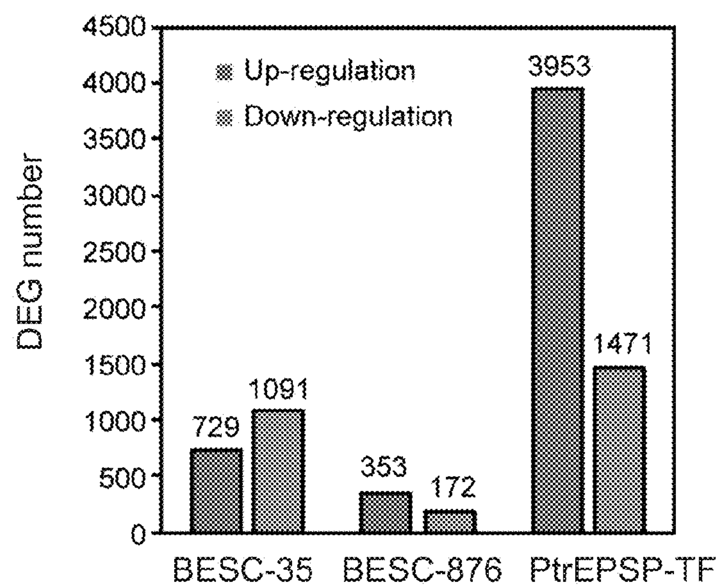
FIGS. 7A-7B. The heterologous expression of the archetypic PtrEPSP-TF in rice induces the up-regulation of genes involved in lignin and secondary cell wall biosynthesis. (A) Rice plants expressing archetypic PtrEPSP-TF have more DEGs than rice plants expressing BESC35 PtrEPSP-TF or BESC876 PtrEPSP-TF. Red bar: up-regulated genes; Green bar: down-regulated genes. (B) Heat map showing expression patterns of PAL, C4H, 4CL, CAD, FSH, LACCASE, CESA4, IRX9, MYB46/83, MYB58/63, MYB20/43, and SND2/3 in four independent replicates (R1 to R4) of the archetypic PtrEPSP-TF expression rice. $Log_2FC$ of mean expression levels of the four replicates of empty vector control was set as 0. The color scale represents the value of $Log_2$ FC.

Example 6: Heterologous Expression of PtrEPSP-TF in Rice Alters Transcriptional Regulation of the Phenylpropanoid Pathway To explore the molecular effects of the archetypic PtrEPSP-TF in transgenic rice, the inventors extracted total RNAs from stems of three-month-old transgenic rice plants and performed RNA-seq analysis. For each sample, four biological replicates were analyzed, and highly consistent results were obtained (Pearson correlation $r \geq 0.93$). Differential expression analysis identified a large collection of mRNAs whose abundance was significantly affected (Fold change≥2, $p \leq 0.01$, false discovery rate [FDR]≤0.05) by the archetypic PtrEPSP-TF. Compared with transcriptomes of empty-vector control, a total of 3,953 up-regulated genes and 1,471 down-regulated genes were identified (FIG. 7A). Consistent with results that the $PtrEPSP-TF^{D142E}$ and $PtrEPSP-TF^{D142E/L364P}$ variants have impaired DNA binding and transcriptional repressor activity, DEGs in BESC-35 and BESC-876 variants expression lines were far fewer compared to the functional archetypic PtrEPSP-TF (FIG. 7A). The BESC-35 variant led to 729 up-regulated genes and 1,091 down-regulated genes, whereas the BESC-876 variant resulted in 353 up-regulated and 172 down-regulated genes (FIG. 7A). In addition, among the 3,953 up-regulated genes by the archetypic PtrEPSP-TF, only 134 of them (3.39%) were also up-regulated by BESC-35 and BESC-876 variants. Similarly, only 1.63% (24 out of 1,471) down-regulated genes by the archetypic PtrEPSP-TF were down-regulated by BESC-35 and BESC-876 variants.

The inventors then performed Gene Ontology (GO) enrichment analysis on DEGs of rice expressing the functional archetypic PtrEPSP-TF to determine the global effect of PtrEPSP-TF. Among up-regulated ones, genes associated with cell walls, lipids, secondary metabolism, and light reactions were significantly enriched. Further GO enrichment analysis showed that genes involved in phenylpropanoid, flavonoid, and lignin metabolism were overrepresented among up-regulated genes associated with secondary metabolism. In contrast, down-regulated genes did not show any enrichment in metabolic pathways.

Figure 7B:
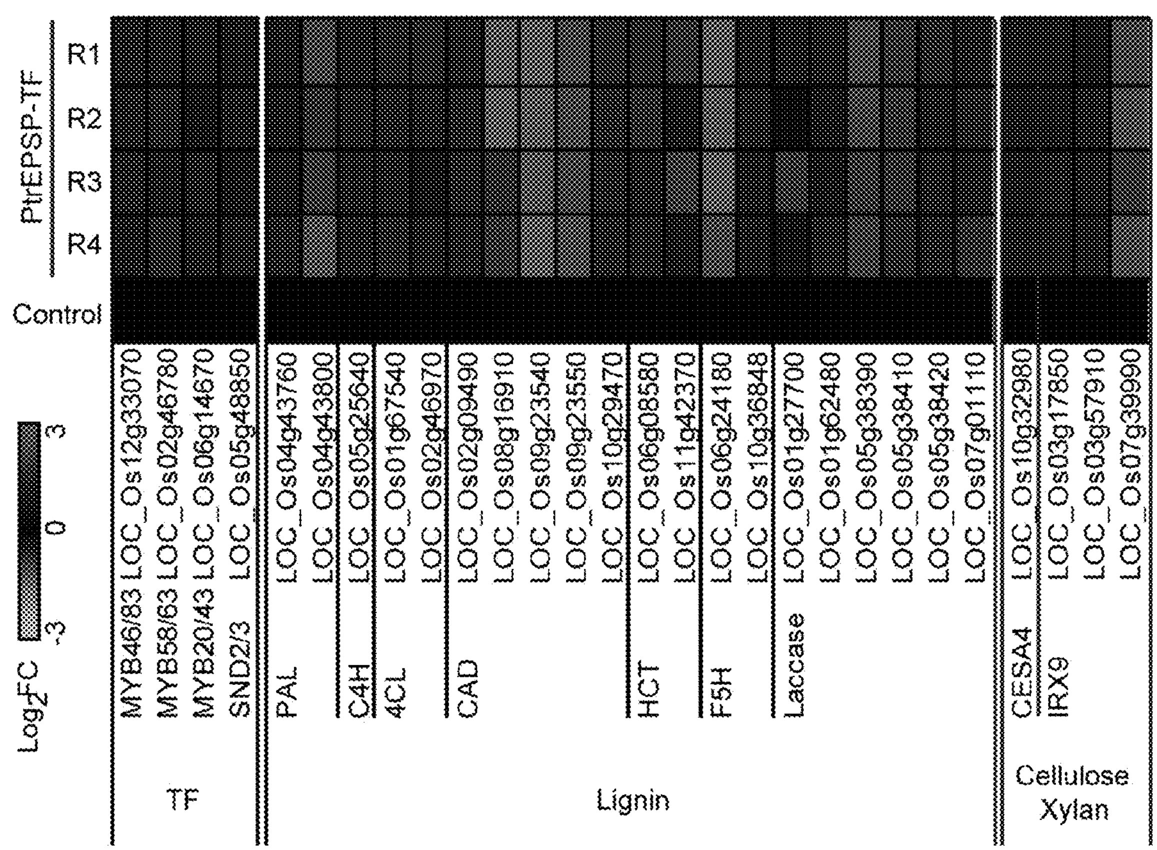

To determine whether the differential sclerenchyma cell staining between the functional PtrEPSP-TF and BESC-35 and BESC-876 variants was related to transcriptional reprogramming of secondary cell wall biosynthesis, the inventors looked for genes related to secondary cell wall biosynthesis from DEGs of transgenic rice. A total of twenty lignin, one cellulose and three xylan biosynthetic genes were found. Interestingly, four master regulators of secondary cell wall biosynthesis were also found (FIG. 7B). All of these were up-regulated by the functional PtrEPSP-TF (FIG. 7B). In contrast, expression of these genes only showed modest up-regulation or even down-regulation in the BESC-35 and BESC-876 lines, suggesting that archetypic PtrEPSP-TF, but not loss-of-function alleles, can trigger the transcriptional reprogramming of secondary cell wall biosynthesis in rice.

Among these 28 up-regulated genes involved in secondary cell wall biosynthesis, four genes encode transcription factors (FIG. 7B), and their *Arabidopsis* homologs were found to be master regulators of secondary cell wall/lignin biosynthesis, including LOC_Os12g33070 (MYB46/83) (Zhong, R., et al., (2011). *Plant Cell Physiol* 52, 1856-1871), LOC_Os02g46780 (MYB58/63) (Zhou, J., et al., (2009). *Plant Cell* 21, 248-266), LOC_Os06g14670 (MYB20/43) (Zhong, R., et al., (2008). *Plant Cell* 20, 2763-2782), and LOC_Os05g48850 (SND2/3) (Hussey, S. G., et al., (2011). *BMC Plant Biol* 11, 173). Downstream of these transcription factors, PAL, C4H, and 4CL catalyze the first three steps of the phenylpropanoid pathway and are essential for the biosynthesis of monolignols (Fraser, C. M., and Chapple, C. (2011). *Arabidopsis Book,* 9, e0152). The inventors observed that two PAL genes (LOC_Os04g43760 and LOC_Os04g43800), one C4H gene (LOC_Os05g25640), and two 4CL genes (LOC_Os01g67540 and LOC_Os02g46970) were up-regulated by the archetypic PtrEPSP-TF (FIG. 7B). In addition, genes critical for monolignol biosynthesis were also up-regulated by the archetypic PtrEPSP-TF, such as five CADs (LOC_Os02g09490, LOC_Os08g16910, LOC_Os09g23540, LOC_Os09g23550, and LOC_Os10g29470), two HCTs (LOC_Os06g08580 and LOC_Os11g42370), and two F5Hs (LOC_Os06g24180 and LOC_Os10g36848) (FIG. 7B). Additionally, six Laccase genes were up-regulated by PtrEPSP-TF: LOC_Os01g27700, LOC_Os01g62480, LOC_Os05g38390, LOC_Os05g38410, LOC_Os05g38420, and LOC_Os07g01110 (FIG. 3B). The four cellulose and xylan biosynthetic genes up-regulated by PtrEPSP-TF were CESA4 (LOC_Os10g32980) and IRX9 (LOC_Os03g17850, LOC_Os03g57910, and LOC_Os07g39990) (FIG. 3B).

Collectively, the inventors demonstrated that the heterologous expression of PtrEPSP-TF in rice resulted in the thickening of secondary cell wall and increased lignin content, which may be through transcriptional reprogramming of genes critical for lignin/secondary cell wall biosynthesis in rice. This observation is consistent with the analysis of transgenic *Populus* over-expressing PtrEPSP-TF (Xie, M., et al., (2018). *The Plant Cell* 30, 1645-1660), suggesting that besides *Populus*, PtrEPSP-TF is capable of affecting the lignin/secondary cell wall biosynthesis when introduced to rice in which the native rice EPSP synthase lacks the HTH domain.

Example 7: PtrEPSP-TF Mediates a Transcriptional Regulatory Network in Rice

In *Populus*, the archetypic PtrEPSP-TF positively regulates PtrMYB021 expression by directly repressing the expression of PtrhAT, a SLEEPER-like gene that directly represses PtrMYB021 expression (Xie, M., et al., (2018). *The Plant Cell,* 30, 1645-1660). As a close homolog of *Arabidopsis* MYB46, a master regulator of secondary cell wall biosynthesis, PtrMYB021 functions as a transcriptional activator and activates the biosynthesis pathways for lignin, cellulose, and xylan (Zhong, R., et al., (2013). *PLoS One* 8, e69219), the major components of secondary cell walls. Similarly, the inventors demonstrate that the archetypic PtrEPSP-TF is able to up-regulate rice MYB46 (LOC_Os12g33070) and phenylpropanoid/lignin biosynthetic genes (PAL, 4CL, C4H, FSH, CAD, CCR, and LACCASE) when introduced to rice. Therefore, the inventors hypothesized that an analogous PtrEPSP-TF-mediated transcriptional mechanism, in which PtrEPSP-TF represses negative regulators to activate lignin/secondary cell wall biosynthesis, may exist in rice.

Figure 8A:
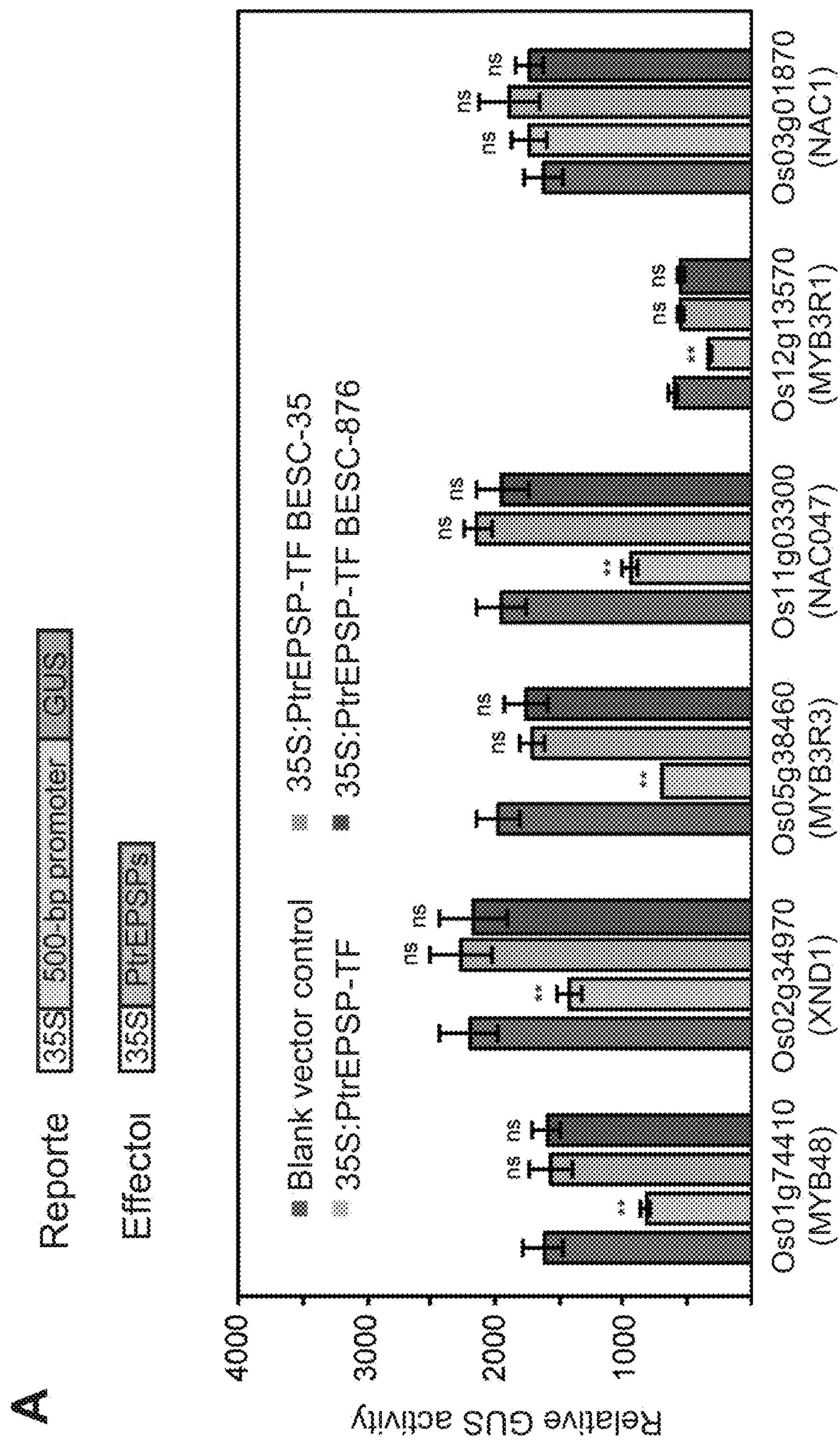
FIGS. 8A-8B. The model of PtrEPSP-TF-mediated transcriptional network regulating lignin and secondary cell wall biosynthesis of rice. (A) Left panel: a scheme of reporter and effector constructs used in transactivation assays. Right panel: transactivation assays determining the transcriptional repression of PtrEPSP-TF on LOC_Os02g34970 (XND1), LOC_Os01g74410 (MYB48), LOC_Os12g13570 (MYB3R1), LOC_Os05g38460 (MYB3R3), and LOC_Os11g03300 (NAC047). All transfection assays were performed in triplicate. P-value comparison with blank vector control was calculated using two-tailed Student t-tests (** $p \leq 0.01$, * $p \leq 0.05$, ns $p>0.05$). (B) Co-expression analysis of members in PtrEPSP-TF-mediated transcriptional network. For co-expression relationships, only $|r|>0.1$ and $p \leq 0.05$ are shown. Black edges indicate experimentally validated relationships. Red edges indicate positive co-relationship. Green edges indicate negative co-relationship. The strength of co-relationship is represented by the thickness of edges.
Figure 8B:
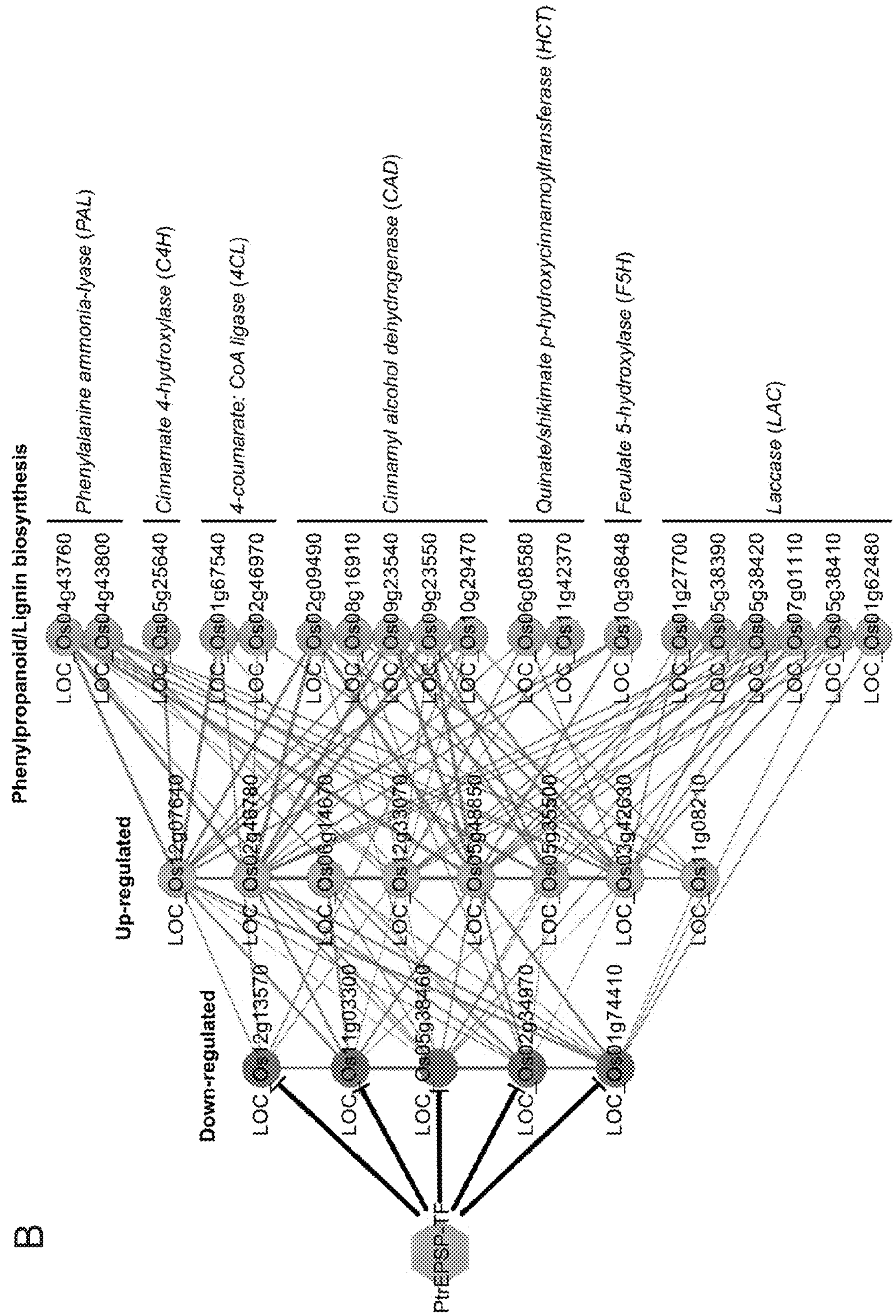

In support of this hypothesis, the inventors found three tandemly duplicated hAT SLEEPER-like genes, LOC_Os09g21410 (−7.3, p=0.0049), LOC_Os09g21420 (−3.1, p=2.7E-11) and LOC_Os09g21430 (−1.7, p=1.1E-06), that were significantly down-regulated in the functional PtrEPSP-TF expression lines. Besides hAT SLEEPER-like genes, the inventors found an additional 82 transcription factors that were significantly down-regulated in the same line. Among them, the inventors found twelve NAC and MYB transcription factors. Among the twelve NAC and MYB transcription factors, XND1 (LOC_Os02g34970) is a homolog of *Arabidopsis* AT5G64530, which has been reported to negatively regulate lignin biosynthesis (Zhao, C., et al., (2008). *Plant J* 53, 425-436). MYB48 (LOC_Os01g74410) has a close homolog MYB12 in *Arabidopsis*, which was found to activate the biosynthesis of flavonoids, which, interestingly, competes for precursors with the biosynthesis of monolignols (Mehrtens, F., et al., (2005). *Plant physiology* 138, 1083-1096). Also, MYB3R1 (LOC_Os12g13570 and AT4G32730 in *Arabidopsis*) and MYB3R3 (LOC_Os05g38460 and AT3G09370 in *Arabidopsis*) are putative transcriptional repressors (Kobayashi, K. et al., (2015). *EMBO J* 34, 1992-2007) and NAC047 (LOC_Os11g03300 and AT3G04070 in *Arabidopsis*) is associated with cell wall re-organization (Rauf, M., et al., (2013). *Plant Cell* 25, 4941-4955). To determine whether these five transcription factors (XND1, MYB48, MYB3R1, MYB3R3, and NAC047) are indeed targets of PtrEPSP-TF in rice, the inventors tested the repression of their promoter activity by PtrEPSP-TF using the *Populus* mesophyll protoplast transient expression system. A 500-bp fragment of the promoter region of each putative target gene (−500 to −1 from start codon) was inserted between the 35S promoter and the GUS gene in reporter constructs. Then each reporter construct was co-transfected with the effector construct expressing PtrEPSP-TF into protoplasts. GUS activity was measured to represent the activity of the tested promoters. As illustrated by the reduced GUS activity, PtrEPSP-TF repressed the activity of all five tested promoters (FIG. 8A). The combined RNA-seq and transactivation assay results demonstrate that expression of the five NAC and MYB transcription factors was negatively regulated by PtrEPSP-TF (FIG. 8B).

The observed repression of SLEEPER-like genes in addition to known negative regulators of cell wall biosynthesis, such as XND1, is consistent with the proposed transcriptional regulatory model in *Populus* (Xie, M., et al., (2018). *The Plant Cell* 30, 1645-1660), that established that the phenylpropanoid pathway is induced upon over-expression of PtrEPSP-TF, which suppresses the expression of a SLEEPER-like repressor of the pathway. To confirm this hypothesis, the inventors looked for transcriptional regulators related to cell wall biosynthesis among a total of 221 predicted transcriptional regulators. A total of 43 NAC and MYB transcription factors were up-regulated by PtrEPSP-TF. Among these transcription factors, four master regulators of phenylpropanoid biosynthesis were found, including NAC and MYB transcription factors LOC_Os12g33070 (MYB46/83), LOC_Os02g46780 (MYB58/63), LOC_Os06g14670 (MYB20) (Zhong, R., et al., (2008). *Plant Cell* 20, 2763-2782), and LOC_Os05g48850 (SND2/3). These four transcription factors and/or their *Arabidopsis* orthologs activate lignin and secondary cell wall biosynthesis (Nakano, Y., et al., (2015). *Front Plant Sci.* 6, 288). For the remaining 39 NAC and MYB transcription factors, the inventors searched for their predicted cis-element binding sites in promoter regions of 3,423 genes specifically up-regulated by the archetypic PtrEPSP-TF. Five transcription factors are presented to highlight using this approach: LOC_Os11g08210 (NAC081), LOC_Os03g42630 (NAC058), LOC_Os05g35500 (MYB4), LOC_Os08g43550 (MYB4), LOC_Os12g07640 (MYB4).

Cis-elements recognized by the five transcription factors were enriched in promoters of these genes. Specifically, the cis-element (TFmatrixID_0382) targeted by LOC_Os11g08210 (NAC081) was found in 1,952 of the 3,423 (57.03%). LOC_Os03g42630 (NAC058) targets the cis-element TFmatrixID_0391, which was found in promoters of 984 out of the 3,423 (28.75%). The cis-element TFmatrixID_0336 targeted by the four MYB4 paralogs LOC_Os05g35500, LOC_Os08g43550, and LOC_Os12g07640 was found in promoters of 963 out of the 3,423 genes (28.13%). Overall, the inventors propose that these five transcription factors in addition to LOC_Os12g33070 (MYB46/83), LOC_Os02g46780 (MYB58/63), LOC_Os06g14670 (MYB20), and LOC_Os05g48850 (SND2/3) may function downstream of the MYB48, XND1, MYB3R3, MYB3R1 and NAC047, which are individually repressed by the archetypic PtrEPSP-TF (FIGS. 8A and 8B).

To validate this proposed PtrEPSP-TF-mediated transcriptional network, the inventors conducted co-expression analysis using existing developmental transcriptome datasets of rice (GEO: GSE51289 (Hirano, K., et al., (2013). *Plant and Cell Physiology* 54, 1803-1821) and GEO: GSE19024 (Wang, L., et al., (2010). *Plant J* 61, 752-766)). In the co-expression analysis, LOC_Os08g43550 (MYB4) and LOC_Os06g24180 (F5H) were not present in the two microarray datasets and were not included in the proposed network (FIG. 8B). Co-expression analyses of the rest of genes except LOC_Os12g33070 (MYB46/83) were performed using dataset GEO: GSE51289 because LOC_Os12g33070 (MYB46/83) is not included in the dataset. The inventors used dataset GEO: GSE19024 to analyze the co-expression of LOC_Os12g33070 (MYB46/83) with other members in the PtrEPSP-TF-mediated network (Hirano, K., et al., (2013). *Plant and Cell Physiology* 54, 1803-1821). As shown in FIG. 8B, expressions of most Layer one genes (down-regulated by PtrEPSP-TF) were negatively co-related with expressions of Layer two genes (up-regulated by PtrEPSP-TF) and even some lignin/phenylpropanoid biosynthetic genes (green lines, FIG. 8B). As predicted, expressions of Layer two genes displayed significant positive co-expression with expression of PALs (LOC_Os04g43760, LOC_Os04g43800), C4H (LOC_Os05g25640), 4CLs (LOC_Os01 g67540, LOC_Os02g46970), CADs (LOC_Os02g09490, LOC_Os08g16910, LOC_Os09g23540, LOC_Os09g23550, LOC_Os10g29470), HCTs (LOC_Os06g08580, LOC_Os11g42370), F5H (LOC_Os10g36848), and Laccases (LOC_Os01g27700, LOC_Os01g62480, LOC_Os05g38390, LOC_Os05g38410, LOC_Os05g38420, LOC_Os07g01110) (FIG. 8B).

Collectively, the transcriptomics analysis and transactivation assay described herein identified five repression targets of PtrEPSP-TF, which may negatively regulate lignin and phenylpropanoid biosynthesis. Based on the presented data, the inventors conclude that modulating the expression of PtEPSP-TF in monocot plants results in similar phenotype alternations as those in dicot plants.

Example 8

*Populus* plants containing rare mutations at PtrEPSP-TF locus show reduced lignin content (Xie, M., et al., (2018). *The Plant Cell,* 30, 1645-1660). However, the underlying molecular mechanism had not been established. By functionally analyzing two natural variants of PtrEPSP-TF, the inventors unveiled that the reduced lignin content and increased sugar release is likely caused by the loss of DNA binding and subsequently reduced transcriptional activities of the variant PtrEPSP-TF. An EMSA assay demonstrated that the two PtrEPSP-TF variants occurring in genotypes BESC-35 and BESC-876 have reduced DNA binding affinity to the PtrhAT promoter, which is the direct target of PtrEPSP-TF. Moreover, the transcriptional repression effects of the BESC-35 and BESC-876 variants on PtrhAT promoter displayed significant reduction in transactivation assays. The HTH motif of PtrEPSP-TF was shown to be responsible for its DNA binding activity (Xie, M., et al., (2018). *The Plant Cell* 30, 1645-1660). Given BESC-35 and BESC-876 variants share the same point mutation close to the HTH motif leading to the D142E amino acid substitution, the 142$^{nd}$ amino acid may play an important role in assisting the proper function of the HTH motif (e.g., protein conformation, target recognition). Although PtrEPSP-TF BESC-876 has another point mutation leading to the L364P amino acid substitution, it did not display additional reduction of DNA binding activity, suggesting that this point mutation may not affect the DNA binding of PtrEPSP-TF. In fact, the L364P substitution is further away from the HTH domain than is the D142E substitution.

Although dicots and monocots have numerous morphological differences in the cell wall, the transcriptional regulatory mechanism appears to be relatively conserved, especially surrounding the critical role of NAC and MYB transcription factors (Nakano, Y., et al., (2015). *Front Plant Sci.* 6, 288; Rao, X., and Dixon, R. A. (2018). *Front Plant Sci* 9, 399). The ortholog of PtrEPSP-TF in rice lacks the DNA-binding HTH motif, thus losing the transcriptional activity. By heterogeneously expressing PtrEPSP-TF in rice, the inventors observed altered thickness of sclerenchyma cell wall, lignin level, secondary metabolism, and transcript levels of genes associated with lignin/phenylpropanoid biosynthesis, which are similar to *Populus deltoides* plants over-expressing PtrEPSP-TF (Xie, M., et al., (2018). *The Plant Cell* 30, 1645-1660). As the major mechanical tissues in rice stem, sclerenchyma fibers have heavily thickened secondary cell walls and are the major contributor of straw biomass. As such, increasing sclerenchyma cell wall thickness is a viable option to enhance the production of straw biomass.

The inventors also observed that lignin/phenylpropanoid biosynthetic genes including PAL, 4CL, C4H, FSH, CAD, CCR, and LACCASE were significantly up-regulated by PtrEPSP-TF in rice. Moreover, master regulators of lignin/phenylpropanoid biosynthesis, such as MYB46/83, MYB58/63, MYB20/43, and SND2/3 also displayed increased expression levels in transgenic rice expressing PtrEPSP-TF. Collectively, the inventors conclude that PtrEPSP-TF may have a relatively conserved effect on the lignin/phenylpropanoid biosynthesis in *Populus* and rice. The fact that transgenic rice expressing PtrEPSP-TF does not exhibit as many up-regulated cellulose and xylan biosynthetic genes as *Populus deltoides* over-expressing PtrEPSP-TF (Xie, M., et al., (2018). *The Plant Cell* 30, 1645-1660) further demonstrates the divergence of secondary cell wall biosynthesis in dicots and monocots. Other regulatory mechanisms of secondary cell wall biosynthesis contain both conserved and divergent parts between dicots and monocots (Rao, X., and Dixon, R. A. (2018). *Front Plant Sci* 9, 399).

The current understanding of the regulation of rice secondary cell wall biosynthesis mainly derives from comparative studies of the main transcriptional regulatory mechanism defined in *Arabidopsis*. Based on molecular and genetic analyses, the inventors were able to identify five repression targets of PtrEPSP-TF in rice: MYB48 (LOC_Os01g74410), XND1 (LOC_Os02g34970), MYB3R3 (LOC_Os05g38460), NAC047 (LOC_Os11g03300), and MYB3R1 (LOC_Os12g13570). Although homologs of these five transcription factors in *Arabidopsis* have been found to either be a transcriptional repressor or negatively affect lignin biosynthesis (Mehrtens, F., et al., (2005). *Plant physiology* 138, 1083-1096; Zhao, C., et al., (2008). *Plant J* 53, 425-436; Rauf, M., et al., (2013). *Plant Cell* 25, 4941-4955; Kobayashi, K. et al., (2015). *EMBO J* 34, 1992-2007), their regulatory roles in lignin and secondary cell wall biosynthesis have not been defined.

Based on RNA-seq and co-expression analyses, the inventors defined their negative regulatory relationships with positive regulators (i.e., MYB46/83, MYB58/63, MYB20/43, SND2/3, NAC081, NAC058, and MYB4) and biosynthetic genes (i.e., PAL, 4CL, C4H, FSH, CAD, CCR, and LACCASE) of lignin and secondary cell wall, which demonstrates the link of the five repression targets of PtrEPSP-TF and the regulation of lignin and secondary cell wall biosynthesis.

With the production of approximately 1,140 million tons biomass per year world-wide, rice straw has been considered as an attractive biomass feedstock for producing second-generation biofuels and bioproducts (Satlewal, A., (2018). *Biofuels, Bioproducts and Biorefining* 12, 83-107). However, to date, the transcriptional regulatory network of lignin and secondary cell wall biosynthesis in rice remains poorly studied. The discovery of the new regulators extends the understanding of the regulatory mechanism of lignin and secondary cell wall biosynthesis in rice and will potentially provide valuable tools to improve rice biomass for the production of biofuels and bioproducts.

Collectively, the inventors' studies of the heterologous expression of PtrEPSP-TF and its two alleles defined one critical amino acid for PtrEPSP-TF transcriptional function and uncovered regulators of secondary cell wall biosynthesis in rice, which enrich the toolbox of the bioengineering for an improved biofuel feedstock. Additionally, comparing gene expression patterns of transgenic *Populus* and rice expressing PtrEPSP-TF provides a better understanding of the evolution of the transcriptional regulatory mechanism of lignin and phenylpropanoid biosynthesis between dicots and monocots.

What is claimed is:

1. A genetically modified plant from the genus *Oryza*, the genetic modification comprising expression of an exogenous nucleic acid encoding a *Populus trichocarpa* 5-enolpyruvylshikimate 3-phosphate synthase transcription factor (PtrEPSP-TF) that comprises a mutation at a position that corresponds to amino acid 364 of SEQ ID NO: 7.

2. The genetically modified plant of claim 1, wherein the mutation results in loss of DNA binding activity of the PtrEPSP-TF protein, wherein the mutant PtrEPSP-TF protein comprises the sequence as shown in SEQ ID NO: 4.

3. The genetically modified plant of claim 1, wherein the PtrEPSP-TF comprises a mutation at a position that is analogous to amino acid 142 and amino acid 364 of SEQ ID NO: 7, resulting in reduced lignin content in the plant.

4. A method comprising: introducing in a plant from the genus *Oryza* an exogenous nucleic acid encoding a *Populus trichocarpa* 5-enolpyruvylshikimate 3-phosphate synthase transcription factor (PtrEPSP-TF) that comprises a mutation at a position that corresponds to amino acid 364 of SEQ ID NO: 7 wherein the mutated PtrEPSP-TF lacks DNA binding activity.

5. The method of claim 4, wherein the mutation results in loss of DNA binding activity of the PtrEPSP-TF protein, wherein the mutant PtrEPSP-TF protein comprises the sequence as shown in SEQ ID NO: 4.

6. The method of claim 4, wherein the mutated PtrEPSP-TF comprises a mutation at a position that is analogous to amino acid 142 and amino acid 364 of SEQ ID NO: 7, resulting in reduced lignin content in the plant.

7. A method for producing a bioproduct, comprising subjecting the genetically modified plant of claim 1 to a bioproduct conversion process.

8. The method of claim 7, wherein the bioproduct is selected from the group consisting of a bioenergy product, a biomaterial, a biopharmaceutical and a biocosmetics.

9. The method of claim 8, wherein the bioenergy product is ethanol and the bioproduct conversion process is an ethanol fermentation process.

10. The method of claim 8, wherein the bioproduct is selected from the group consisting of ethanol, biodiesel, biogas, bioplastics, biofoams, biorubber, biocomposites, and biofibres.

11. A method for production of pulp or paper, comprising producing pulp or paper from the genetically modified plant of claim 1.

12. A genetically modified plant cell or plant tissue, the genetic modification comprising expression of an exogenous nucleic acid encoding a *Populus trichocarpa* 5-enolpyruvylshikimate 3-phosphate synthase transcription factor (PtrEPSP-TF) that comprises a mutation at a position that corresponds to amino acid 364 of SEQ ID NO: 7.

13. A method for production of pulp or paper, comprising producing pulp or paper from the genetically modified plant cell or plant tissue of claim 12.

14. A method for producing a bioproduct, comprising subjecting the genetically modified plant cell or plant tissue of claim 12 to a bioproduct conversion process.

* * * * *